US008420075B2

(12) United States Patent
Sehgal et al.

(10) Patent No.: US 8,420,075 B2
(45) Date of Patent: Apr. 16, 2013

(54) EX VIVO AND IN VIVO EXPRESSION OF THE THROMBOMODULIN GENE FOR THE TREATMENT OF CARDIOVASCULAR AND PERIPHERAL VASCULAR DISEASES

(75) Inventors: Lakshman R. Sehgal, Monarch Beach, CA (US); Jonathan Wong, Palo Alto, CA (US)

(73) Assignee: Biovec, LLC, Chicago, IL (US)

(*) Notice: Subject to any disclaimer, the term of this patent is extended or adjusted under 35 U.S.C. 154(b) by 641 days.

(21) Appl. No.: 12/750,219

(22) Filed: Mar. 30, 2010

(65) Prior Publication Data

US 2010/0240740 A1 Sep. 23, 2010

Related U.S. Application Data

(63) Continuation of application No. 11/685,474, filed on Mar. 13, 2007, now Pat. No. 7,803,365, which is a continuation-in-part of application No. 11/650,478, filed on Jan. 8, 2007, now Pat. No. 7,501,114, which is a continuation-in-part of application No. 10/725,013, filed on Dec. 2, 2003, now Pat. No. 7,179, 459.

(60) Provisional application No. 60/430,099, filed on Dec. 2, 2002.

(51) Int. Cl.
*A01N 63/00* (2006.01)
*A61K 31/715* (2006.01)
*A61K 39/235* (2006.01)
*C07H 21/04* (2006.01)
*C12N 15/861* (2006.01)

(52) U.S. Cl.
USPC ......... 424/93.6; 424/233.1; 435/456; 514/44; 536/23.5; 536/24.1; 536/24.2

(58) Field of Classification Search ................. 424/93.6, 424/233.1; 435/456; 514/44; 536/23.5, 536/24.1, 24.2
See application file for complete search history.

(56) References Cited

U.S. PATENT DOCUMENTS

| | | | |
|---|---|---|---|
| 4,826,811 | A | 5/1989 | Sehgal et al. |
| 4,868,116 | A | 9/1989 | Morgan et al. |
| 5,061,688 | A | 10/1991 | Beissinger et al. |
| 5,339,346 | A | 8/1994 | White |
| 5,438,041 | A | 8/1995 | Zheng et al. |
| 5,449,614 | A | 9/1995 | Danos et al. |
| 5,466,668 | A | 11/1995 | Glaser et al. |
| 5,639,625 | A | 6/1997 | Carson et al. |
| 5,661,033 | A | 8/1997 | Ho et al. |
| 5,827,824 | A | 10/1998 | Light et al. |
| 5,863,760 | A | 1/1999 | Light et al. |
| 5,916,874 | A | 6/1999 | Fujiwara et al. |
| 5,919,619 | A | 7/1999 | Tullis |
| 5,981,225 | A | 11/1999 | Kochanek et al. |
| 5,985,846 | A | 11/1999 | Kochanek et al. |
| 5,994,132 | A | 11/1999 | Chamberlain et al. |
| 6,083,750 | A | 7/2000 | Chamberlain et al. |
| 6,207,455 | B1 | 3/2001 | Chang |
| 6,290,949 | B1 | 9/2001 | French et al. |
| 6,328,958 | B1 | 12/2001 | Amalfitano et al. |
| 6,334,194 | B1 | 12/2001 | Hihara |
| 6,335,011 | B1 | 1/2002 | Podsakoff et al. |
| 6,342,214 | B1 | 1/2002 | Tryggvason et al. |
| 7,132,277 | B1 | 11/2006 | Bett et al. |
| 7,179,459 | B2 | 2/2007 | Sehgal et al. |
| 7,481,998 | B2 | 1/2009 | Sehgal et al. |
| 7,501,114 | B2 | 3/2009 | Sehgal et al. |
| 2002/0068713 | A1 | 6/2002 | Rade et al. |
| 2002/0193336 | A1 | 12/2002 | Elkins et al. |
| 2004/0198683 | A1 | 10/2004 | Sehgal et al. |

FOREIGN PATENT DOCUMENTS

| | | | |
|---|---|---|---|
| WO | 96/06933 | A1 | 3/1996 |
| WO | 99/14346 | A1 | 3/1999 |
| WO | 00/46360 | A1 | 8/2000 |
| WO | 0129058 | A1 | 4/2001 |
| WO | 2004/050844 | A2 | 6/2004 |

OTHER PUBLICATIONS

Supplementary European Search Report mailed Aug. 25, 2011 (Application No. EP 07772782.4, based on PCT Application No. PCT/US2007/006371, filed Mar. 14, 2007).

Parks, et al., "Effects of stuffer DNA on transgene expression from helper-dependent adenovirus vectors", J. Virol. 70 (10): 8027-8034, Oct. 1999.

GenBank Acc. No. M26434, "Human hypoxanthine phosphoribosyltransferease (HPRT) gene, complete cds", US Natl. Library of Med., Bethesda, MD, USA, Nov. 26, 2001.

Orkin, et al., "Report and Recommendations of the Panel to Assess the NIH Investment in Research on Gene Therapy", US National Institutes of Health, Bethesda, MD, USA, Dec. 7, 1995.

Verma, et al., "Gene therapy—promises, problems and prospects", Nature 389: 239-242, 1997.

Rosenberg, et al., "Gene therapist, heal thyself", Science 287: 1751, 2000.

Zuckerbraun, B.S., "Vascular gene therapy: a reality of the 21st century", Arch. Surg. 137: 854-861, Jul. 2002.

Esmon, C.T., "Protein C in sepsis", Ann. Med. 34: 598-605, 2002.

Waugh, et al., "Local Overexpression of Thrombomodulin for in Vivo Prevention of Arterial Thrombosis in a Rabbit Model", Circulation Research, vol. 84, No. 1, pp. 84-92, 1999.

Waugh, et al., "Thrombomodulin Overexpression to Limit Neointima Formation", Circulation, vol. 102, No. 3, pp. 332-337, 2000.

(Continued)

*Primary Examiner* — Kevin K. Hill

(74) *Attorney, Agent, or Firm* — Ping Wang; Andrews Kurth LLP

(57) ABSTRACT

The present invention relates to methods and compositions for treatment of cardiovascular and peripheral vascular diseases using ex vivo and in vivo gene delivery technologies. One aspect of the present invention relates to a method for treating a vascular disease by introducing a DNA sequence encoding a TM protein or its variant into a segment of a blood vessel in vivo using a gutless adenovirus vector. Another aspect of the present invention is to provide a method to deliver a gutless adenovirus vector carrying a DNA sequence encoding a TM protein or its variant using a stent.

18 Claims, 9 Drawing Sheets
(2 of 9 Drawing Sheet(s) Filed in Color)

OTHER PUBLICATIONS

Vassalli, et al., "Gene therapy for arterial thrombosis", Cardiovascular Research, vol. 19, No. 6, pp. 459-459, 1997.
Umana, et al., "Efficient FLPe recombinase enables scalable production of helper-dependent adenoviral vectors with negligible helper-virus contamination", Nature Biotechnology, vol. 19, No. 6, pp. 582-585, 2001.
Wen, et al., "Human Thrombomodulin: Complete cDNA Sequence and Chromosome Localization of the Gene", Biochemistry, vol. 26, pp. 4350-4357, 1987.
Borroni, et al., "Peripheral Blood Abnormalities in Alzheimer Disease: Evidence for Early Endothelial Dysfunction", Alzheimer Disease and Associated Disorders, vol. 16, No. 3, pp. 150-155, 2002.
McKay, et al., "Gene Transfer Therapy in Vascular Disease", Cardiovascular Drug Reviews, vol. 19, No. 3, pp. 245-262, 2001.
Ausbel, et al., (eds) Greene Publishing Associates, "Current Protocols in Molecular Biology", Sections 9.10-9.14, 1989.
Ng, et al., "Development of a FLP/fre System for Generating Helper-Dependent Adenoviral Vectors", Molecular Therapy, vol. 3, No. 5, pp. 809-815, 2001.
Bledsoe, et al., "Cytokine production in motor neurons by poliovirus replicon vector gene delivery", Nature Biotechnol., vol. 18. pp. 964-969, 2000.
Chen, et al., "Low-Dose Vaccinia Virus-Mediated Cytokine Gene Therapy of Glioma", Journal of Immunotherapy, vol. 24, pp. 46-57, 2001.
Chen, et al., "Gene therapy for brain tumors: Regression of experimental gliomas by adenovirus-mediated gene transfer in vivo", Proc. Natl. Acad. Sci. USA, vol. 91, pp. 3054-3057, 1994.
Cui, et al., "Plasmid DNA-Entrapped Nanoparticles Engineered from Microemulsion Precursers: in Vitro and in Vivo Evaluation", Bioconjugate Chem., vol. 13, pp. 1319-1327, 2002.
Curiel, "Strategies to Adapt Adenoviral Vectors for Targeted Delivery", Annals New York Academy of Sciences, vol. 886, pp. 158-171, 1991.
Gossen, et al., "Transcriptional Activation by Tetracyclines in Mammalian Cells", Science, vol. 268, pp. 1766-1769, 1995.
Gossen, et al., "Tight control of gene expression in mammalian cells by tetracycline-responsive promoters", Proc. Natl. Acad. Sci. USA, vol. 89, pp. 5547-5551, 1992.
Fink, et al., "Gene Transfer to Neurons Using Herpes Simplex Virus-Based Vectors", Annual Rev. Neurosci., vol. 19, pp. 265-287, 1996.
Flotte, et al., "Gene Expression from Adeno-associated Virus Vectors in Airway Epithelial Cells", Am. J. Respir. Cell. Mol. Biol., vol. 7, pp. 349-356, 1992.
Green, et al., "A New Scalable Method for the Purification of Recombinant Adenovirus Vectors", Human Gene Therapy, vol. 13, pp. 1921-1934, 2002.
Haj-Ahmand, et al., "Development of a Helper-Independent Human Adenovirus Vector and Its Use in the Transfer of the Herpes Simplex Virus Thymidine Kinase Gene", J. Virol., vol. 57., pp. 267-273, 1986.
Howell, et al., "High-Level Dystrophin Expression After Adenovirus-Mediated Dystrophin Minigene Transfer to Skeletal Muscle of Dystrophic Dogs: Prolongation of Expression with Immunosuppression", Human Gene Therapy, vol. 9, pp. 629-634, 1998.
Kay, et al., "Evidence for gene transfer and expression of factor IX in haemophilia B patients treated with an AAV vector", Nature Genetics, vol. 24, pp. 257-261, 2000.
Kessler, et al., "Gene delivery to skeletal muscle results in sustained expression and systemic delivery of a therapeutic protein", Proc. Natl. Acad. Sci. USA, vol. 96, pp. 14082-14087, 1996.
Kistner, et al., "Doxycycline-mediated quantitative and tissue-specific control of gene expression in transgenic mice", Proc. Natl. Acad. Sci. USA, vol. 93, pp. 10933-10938, 1996.
Magari, et al., "Pharmacologic Control of a Humanized Gene Therapy System Implanted into Nude Mice", J. Clin. Invest., vol. 100, pp. 173-206, 1997.
Miller, "Progress Toward Human Gene Therapy", Blood, vol. 76, pp. 271-278, 1990.
Muzyczka, et al., "Use of Adeno-Associated Virus as a General Transduction Vector for Mammalian Cells", Curr. Topics in Micro. and Immunology, vol. 158, pp. 97-129, 1990.
Naldni, et al., "In Vivo Gene Delivery and Stable Transduction of Nondividing Cells by a Lentiviral Vector", Science, vol. 272, pp. 263-267, 1996.
No, et al., "Ecdysone-inducible gene expression in mammalian cells and transgenic mice", Proc. Natl. Acad. Sci., USA, vol. 93, pp. 3346-3351, 1996.
Pruchnic, et al., "The Use of Adeno-Associated Virus to Circumvent the Maturation-Dependent Viral Transduction of Muscle Fibers", Human Gene Therapy, vol. 11, pp. 521-536, 2000.
Ragot, et al., "Efficient adenovirus-mediated transfer of a human minidystrophin gene to skeletal muscle of mdx mice", Nature, vol. 361, pp. 647-650, 1993.
Romano, et al., "Latest Developments in Gene Transfer: Achievements, Perspectives, and Controversies Over Therapeutic Applications", Stem Cells, vol. 18, pp. 19-39, 2000.
Ropert, "Liposomes as a gene delivery system", Brazilian Journal of Medical and Biological Research, vol. 32, pp. 163-169, 1999.
Sakhuja, et al., "Optimization of the Generation and Propagation of Gutless Adenoviral Vectors", Human Gene Therapy, vol. 14, pp. 243-254, 2003.
Samulski, et al., "Helper-Free Stocks of Recombinant Adeno-Associated Viruses: Normal Integration Does Not Require Viral Gene Expression", Journal of Virology, vol. 63, No. 9, pp. 3822-3828, 1989.
Schwarze, et al., "In Vivo Protein Transduction: Delivery of a Biologically Active Protein into the Mouse", Science, vol. 285, pp. 1569-1572, 1999.
Song, et al., "Sustained secretion of human alpha-1 antitrypsin from murine muscle transduced with adeno-associated virus vectors", Proc. Natl. Acad. Sci. USA, vol. 95, pp. 14348-14384, 1998.
Suzuki, et al., "Structure and expression of human thrombomodulin, a thrombin receptor on endothelium acting as a cofactor for protein C activation", EMBO Journal, vol. 6, pp. 1891-1897, 1987.
Wahlfors, et al., "Evaluation of recombinant alphaviruses as vectors in gene therapy", Gene Therapy, vol. 7, pp. 472-480, 2000.
Wang, et al., "A regulatory system for use in gene transfer", Proc. Natl. Acad. Sci. USA, vol. 91, pp. 8180-8184, 1994.
Wang, et al., "Ligand-inducible and liver-specific target gene expression in transgenic mice", Nature Biotechnology, vol. 15, pp. 239-243, 1997.
Yamashita, et al., "Electroporation-mediated Interleukin-12 Gene Therapy Hepatocellular Carcinoma in the Mice Model", Cancer Research, vol. 61, pp. 1005-1012, 2001.
Ye, et al., "Regulated Delivery of Therapeutic Proteins After in Vivo Somatic Cell Gene Transfer", Science, vol. 283, pp. 88-91, 1999.
Yi, et al., "A Cationic Lipid Emulsion/DNA Complex as a Physically Stable and Serum-Resistant Gene Delivery System", Pharmaceutical Research, vol. 17, No. 3, pp. 314-320, 2000.
Xiao, et al., "Efficient Long-Term Gene Transfer into Muscle Tissue of Immunocompetent Mice by Adeno-Associated Virus Vector", Journal of Virology, vol. 70, No. 11, pp. 8098-8108, 1996.
Xiao, et al., "Adeno-Associated Virus as a Vector for Liver-Directed Gene Therapy", Journal of Virology, vol. 72, No. 12, pp. 10222-10226, 1998.
Zhang, et al., "Long-term expression of human alpha-1 antitrypsin gene in mouse liver achieved by intravenous administration of plasmid DNA using a hydrodynamics-based procedure", Gene Therapy, vol. 7, pp. 1344-1349, 2000.
Cui, et al., "Genetic Immunization Using Nanoparticles Engineered from Microemulsion Precursors", Pharmaceutical Research, vol. 19, No. 7, pp. 939-946, 2002.
Kibbe, et al., "Handbook of Pharmaceutical Excipients", 3rd Edition, Pharmaceutical Press London UK, 2000.
Lee, et al., "Crit. Rev. Ther.", Drug Carrier Systems, vol. 14, pp. 173-206, 1997.
Harui, et al., "Vaccination with helper-dependent adenovirus enhances the generation of transgene-specific CTL", Gene Therapy, vol. 11, pp. 1617-1626, 2004.
Johansson, et al., "Adenoviral-Mediated Expression of Porphobilinogen Deaminase in Liver Restores the Metabolic Defect in a Mouse Model of Acute Intermittent Porphyria", Molecular Therapy, vol. 10, pp. 337-343, 2004.

Fu, et al., "Overexpression of SR-BI by Adenoviral Vector Reserves the Fibrate-Induced Hypercholesterolemia of Apolipoprotein E-Deficient Mice", Journal of Biological Chemistry, vol. 278, pp. 52559-52563, 2003.
Brevetti, et al., "Overexpression of endothelial nitric oxide synthase increases skeletal muscle blood flow and oxygenation in severe rat hund limb ischemia", The Society for Vascular Sugery, pp. 820-826, 2003.
Kibbe, et al., "Gene Therapy for Restenosis", Circ. Res., vol. 86, pp. 829-33, 2000.
Shears, et al., "Efficient Inhibition of Intimal Hyperplasia by Adenovirus-Mediated Inducible Nitric Oxide Synthase Gene Transfer to Rats and Pigs in Vivo", J. Am. Coll. Surg., vol. 187, No. 3, pp. 295-306, 1998.
Russell, "The pathogenesis of atherosclerosis: a perspective for the 1990s", Nature, vol. 362, pp. 801-809, 1993.
Sadler, "Thrombomodulin Structure and Function", Tehomb Haemost, vol. 78, pp. 392-395, 1997.
Esmon, "Thrombomodulin as a model of molecular mechanisms that modulate protease specificity and function at the vessel surface", Faseb J., vol. 9, pp. 946-955, 1995.
Salomaa, et al., "Soluble thrombomodulin as a predictor of incident coronary heart disease and symptomless carotid artery atherosclerosis in the Atherosclerosis Risk in Communities (ARIC) Study: a case-cohort study", Lancet, vol. 353, pp. 1729-1734, 1999.
Palmer, et al., "Nitric oxide release accounts for the biological activity of enothelium-derived relaxing factor", Nature, vol. 88, pp. 4651-4655, 1991.
Kubes, et al., "Nitric oxide: An endogenous modulator of leukocyte adhesion", Proc. Natl. Acad. Sci. USA, vol. 88, pp. 4651-4655, 1991.
Steg, et al., "Reduction of Restenosis After Angioplasty in an Atheromatous Rabbit Model by Suicide Gene Therapy", Circulation vol. 96, pp. 401-411, 1997.
Van Belle, et al., "Accelerated Endothelialization by Local Deliery of Recombinant Human Vascular Endothelial Growth Factor Reduces In-Stent Intimal Formation", Biochem. And Biophs. Res. Communications, vol. 235, pp. 311-316, 1997.
Salyapongse, et al., "Gene Therapy and Tissue Engineering", Tissue Engineering, vol. 26, No. 4, pp. 663-676, 1999.
Kon, et al., "Bone Morphogenetic Protein-2 Stimulates Differentiation of Cultured Spinal Ligament Cells from Patients with Ossification of the Posterior Longitudinal Ligament", Calcif. Tissue Int., vol. 60, pp. 291-296, 1997.
Marmur, et al., "Strand Separation and Specific Recombination in Deoxyribonucleic Acids: Biological Studies", PNAS USA, vol. 46, pp. 453-461, 1960.
Doty, et al., "Strand Separation and Specific Recombination in Deoxyribonucleic Acids: Physical Chemical Studies", PNAS USA, vol. 46, pp. 461-476, 1960.
Sambrook, et al., "Analysis of Genomic DNA by Southern Hybridization", Molecular Cloning: A Laboratory Manual, vol. II, pp. 9.31-9.62, 1989.
Zushi, et al., "Aspartic acid 349 in the forth epidermal growth factor-like structure of human thrombomodulin plays a role in its Ca(2+)-mediated binding to protein C", The Journal of Biological Chemistry, vol. 266, No. 30, pp. 19886-19889, 1991.
Parks, et al., "A helper-dependent adenovirus vector system: Removal of helper virus by Cre-mediated excision of the viral packaging signal", PNAS, vol. 93, pp. 13565-13570, 1996.
Lieber, et al., "Recombinant Adenoviruses with Large Deletions Generated by Cre-Mediated Excision Exhibit Different Biological Properties Compared with First-Generation Vectors in Vitro and in Vivo", J. Virol., vol. 70, pp. 8944-8960, 1996.
Dittman, et al., "Human Thrombomodulin: Complete cDNA Sequence and Chromosome Localization of the Gene", Biochemistry, vol. 26, pp. 4350-4357, 1987.
Beauchamp, et al., "Development of a FLP/frt System for Generating Helper-Dependent Adenoviral Vectors", Molecular Therapy, vol. 3, No. 5, pp. 809-815, 2001.
Tsiang, et al., "Functional domains of membrane-bound human thrombomodulin. EGF-like domains four to six and the serine/threonine-rich domain are required for cofactor activity", The Journal of Biological Chemistry, vol. 267, No. 9, pp. 6164-6170, 1992.
Nagashima, et al., "Alanine-scanning mutagenesis of the epidermal growth factor-like domains of human thrombomodulin identifies critical residues for its cofactor activity", The Journal of Biological Chemistry, vol. 268., No. 4, pp. 2888-2892, 1993.
Gerlitz, et al., "Identification of the predominant glycosaminoglycan-attachment site in soluble recombinant human thrombomodulin: potential regulation of functionality by glycosyltransferase competition for serine474", The Biochemical Journal, vol. 295, pp. 131-140, 1993.
Lin, et al., "Modulation of glycosaminoglycan additional in naturally expressed and recombinant human thrombomodulin", The Journal of Biological Chemistry, vol. 269, No. 40, pp. 25021-25030, 1994.
Adler, et al., "The structure of a 19-residue fragment from the C-loop of the fourth epidermal growth factor-like domain of thrombomodulin", The Journal of Biological Chemistry, vol. 270, No. 40, pp. 23366-23372, 1995.
Weiler-Guettler, et al., "A targeted point mutation in thrombomodulin generated viable mice with a prethrombotic state", The Journal of Clinical Investigation, vol. 101, No. 9, pp. 1983-1991, 1998.

Left Inverted Terminal Repeat: 1-103

Encapsidation Signal (Ψ): 183-331

HPRT Introns: 365-10557

Right Inverted Terminal Repeat: 10571-10673 pBR322 ori: 10877-11544

Kanamycin Resistance Gene: 12353-13144

EX VIVO AND IN VIVO EXPRESSION OF THE THROMBOMODULIN GENE FOR THE TREATMENT OF CARDIOVASCULAR AND PERIPHERAL VASCULAR DISEASES

This application is a continuation application of U.S. patent application Ser. No. 11/685,474, filed Mar. 13, 2007, which is a continuation-in-part application of U.S. Ser. No. 11/650,478, now U.S. Pat. No. 7,501,114, filed Jan. 8, 2007, which is a continuation-in-part application of U.S. Ser. No. 10/725,013, now U.S. Pat. No. 7,179,459, filed Dec. 2, 2003, which claims priority from U.S. Provisional Application Ser. No. 60/430,099 filed Dec. 2, 2002. The entirety of all of the aforementioned applications is incorporated herein by reference.

FIELD

The present invention is directed to methods and compositions for the treatment of cardiovascular and peripheral vascular diseases, and in particular, is directed to methods and compositions for ex vivo and in vivo expression of the thrombomodulin gene using gutless adenovirus vector.

BACKGROUND

Atherosclerosis is one of the chief causes of morbidity and mortality in the United States and many other countries of the world. (Zuckerbraun et al., *Arch Surg.* 137:854-861 [2002]; Kibbe et al., *Circ Res.* 86:829-33 [2000]). This process can result in limiting the flow of blood to the heart, kidneys and the peripheral vessels, to name a few. Current approaches to the treatment of lesions in the arteries include coronary artery by-pass graft (CABG) surgery and angioplasty with or without the placement of a stent. The latter may serve as a vehicle for drug delivery, as is currently being tested in clinical trials. A number of pharmacological agents that affect platelet function or provide anticoagulant properties have so far failed to reduce re-occlusion or intimal hyperplasia. (Kibbe et al., *Circ Res.* 86:829-33 [2000]).

Cardiovascular diseases, however, are the result of complex pathophysiologic processes that involve the expression of many proteins and molecules that can adversely affect the grafted vessel (Shears et al., *J. Am Coll Surg.,* 187(3):295-306 [1998]; Ross et al., *Nature,* 362:801-9 [1993]). Approximately 15-30% of patients receiving vein grafts for coronary or peripheral vascular disease require follow-up treatment, either in the form of angioplasty or new grafts.

Thrombomodulin (TM) is an integral membrane glycoprotein expressed on the surface of endothelial cells (Sadler et al., *Trhomb Haemost,* 78:392-95 [1997]). It is a high affinity thrombin receptor that converts thrombin into a protein C activator. Activated protein C then functions as an anticoagulant by inactivating two regulatory proteins of the clotting system, namely factors Va and VI [I]a (Esmon et al., *Faseb J.,* 9:946-55 [1995]). The latter two proteins are essential for the function of two of the coagulation proteases, namely factors IXa and Xa. TM thus plays an active role in blood clot formation in vivo and can function as a direct or indirect anticoagulant.

There are several other proteins or enzymes that have shown to reduce the process of intimal hyperplasia, whose evolution is the cause of late graft failure. For instance, Nitric oxide synthase, an enzyme expressed by endothelial cells has been shown in animal models to inhibit intimal hyperplasia, especially the inducible enzyme (iNOS) (Salmaa et al., *Lancet,* 353:1729-34 [1999]; Palmer et al., *Nature,* 327:524-26 [1987]; Kubes et al., *PNAS USA.,* 88:4651-5 [1991]).

Animal studies shown that cytoxic gene transfection utilizing the Herpes Simplex Virus thymydine kinase gene delivered via an adenoviral vector was able to inhibit intimal hyperplasia (Steg et al., *Circulation,* 96:408-11 [1997]). Vascular endothelial growth factor (VEGF), basic fibroblast growth factor (bFGF) and platelet derived growth factor (PDGF) have all been shown to promote reendothelization and enhance the healing of vascular injury and help limit intimal hyperplasia. (Ban Bellle et al., *Biochem Biophs Res Commun.,* 235:311-16 [1997]; Salyapongse et al., *Tissue Engineering* 26(4):663-76 [1999]).

A gene therapy approach is currently under clinical investigation. It involves the injection, directly into heart muscles, of an adenoviral vector delivery system containing the gene for the expression of vascular endothelial growth factor (VEGF). This is being tested in patients whose coronary vessels are not amenable to standard grafting procedures. However, some recent adverse clinical events demonstrated that injection of large quantities of adenovirus vectors is associated with significant risks. Accordingly, there still exists a need for a method to effectively introduce therapeutic genes, such as TM, into vascular tissues.

SUMMARY

One aspect of the present invention relates to a method for treating a vascular disease in a mammal, said method comprising the steps of: administering intravenously an effective amount of a gutless adenoviral vector comprising a polynucleotide encoding a thrombomodulin protein or its variant, wherein the gutless adenoviral vector comprises the nucleotide sequence of SEQ ID NO:13 or SEQ ID NO:15.

In one embodiment, the gutless adenoviral vector comprises the nucleotide sequence of SEQ ID NO: 13 and SEQ ID NO: 15, and the thrombomodulin protein has an amino acid sequence of SEQ ID NO: 2.

In another embodiment, the polynucleotide encoding the thrombomodulin protein or its variant is under the control of a CMV promoter or an RSV promoter.

In another embodiment, the polynucleotide encoding the thrombomodulin protein or its variant is under the control of a liver specific promoter selected from the group consisting of albumin promoter, alpha-1-antitrypsin promoter and alpha-fetoprotein promoter.

In another embodiment, the gutless virus vector is administered through a portal vein.

Another aspect of the present invention pertains to a gutless adenovirus vector comprising a polynucleotide encoding a thrombomodulin protein having the amino acid sequence of SEQ ID NO:2, a regulatory element operably linked to the polynucleotide sequence; and a stuffer comprising the nucleotide sequence of SEQ ID NO:13 or SEQ ID NO:15, wherein the regulatory element is a liver specific promoter.

In one embodiment, the liver specific promoter is selected from the group consisting of albumin promoter, alpha-1-antitrypsin promoter and alpha-fetoprotein promoter.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION

Figure 1:
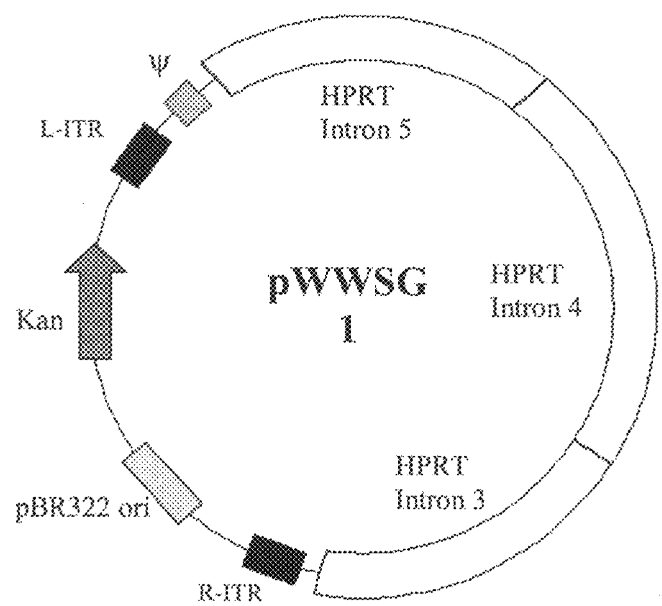
FIG. 1 is a schematic drawing of an embodiment of the backbone shuttle vector pShuttle-ITR-HPRT.

The practice of the present invention will employ, unless otherwise indicated, conventional methods of histology, virology, microbiology, immunology, and molecular biology within the skill of the art. Such techniques are explained fully in the literature. All publications, patents and patent applications cited herein, whether supra or infra, are hereby incorporated by reference in their entirety.

The primary object of the present invention is to provide methods for treating vascular diseases using gene delivery technologies. One aspect of the present invention relates to a method for treating a vascular disease by introducing a DNA sequence encoding a TM protein or its variant into a segment of a blood vessel in vitro using a gutless adenovirus vector and grafting the virus-treated vessel in a patient affected by a vascular disease. The virus-mediated TM expression reduces re-occlusion and intimal hyperplasia in the grafted vessel. This ex vivo approach eliminates the need to inject a large quantity of virus into a patient and hence significantly reduces the viral-related toxicity.

In one embodiment, the method is used for a coronary artery bypass. In another embodiment, the method is used for the treatment of peripheral vascular diseases. In yet another embodiment, the method is used for the maintenance of vein access in renal dialysis patients.

Another object of the present invention is to provide a method to deliver a gutless adenovirus vector carrying a DNA sequence encoding a TM protein or its variant using a stent. The viral vector is embedded in the stent and is released only at a treatment site. Since the viral infection is restricted at the treatment site and the surrounding area, only a small amount of the virus is needed and the virus-related toxicity is reduced.

Yet another object of the present invention pertains to a gutless adenovirus carrying a TM gene. In one embodiment, the gutless adenovirus, which contains a regulatory element operably linked to a DNA sequence encoding a TM protein or its variant and a polyA sequence, is produced using a novel shuttle vector containing a pBR322 replication origin, a selection marker, an adenovirus left inverted terminal repeat, an adenovirus encapsidation signal, a stuffer sequence, and an adenovirus left inverted terminal repeat.

In one embodiment, the regulatory element is a constitutive promoter such a CMV promoter and RSV promoter. In another embodiment, the regulatory element is an inducible promoter.

The forth object of the present invention is to provide a pharmaceutical composition which comprises an effective amount of gutless adenovirus carrying a TM gene of the present invention and a pharmaceutically acceptable carrier. Such compositions may be liquids or lyophilized or otherwise dried formulations and may further include diluents of various buffer content, (e.g., Tris-HCl, acetate, phosphate) pH and ionic strength, additives such as albumin and gelatin to prevent absorption to surfaces, detergents (e.g., Tween 20, Tween 80, Pluronic F68, bile acid salts), solubilizing agents (e.g., glycerol, polyethylene glycerol); anti-oxidants (e.g., ascorbic acid, sodium metabisulfite), and preservatives (e.g. Thimerosal, benzyl alcohol, parabens).

In describing the present invention, the following terms will be employed, and are intended to be defined as indicated below.

"Gene transfer" or "gene delivery" refers to methods or systems for reliably introducing a particular nucleotide sequence (e.g., DNA) into targeted cells. The introduced nucleotide sequences may persist in vivo in episomal forms or integrate into the genome of the target cells. Gene transfer provides a unique approach for the treatment of acquired and inherited diseases, and a number of systems have been developed in the art for gene transfer into mammalian cells. See, e.g., U.S. Pat. No. 5,399,346.

As used herein, the term "effective amount" refers to a level of infection which brings about at least partially a desired therapeutic or prophylactic effect in an organ or tissue infected by the method of the present invention. The infection with an effective amount of the vector carrying genetic material of interest can then result in the modification of the cellular activities, e.g., a change in phenotype, in an organ or a tissue that has been infected by the method of the present invention. In a preferred embodiment, the infection with an effective amount of the vector carrying genetic material of interest results in modulation of cellular activity in a significant number of cells of an infected organ or a tissue.

A gene transfer "vector" refers to any agent, such as a plasmid, phage, transposon, cosmid, chromosome, liposome, DNA-viral conjugates, RNA/DNA oligonucleotides, virus, bacteria, etc., which is capable of transferring gene sequences into cells. Thus, the term includes cloning and expression vehicles including "naked" expression vectors, as well as viral and non-viral vectors. A vector may be targeted to specific cells by linking a target molecule to the vector. A targeting molecule is any agent that is specific for a cell or tissue type of interest, including for example, a ligand, antibody, sugar, receptor, or other binding molecule. The invention is also intended to include such other forms of vectors which serve equivalent functions and which become known in the art subsequently hereto.

The term "expression control element" or "regulatory element" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter" is used herein in its ordinary sense to refer to a, DNA regulatory sequence that is sufficient for RNA polymerase recognition, binding and transcription initiation. Additionally, a promoter includes sequences that modulate the recognition, binding and transcription initiation activity of RNA polymerase. Such sequences may be cis acting or may be responsive to trans acting factors. Depending upon the nature of the regulation, promoters may be constitutive, tissue specific, or regulated. Examples of constitutive promoters include, but are not limited to, SP6, T4, T7, SV40 early promoter, cytomegalovirus (CMV) promoter, RSV promoter, and Moloney murine leukemia virus (MMLV) promoter. Examples of tissue specific promoters include, but are not limited to, liver specific promoters such as albumin promoter, alpha 1-antitrypsin promoter and alpha-fetoprotein promoter, and muscle specific promoters such as muscle creatine kinase (MCK) promoter, myosin promoter, and α-actin promoter.

The term "transduction" denotes the delivery of a DNA molecule to a recipient cell either in vivo or in vitro, via a replication-defective viral vector, such as via a recombinant adenovirus.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as the function to direct the expression thereof. Thus, for example, intervening untranslated yet transcribed sequences can be present between a promoter sequence and the coding sequence and the promoter sequence can still be considered "operably linked" to the coding sequence.

The term "primer" refers to an oligonucleotide which is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

"Hybridization" methods involve the annealing of a complementary sequence to the target nucleic acid (the sequence to be detected). The ability of two polymers of nucleic acid containing complementary sequences to find each other and anneal through base pairing interaction is a well-recognized phenomenon. The initial observations of the "hybridization" process by Marmur and Lane, *PNAS USA* 46:453 (1960) and Doty et al., *PNAS USA* 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

Stability of a nucleic acid duplex is measured by the melting temperature, or "Tm." The Tm. of a particular nucleic acid duplex under specified conditions is the temperature at which on average half of the base pairs have disassociated. The equation for calculating the Tm. of nucleic acids is well known in the art.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data bands, or in a Southern hybridization experiment under, for example, stringent conditions as defined for that particular system. Suitable conditions include those characterized by a hybridization buffer comprising 0.9M sodium citrate ("SSC") buffer at a temperature of about 37° C. and washing in SSC buffer at a temperature of about 37° C.; and preferably in a hybridization buffer comprising 20% formamide in 0.9M SSC buffer at a temperature of about 42° C. and washing in 0.2×SSC buffer at about 42° C. Stringency conditions can be further varied by modifying the temperature and/or salt content of the buffer, or by modifying the length of the hybridization probe as is known to those of skill in the art. Defining appropriate hybridization conditions is within the skill of the art. See e.g., Sambrook, J. Fritsch, E, J., & Maniatis, T. (1989) *Molecular Cloning: A Laboratory Manual* (Cold Spring Harbor Lab, Press, Plainview, N.Y.).

The term "probe" as used herein refers to a labeled oligonucleotide which forms a duplex structure with a sequence in another nucleic acid, due to complementarity of at least one sequence in the probe with a sequence in the other nucleic acid.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like.

The terms "nucleic acid substrate" and nucleic acid template" are used herein interchangeably and refer to a nucleic acid molecule which may comprise single- or double-stranded DNA or RNA.

"Oligonucleotide primers matching or complementary to a gene sequence" refers to oligonucleotide primers capable of facilitating the template-dependent synthesis of single or double-stranded nucleic acids. Oligonucleotide primers matching or complementary to a gene sequence may be used in PCRs, RT-PCRs and the like.

A "consensus gene sequence" refers to a gene sequence which is derived by comparison of two or more gene sequences and which describes the nucleotides most often present in a given segment of the genes; the consensus sequence is the canonical sequence.

The term "native thrombomodulin" refers to both the natural protein and soluble peptides having the same characteristic biological activity of membrane-bound or detergent solubilized (natural) thrombomodulin. These soluble peptides are also referred to as "wild-type" or "non-mutant" analog peptides. Biological activity is the ability to act as a receptor for thrombin, increase the activation of protein C, or other biological activity associated with native thrombomodulin. Oxidation resistant TM analogs are these soluble peptides that in addition to being soluble contain a specific artificially induced mutation in their amino acid sequence.

The term "thrombomodulin variant" is a polypeptide that differs from a native thrombomodulin polypeptide in one or more substitutions, deletions, additions and/or insertions, such that the bioactivity of the native thrombomodulin polypeptide is not substantially diminished or enhanced. In other words, the bioactivity of a thrombomodulin variant may be enhanced or diminished by, less than 50%, and preferably less than 20%, relative to the native protein. Preferred variants include those in which one or more portions, such as an N-terminal leader sequence or transmembrane domain, have been removed. Other preferred variants include variants in which a small portion (e.g., 1-30 amino acids, preferably 5-15 amino acids) has been removed from the—and/or C-terminal of the mature protein.

Preferably, a thrombomodulin variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the bioactivity, secondary structure and hydropathic nature of the polypeptide.

Thrombomodulin variants preferably exhibit at least about 70%, more preferably at least about 90% and most preferably at least about 95% sequence homology to the original thrombomodulin polypeptide.

A thrombomodulin variant also includes a thrombomodulin polypeptides that is modified from the original thrombomodulin polypeptides by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a here moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross links, formation of cysteine, formation of pyroglutamate, formulation, gammacarboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

Adenovirus Vectors:

The genome of an adenovirus can be manipulated such that it encodes and expresses a gene product of interest but is inactivated in terms of its ability to replicate in a normal lyric viral life cycle (Curie D T, *Ann N Y Acad Set* 886, 158-171 [1991]). Suitable adenoidal vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium, endothelial cells and muscle cells. Additionally, introduced adenoidal DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoidal genome for foreign DNA is large (up to 8 kilobases) relative to other gene delivery vectors (Haj-Ahmand et al. *J. Virol.* 57, 267-273 [1986]). Most replication-defective adenoidal vectors currently in use are deleted for all or parts of the viral E1 and E3 genes but retain as much as 80% of the adenoidal genetic material. Adenoidal vectors deleted for all viral coding regions are also described by Kochanek et al. and Chamberlain et al. (U.S. Pat. Nos. 5,985,846 and 6,083,750).

Adenovirus vectors have been successfully tested in a number of animal models (Ragot et al. *Nature* 361, 647-650 [1993]; Howell et al. *Hum Gene Ther* 9, 629-634 [1998]). Nonetheless, the toxicity and immunogenicity remain major hurdles to overcome before the adenovirus vectors can be safely used in humans.

Adenoviruses (Ad) are double-stranded DNA viruses with a linear genome of about 36 kb. The adenovirus genome is complex and contains over 50 open reading frames (ORFs). These ORFs are overlapping and genes encoding one protein are often embedded within genes coding for other Ad proteins. Expression of Ad genes is divided into an early and a late phase. The early genes comprise E1a, E1b, Eta, E2b, E3 and E4, which are transcribed prior to replication of the viral genome. The late genes (e.g., L1-5) are transcribed after replication of the viral genome. The products of the late genes are predominantly components of the virion, as well as proteins involved in the assembly of virions.

The so-called "gutless" rAd vectors contain a minimal amount of adenovirus DNA and are incapable of expressing any adenovirus antigens (hence the term "gutless"). The gutless rAd vectors provide the significant advantage of accommodating large inserts of foreign DNA while completely eliminating the problem of expressing adenoviral genes that result in an immunological response to viral proteins when a gutless rAd vector is used in gene therapy. Methods for producing gutless rAd vectors have been described, for example, in U.S. Pat. No. 5,981,225 to Kochanek et al., and U.S. Pat.

Nos. 6,063,622 and 6,451,596 to Chamberlain et al; Parks et al., PNAS 93:13565 (1996) and Lieber et al., *J. Viral.* 70:8944-8960 (1996).

The "inverted terminal repeats (ITRs) of adenovirus" are short elements located at the 5' and 3' termini of the linear adenoviral genome, respectively and are required for replication of the viral DNA. The left ITR is located between 1-130 by in the Ad genome (also referred to as 0-0.5 mu). The right ITR is located from about 3,7500 by to the end of the genome (also referred to as 99.5-100 mu). The two ITRs are inverted repeats of each other. For clarity, the left ITR or 5' end is used to define the 5' and 3' ends of the ITRs. The 5' end of the left ITR is located at the extreme 5' end of the linear adenoviral genome; picturing the left ITR as an arrow extending from the 5' end of the genome, the tail of the 5' ITR is located at mu 0 and the head of the left ITR is located at about 0.5 mu (further the tail of the left ITR is referred to as the 5' end of the left ITR and the head of the left ITR is referred to as the 3' end of the left ITR). The tail of the right or 3' ITR is located at mu 100 and the head of the right ITR is located at about mu 99.5; the head of the right ITR is referred to as the 5' end of the right ITR and the tail of the right ITR is referred to as the 3' end of the right ITR. In the linear adenoviral genome, the ITRs face each other with the head of each ITR pointing inward toward the bulk of the genome. When arranged in a "tail to tail orientation" the tails of each ITR (which comprise the 5' end of the left ITR and the 3' end of the right ITR) are located in proximity to one another while the heads of each ITR are separated and face outward.

The "encapsidation signal of adenovirus" or "adenovirus packaging sequence" refers to the ψ sequence which comprises five (AI-AY) packaging signals and is required for encapsidation of the mature linear genome; the packaging signals are located from about 194 to 358 by in the Ad genome (about 0.5-1.0 mμ).

One aspect of the present invention relates to a viral backbone shuttle vector for the construction of gutless rAd vectors. In one embodiment, the viral backbone shuttle vector of the present invention contains a left and a right inverted terminal repeats of adenovirus, an encapsidation signal (ψ) of adenovirus, a pBR322 replication origin, a kanamycin resistance gene, and a stuffer sequence, which is the hypoxanthine phosphoribosyltransferase (HPRT) intron fragment with an approximately 10 kb. (SEQ ID NO: 1).

The viral backbone shuttle vector of the present invention contains multiple restriction endonuclease sites for the insertion of a foreign DNA sequence of interest. In one embodiment, the viral backbone shuttle vector contains seven unique cloning sites where the foreign DNA sequence can be inserted by molecular cloning techniques that are well known in the DNA cloning art. The foreign DNA sequence of interest typically comprises cDNA or genomic fragments that are of interest to transfer into mammalian cells. Foreign DNA sequence of interest may include any naturally occurring or synthetic DNA sequence. The foreign DNA may be identical in sequence to naturally-occurring DNA or may be mutated relative to the naturally occurring sequence. The foreign DNA need not be characterized as to sequence or function.

The size of foreign DNA that may be included in the shuttle vector will depend upon the size of the rest of the vector. If necessary, the stuffer sequence may be removed to adapt large size foreign DNA fragment. The total size of foreign DNA may vary from 1 kb to 35 kb. Preferably, the total size of foreign DNA is from 15 kb to 35 kb.

The foreign DNA may encode protein, or contain regulatory sites, including but not limited to, transcription factor binding sites, promoters, enhancers, silencers, ribosome binding sequences, recombination sites, origins of replication, sequences which regulate RNA stability and polyadenylation signals. The promoters used may vary in their nature, origin and properties. The choice of promoter depends in fact on the desired use and on the gene of interest, in particular. Thus, the promoter may be constitutive or regulated, strong or weak, ubiquitous or tissue/cell-specific, or even specific of physiological or pathophysiological states (activity dependent on the state of cell differentiation or the step in the cell cycle). The promoter may be of eukaryotic, prokaryotic, viral, animal, plant, artificial or human, etc., origin. Specific examples of promoters are the promoters of the genes PGK, TK, GH, α-EF1, APO, CMV, RSV etc. or artificial promoters, such as those for p53, E2F or cAMP.

In one embodiment, the viral backbone shuttle vector of the present invention comprises at least 15 contiguous bases of SEQ ID NO: 1, preferably comprises at least 90 contiguous bases of SEQ ID NO: 1, more preferably comprises at least 300 contiguous bases of SEQ ID NO: 1, and most preferably comprises 3000 or more contiguous bases of SEQ ID NO: 1.

One aspect of the present invention relates to a gutless adenoviral vector that carries a DNA sequence encoding a native TM protein or a variant of a TM protein. In one embodiment, the native TM protein is a human TM protein having the amino acid sequence recited in SEQ ID NO:2. In one embodiment, the DNA sequence is controlled by a regulatory element. In on embodiment, the regulatory element is a constitutive promoter such as the CMV promoter or RSV promoter. In another embodiment, the DNA sequence is controlled by a regulatable expression system. Systems to regulate expression of therapeutic genes have been developed and incorporated into the current viral gene delivery vectors. These systems are briefly described below:

Tet-onloff system. The Tet-system is based on two regulatory elements derived from the tetracycline-resistance operon of the *E. coli* Tn 10 transposon: the tet repressor protein (TetR) and the Tet operator DNA sequence (tetO) to which TetR binds. The system consists of two components, a "regulator" and a "reporter" plasmid. The "regulator" plasmid encodes a hybrid protein containing a mutated Tet repression (tetr) fused to the VP 16 activation domain of herpes simplex virus. The "reporter" plasmid contains a tet-responsive element (TRE), which controls the "reporter" gene of choice. The tetr-VP16 fusion protein can only bind to the TRE, therefore activate the transcription of the "reporter" gene, in the presence of tetracycline. The system has been incorporated into a number of viral vectors including retrovirus, adenovirus (Gossen and Bujard, *PNAS USA* 89: 5547-5551, [1992]; Gossen et al., *Science* 268: 1766-1769, [1995]; Kistner et al., *PNAS USA* 93: 10933-10938, [1996]).

Ecdysone system. The Ecdysone system is based on the molting induction system found in *Drosophila*, but modified for inducible expression in mammalian cells. The system uses an analog of the *drosophila* steroid hormone ecdysone, muristerone A, to activate expression of the gene of interest via a heterodimeric nuclear receptor. Expression levels have been reported to exceed 200-fold over basal levels with no effect on mammalian cell physiology (No et al., *PNAS USA* 93: 3346-3351, [1996]).

Progesterone-system. The progesterone receptor is normally stimulated to bind to a specific DNA sequence and to activate transcription through an interaction with its hormone ligand. Conversely, the progesterone antagonist mifepristone (RU486) is able to block hormone-induced nuclear transport and subsequent DNA binding. A mutant form of the progesterone receptor that can be stimulated to bind through an interaction with RU486 has been generated. To generate a specific, regulatable transcription factor, the RU486-binding domain of the progesterone receptor has been fused to the DNA-binding domain of the yeast transcription factor GALA and the transactivation domain of the HSV protein VP16. The chimeric factor is inactive in the absence of RU486. The addition of hormone, however, induces a conformational change in the chimeric protein, and this change allows binding to a GAL4-binding site and the activation of transcription from promoters containing the GAL4-binding site (Wang et al., *PNAS USA* 93: 8180-8184, [1994]; Wang et al., *Nat. Biotech* 15: 239-243, [1997]).

Rapamycin-system. Immunosuppressive agents, such as FK506 and rapamycin, act by binding to specific cellular proteins and facilitating their dimerization. For example, the binding of rapamycin to FK506-binding protein (FKBP) results in its heterodimerization with another rapamycin binding protein FRAP, which can be reversed by removal of the drug. The ability to bring two proteins together by addition of a drug potentiates the regulation of a number of biological processes, including transcription. A chimeric DNA-binding domain has been fused to the FKBP, which enables binding of the fusion protein to a specific DNA-binding sequence. A transcriptional activation domain also has been used to FRAP. When these two fusion proteins are co-expressed in the same cell, a fully functional transcription factor can be formed by heterodimerization mediated by addition of rapamycin. The dimerized chimeric transcription factor can then bind to a synthetic promoter sequence containing copies of the synthetic DNA-binding sequence. This system has been successfully integrated into adenoviral vectors. Long-term regulatable gene expression has been achieved in both mice and baboons (Magari et al., *J. Clin. Invest.* 100: 2865-2872, [1997]; Ye et al., *Science* 283:88-91, [1999]).

Ex Vivo and In Vivo Thrombomodulin Gene Transfer

The instant invention uses a gutless adenovirus vector to express a native thrombomodulin protein or a variant of the thrombomodulin protein at a vessel graft or angioplasty site to prevent or reduce re-occlusion and intimal hyperplasia. The amino acid sequence of human thrombomodulin (SEQ ID NO: 2) and the DNA sequence encoding human thrombomodulin (SEQ ID NO: 3) have been reported (Suzuki et al. *EMBO J.* 6:1891-1897, [1987]).

In one embodiment, the in vivo expression of thrombomodulin or a thrombomodulin variant is used for the treatment of atherosclerotic cardiovascular disease (CVD). Though venous grafts can be used for bypass surgeries, the veins eventually, become occluded by thrombosis resulting the recurrence of the diseases. In this embodiment, TM gene delivery is used in coronary artery bypass grafting, and vascular graft prostheses to block thrombosis. Specifically, TM gene is introduced into a segment of blood vessel in vitro using a gene transfer vector.

TM gene delivery can be also used for the reduction of no-intima formation, for the prevention of atherosclerosis; for the prevention of myocardial infarction and for the inhibition of fibrinolysis in hemophilic plasma. TM gene transfer at the site of thrombus formation is potent approach to reverse these vascular diseases.

In another embodiment, in vivo TM expression is achieved by embedding a gene transfer vector in a stent which is placed at the treatment site following percutaneous transluminal coronary angioplasty, peripheral artery angioplasty, thrombectomy, or an intravascular stenting procedure.

In another embodiment, the in vivo expression of thrombomodulin, or a thrombomodulin variant is used for the treatment of end stage renal failure (ESRD). ESRD patients often exhibit decreased antithrombotic activity due to low TM levels. In such patients, enhanced in vivo TM gene expression can be potentially very useful.

In another embodiment, the in vivo TM expression is achieved by administering a gene transfer vector to a mammal intravenously (i.v.), intramuscularly (i.m.), intraperitoneally (i.p.) or subcutaneously. For adenoviral and AAV vectors, intravenous administration often lead to viral infection of hepatocytes and transgene expression in the liver. In one embodiment, the viral vectors are administered through the portal vein.

The present invention is further illustrated by the following examples which should not be construed as limiting. The contents of all references, patents and published patent applications cited throughout this application, as well as the Figures and Tables are incorporated herein by reference.

EXAMPLE 1

Construction of Gutless Viral Backbone Shuttle Vector pShuttle-ITR-HPRT 1.1 Creation of pShuttle-ITR An embodiment of a gutless viral backbone shuttle vector pShuttle-ITR-HPRT is shown in FIG. 1. Sequence portion containing R-ITR, PBR322 ori, Kan, L-ITR, and encapsidation signal was obtained from the pAdEasy® system from STRATEGENE®. At by 3667 of the original pShuttle sequence, there is a BamHI site just beyond the R-ITR. PCR primers were designed to include the BamHI site and then were to create an EcoRI site at the end of the R-ITR. The R-ITR was PCR replicated and then digested with BamHI and EcoRI to create sticky ends. The viral backbone was then cut with both BamHI and EcoRI. The BamHI cut the backbone at by 3667 and there was also an EcoRI site inside the MCS at by 377. The backbone portion of the plasmid was then gel purified and the PCR replicated R-ITR was recloned into position. This essentially puts the L-ITR, encapsidation signal, MCS, and R-ITR all in close proximity to each other.

1.2 Creation of pShuttle-ITR-HPRT

Insertion of the HPRT introns was a two step cloning process. First, the viral backbone pShuttle-ITR was digested with EcoRI and XbaI, both enzyme sites are in the MCS. The HPRT source was also digested with EcoRI and XbaI yielding a 7477 by fragment that was cloned into the EcoRI/XbaI digested viral backbone. Then the HPRT source was digested with only XbaI yielding a 2715 by fragment. One of the XbaI sites in this cut is the same XbaI site that was cut from the EcoRIIXbaI double digest in step 1. The viral backbone was cut with only XbaI and the 2715 by fragment was inserted.

Overall, from the HPRT source, the HPRT staffer sequence is inserted into the viral backbone in reverse orientation, hence intron 5, then 4, then 3. The 2715 by fragment was inserted and checked to follow the original source sequence. The new plasmid is designated as pShuttle-ITR-HPRT (SEQ ID NO:1)

EXAMPLE 2

Construction and Preparation of Gutless Viral Shuttle Vector Carrying Human Thrombomodulin or lacZ Gene 2(a) Construction and Preparation of Gutless Viral Shuttle Vector Carrying Human Thrombomodulin Gene 2(a)-1 Creation of pCMV-hTM The insertion of hTM into the gutless adenovirus backbone first required the creation of a CMV-hTM expression cassette.

The intermediate vector used was pcDNA3.1/Zeo(+) (Invitrogen). A CMV promoter is available commercially and a CMV promoter was cloned into the multiple cloning sites (MCS) at the XbaI/EcoRV restriction enzyme site locations. The CMV from ps5 was removed using XbaI/EcoRV. pcDNA3.1/Zeo(+) was cleaved inside the MCS using both XbaI and EcoRV as well. The CMV promoter was then ligated. Due to the location of the enzyme sites in the MCS, the CMV promoter (SEQ ID NO:4) was inserted in a backwards orientation relative to the pcDNA3.1/Zeo (+) plasmid. The human TM cDNA (SEQ ID NO:5) was obtained from Dr. Sadler (Dittman et al., *Biochemistry,* 26(14):4350-4357 [1987]) which the sequence was also submitted to ATCC and to GenBank. The human TM gene was removed from the plasmid using EcoRI and inserted into pcDNA3.1/Zeo(+), also in the reverse orientation to pcDNA3.1/Zeo(+) downstream of the inserted CMV promoter.

2(a)-2 Creation of pShuttle-ITR-PIPRT-CMV-TM

The expression cassette in pCMV-hTM was removed by digesting with PmeI. The gutless adenovirus backbone pshuttle-ITR-HPRT was linearized using SmaI which cuts the plasmid at by 381. The CMV-hTM cassette was ligated to the gutless virus in the forwards orientation. Sequence of the expression cassette (from PmeI site to PmeI site) is shown in SEQ ID NO:6. The new plasmid is designated as pShuttle-ITR-HPRT-CMV-TM.

2(a)-3 Creation of pTMadap

The following linker containing a BstEII and SfiI site was inserted into the BstEII and Bsu36I sites of pShuttle-ITR-HPRT-CMV-TM, resulting in the vector pTMadap (SEQ ID NO:7).

```
                                    (SEQ ID NO: 8)
5'-gtaacactgg cccaggaggc ctttctggtg acccc-3'

                                    (SEQ ID NO: 9)
3'-tgacc gggtcctccg gaaagaccac tggggatt-5'
```

Creation of pTMadap-stuffer1

Based on the published sequence HSU71148 of the human X chromosome region q28 the following PCR primers were synthesized:

```
                                    (SEQ ID NO: 10)
Forward:    5' TAGTTCCTTCTGCCTGGAATAC 3'

                                    (SEQ ID NO: 11)
Reverse:    5' CAAGTCACAAGGATGGACTACA 3'
```

Amplification of a human DNA sample resulted in the amplification of a 18524 bp DNA fragment (stuffer 1, SEQ ID NO: 12). Stuffer 1 was cut with the restriction enzymes BstEII and SfiI and the resulting fragment of approximately 18371 by was inserted into the BsteII and SfiI sites of pTMadap, resulting in pTMadap-stuffer1.

2(a)-4 Creation of pTMadap-stuffer1-short

To reduce the size of the stuffer1 fragment in pTMadap-stuffer1, pTMadap-stuffer1 was digested with SanDI and BstEII and the resulting DNA ends were modified by a fill-in reaction with Klenow. Re-ligation resulted in the 25207 by vector pTMadap-stuffer1-short. The sequence of stuffer1-short fragment is shown in SEQ ID NO:13.

2(a)-5 Creation of pTMadap-stuffer1-short-stuffer2

The plasmid p2-2 (SEQ ID NO: 14, obtained from GenBank) was cut with NotI and the resulting fragment of approximately 5954 by (stuffer 2, SEQ ID NO: 15) was inserted into the NotI site of pTMadap-stuffer1 short, resulting in pTMadap-stuffer1-short-stuffer2.

2(a)-6 Removal of Pad Site from pTMadap-stuffer1short-stuffer2

Figure 2:
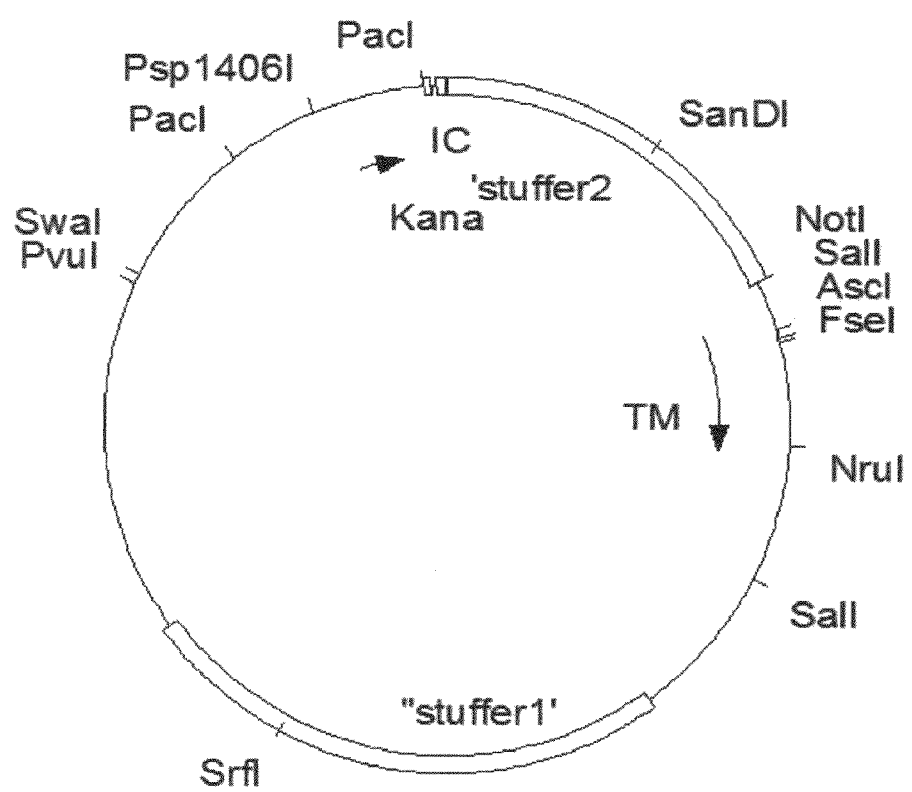
FIG. 2 is a schematic drawing of an embodiment of the full length backbone vector pTM-final.

Plasmid pTMadap-stuffer1-short-stuffer2 was cut with AclI and BsiW1. The resulting 28790 by fragment was isolated from gel. pShuttle-ITR-HPRT (SEQ ID NO:1) was cut with AclI and Acc651. The resulting 1966 by fragment was ligated into the isolated 28790 by fragment, resulting in the full length backbone vector pTM-final (FIG. 2 and SEQ ID NO: 16).

2(b) Construction and Preparation of Gutless Viral Shuttle Vector Carrying LacZ Gene The insertion of LacZ also required creation of an intermediate vector to create the expression cassette. pcDNA3.1/Zeo (+) was again used. First, a portion of the vector from the end of the MCS, restriction enzyme site ApaI, to the beginning of the SV40 poly A, restriction site NaeI, was removed and the vector relegated to itself. Then the LacZ gene was inserted into the vector MCS using NotI/XbaI. The expression cassette, containing CMV promoter, LacZ gene, and SV40 poly A, was removed using NruI/SalI retraction enzymes and blunt-end cloned into the gutless adenovirus at the Sinai restriction enzyme site.

EXAMPLE 3

Preparation of Gutless Adenovirus Carrying Human Thrombomodulin Gene (Gutless Ad.hTM)

The gutless Ad.hTM was prepared according to the following protocol:

1. Linearize pTM-final by digestion with PacI. The completeness of the digestion is confirmed by electrophoresis using a small aliquot of the digestion product. It's not necessary to gel purify the digested pTM-final for transfection described in step 2).

2. Transfect 293FLP cells grown in a 60 mm dish at about 80% confluence with about 5 μg of PacI-digested pTM-final using lipofectamine. 293FLP cells are 293 cells engineered to express the flp gene product, which recognizes the FRS flanking the encapsidation signal and cleaves out the encapsidation signal thereby not allowing helper-viral DNA to be packaged. (Beauchamp et al., *Molecular Therapy,* 3(5):809-815 [2001]; Umana et al., *Nature Biotechnology,* 19:582-585 [2001]).

3. Twenty-four hours after the transfection, infect the cells with helpervirus H10 in 2% DMEM-F12 at a multiplicity of infection (MOI) of 10.

4. Remove the cells from the plate (preferably with a cell scraper) after the appearance of cytopathic effect (CPE), place the cells in a sterile 15 ml tube, and lyse the cells by three freeze-and-thaw cycles. Precipitate the cell debris by spinning the lysate for 5 minutes at 4000 rpm and harvest the supernatant. The supernatant is designated as P0 (passage number 0) supernantant.

5. Infect 293FLP cells in two T75 flask at 80% confluency with 4 ml of P0 supernatant and with the helpervirus at MOI of 1.

6. Continue passaging virus in the manner described in steps 4 and 5 until passage 6 and confirm that helpervirus is added at an MOI of 1 at each passage.

7. Add the P6 supernatant to 8 T500 flasks containing 293FLP cells at 80% confluency and infect the cells with the helpervirus at a MOI of 1.

8. Following CPE, harvest the cells into 500 ml sterile tubes. Centrifuge the cell suspension at 4500 rpm, 4° C. for 10 minutes.

9. Resuspend the cell pellet in 2% DMEM-F12 (the pellet can be stored at −80° C. at this stage).

10. Freeze-thaw the resuspended cell pellet three times. Spin down the cell debris by centrifugation at 4000 rpm, 4° C. for 10 minutes.

11. Transfer the supernatant, which contains the released virus, to a fresh sterile culture tube and subject the supernatant to a second round of centrifugation to further remove cell debris.

12. Transfer the supernatant to a fresh sterile tube. The virus is ready for CsCl-purification.

13. To purify the virus, ultra-clear SW41 (Beckman) tubes were prepared by soaking in Ultra Pure Water, then 70% ETON. Cotton swabs (one swab for each tube) were used to completely dry out the tube, and two tubes were used per sample.

14. Preparation of the first gradient: 2.5 mL CsCl—Density 1.25, and 2.5 mL CsCl—Density 1.40. Place the 1.25 density CsCl into the Beckman tubes first. Underlay slowly the high density, 1.40 CsCl using a sterile pasteur pipette, and overlay an equal amount (in mL) of CVL, about 4.25 ml/tube. Samples were centrifuged in a SW41 rotor with speed: 35,000 rpm at 20° C. for 1 hour and with acceleration: 1 and deceleration: 4. The lower opalescent band was collected using 1 or 3 mL syringe with green cap needles.

Preparation of second gradient: CsCl was prepared to density 1.33 g/ml. Two fresh ultra-clear tubes were placed 8 mL of CsCl and overlay the band just recovered after the first spin. (To equilibrate the tubes, measure before the volume of the recovered band and divide equally in the 2 tubes). Samples were centrifuged at the conditions above for 18 hours. The opalescent band was recovered and collected in a sterile eppendorf tube. (From this moment, keep the tube always on ice). Samples were dialyze with dialysis buffer: (1) 10× Dialysis Buffer: 100 mM Tris—pH 7.4, 10 mM $MgCl_2$; (2) 1× Dialysis Buffer (2 Liters): 400 mL Glycerol, 200 mL 10× Dialysis Buffer 140 mL, and Ultra Pure Water. The dialyzed samples were immediately stored at −70° C.

(c) Determination of Virus Titer

BioRad protein estimation kit was used with 1:5 diluting, and placing 1 ml in each disposable cuvette. Standards were set up at 0, 1, 2, 5 10, and 15 μg/ml. (BSA is fine). Sample cuvettes were prepared using 1-10 μl of sample, depending on estimate of titer. (Sample OD must be within the linear range of the standard line.) OD was taken at 595λ and formula of the line was calculated from standards. The protein concentration of the samples was calculated using this formula. The following formula was used to convert protein concentration to titer: $[12.956+224.15\ (\mu g/ml)]\times10^8$.

EXAMPLE 4

Figure 3:
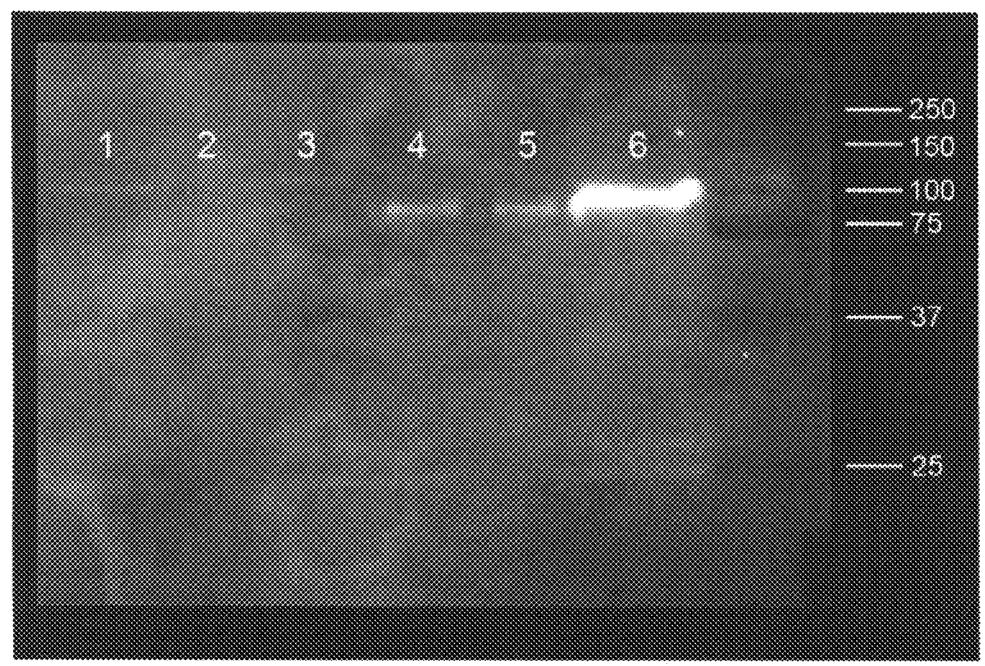
FIG. 3 is a picture of a Western blot showing hTM expression in HEK 293 cells transfected with pTM-final (the full size backbone of gutless Ad.hTM). Lanes 1-3: lysate from control cells; Lanes 4-6, lysate from pTM-final transfected cells.

Expression of Human Thrombomodulin (hTM) In Vitro (A) Expression of hTM in HEK 293 Cells Transfected with pTM-Final HEK 293 cells were cultured in a 6 well cluster and transfected with 1 μg of pTM-final. After 24 hours, the cells were washed with PBS and lysed in 125 μl RIPA buffer with protease inbitors Protein samples (16 μl) were separated on 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) was used to detect the proteins. As shown in FIG. 3, hTM expression was detectable in cells transfected with pTM-final.

The RIPA buffer was prepared according the following recipe: mixing 100 μl Igepal ca-630, 50 mg sodium deoxycholate, 500 μl 120% SDS, 10 mM β-mercapto ethanol, and 1 ml 10×PBS, and add water to a final volume of 10 ml at room temperature. A cocktail of protease inhibitors containing 11.5 μl PMSF (from 34.8 mg/ml in isopropanol, 64 μl Benzamidine (from 15.6 mg/ml stock), 100 μl sodium orthovanadate (100 mM), 5 μl pepstadine (from 1 mg/ml stock), 1 μl leupeptine (from 5 mg/ml stock), and 1 μl aprotin (from 5 mg/ml stock) was added to the RIPA buffer immediately before use.

(B) Expression of hTM in P2 Lysate of 293FLP Cells

Figure 4:
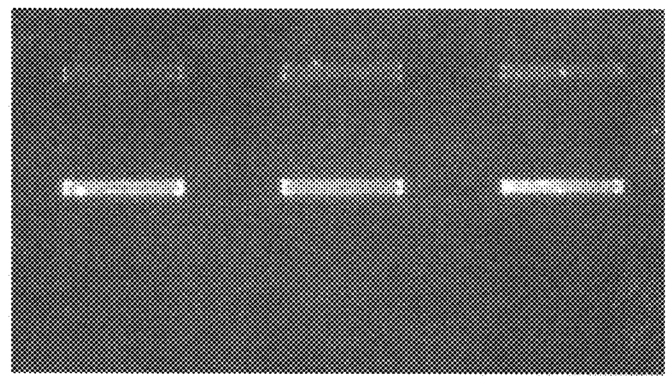
FIG. 4 is a picture of a Western slot blot showing hTM expression in 293FLP cells (passage number 2 (P2) during viral amplification). Row 1, lane 1-3: TM detection using 5 ul cell lysate of P2. Row 2, lane 1-3: TM detection using 30 ul cell lysate of P2. Row 3, lane 1-3: negative control cells.

The P2 lysate was generated as described in Example 3. After CPE was observed, 293FLP cells were detached from the bottom of the culture flask by repeated tapping of the flask. 1 ml of the total of 10 ml of cell suspension was used for the detection of TM expression. The cells in the 1 ml cell suspension were collected by centrifugation for 10 min at 300×g and lysed in 2500 RIPA buffer, 7 ul of 5× loading buffer was added to 35 μl of the lysed cells and the resulting solution was immersed in boiling water for 3 minutes. 5 and 30 ul of boiled cell lysate were diluted with 250 ul TBS (137 mM sodium chloride, 10 mM Tris, pH is 7.4 at +25° C.) and transferred to a nitrocellulose membrane using a slotblot device (Bio-Dot SF, Biorad). Primary antibody (goat anti-hTM (c-17) 1:2000 dilution, Santa Cruz) and secondary antibody (polyclonal rabbit anti-goat immunoglobulins/HRP, 1:4000 dilution, DakoCytomation)) were used to detect the proteins. As shown in FIG. 4, hTM was detectable in the P2 lysate.

The 5× loading buffer was prepared by mixing 20.0 ml 30% SDS, 11.5 ml 2M sucrose, 6.5 ml 2M Tris-HCL pH 6.8, 2.0 ml beta-mercaptoethanol and bromophenolblue. The RIPA buffer was prepared as described in Example 4(A). A cocktail of protease inhibitors containing 11, 5 μl PMSF (from 34, 8 mg/ml in isopropanol, 64 μl Benzamidine (from 15, 6 mg/ml stock), 100 μl sodium orthovanadate (100 mM), 5 μl pepstadine (from 1 mg/ml stock), 1 μl leupeptine (from 5 mg/ml stock), and 1 μl aprotin (from 5 mg/ml stock) was added to the RIPA buffer immediately before use.

(C) Expression of TM in Virus Infected Vena Cava

Vena cava was excised from rats and cut into six segments of approximately 3 mm long. The segments were incubated for 30 minutes in medium containing gutless luc or TM virus. After incubation, the segments were washed three times and transferred to a 24-well plate containing DMEM. The segments were incubated overnight in an atmosphere of 95% $O_2$ and 5% $CO_2$ with gentle shaking. After 24 hours of incubation the segments were frozen. The frozen sections were thawed in lysis buffer and loaded onto a 7.5% SDS acrylamide gel. After blotting, the blot was probed with an antibody against human TM.

Figure 5:
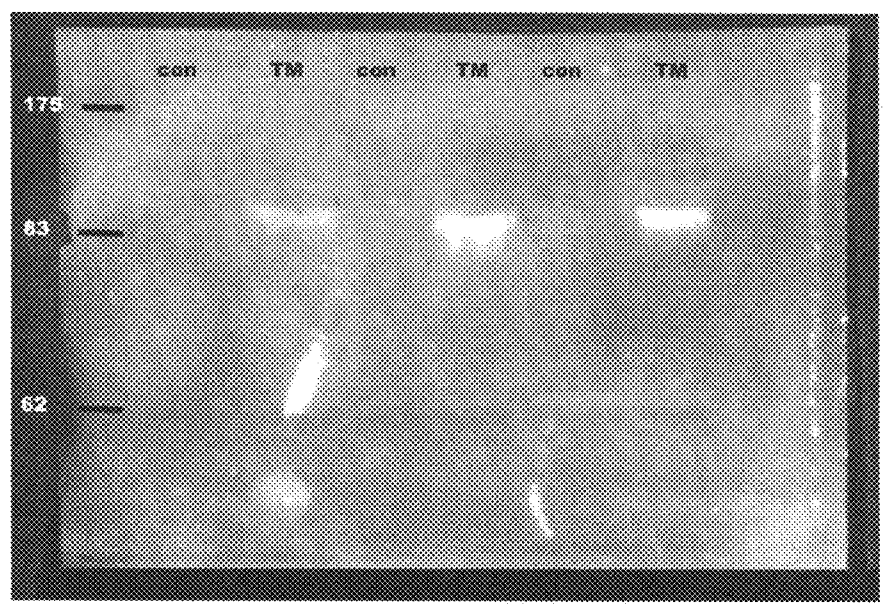
FIG. 5 is a picture of a Western blot showing hTM expression in rat vena cava infected with gutless TM virus.

The Western blot clearly shows that within 24 hours TM expression can be detected (FIG. 5).

As a control, the same HUVEC cells will be infected the gutless adenovirus expressing LacZ. These cells will subsequently be stained with X-gal to look for blue cells. This will demonstrate the viability of the gutless adenovirus backbone itself.

(D) TM Expression in HEK 293 Cells Infected with TM Gutless Virus Passage 1-6

The TM-vector backbone was released by digestion with PacI. 293CRE cells were cultured in a 60 mm dish at 80% confluency. Cells were transfected with 5 μg of Pad digested TM-vector backbone. After 24 hours, 2% DMEM-F12 containing helper virus with a MOI of 10 was added. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=0.

4 ml of P=0 supernatant was added to 2 T75 dish containing 293CRE cells at 80% confluence. Cells were subsequently infected with helpervirus at MOI of 1. Following CPE, cells were removed from the dish and medium and cells were collected a in a sterile 15 ml tube. Cells went through three freeze/thaw cycles and the resulting suspension was centrifuged for 5 minutes at 4000 rpm. The cleared lysate was collected and name P=1. This procedure was repeated until P=6.

Figure 6:
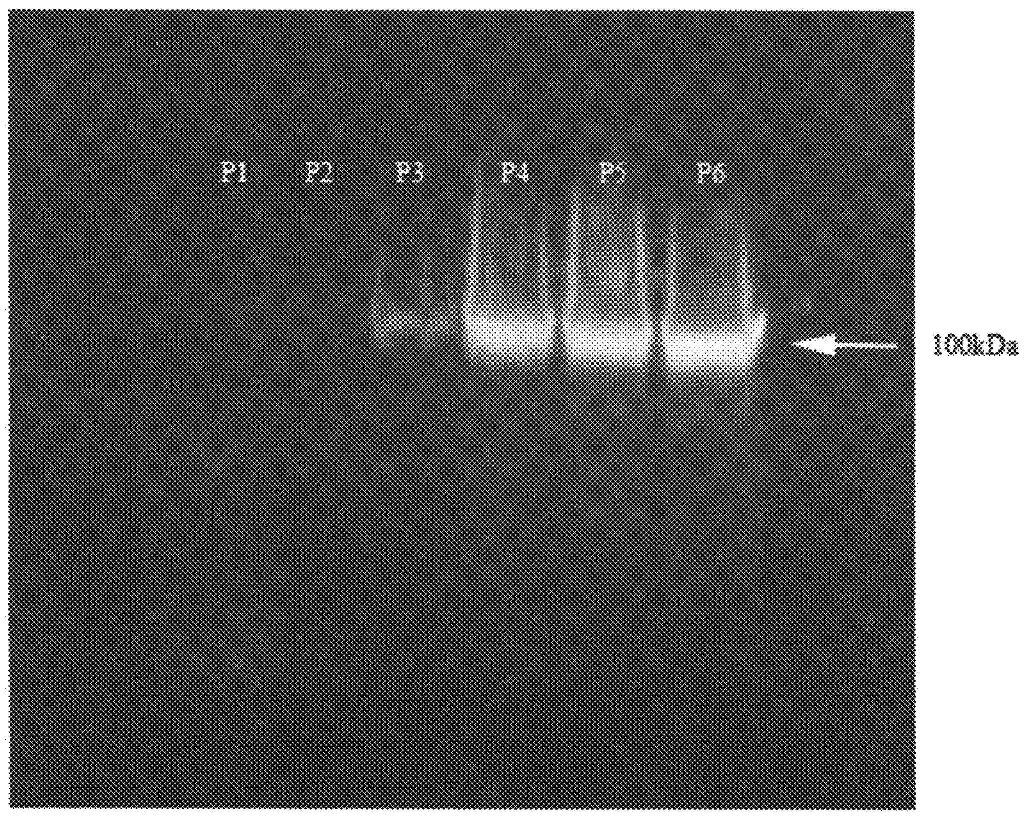
FIG. 6 is a picture of a Western bolt showing TM expression in CRE cells at passage number 1-6 (P1-P6).

HEK 293 cells were cultured in a 6 well cluster and transfected with 200 μl of TM gutless virus of passage 1-6. After 24 hours, the cells were washed with PBS and lysed in 125 μl RIPA buffer. Protein samples (16 μl) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytornation) were used to detect the proteins. As shown in FIG. 6, TM expression is higher in cells infected with virus of higher passage numbers, indicating successful amplification of TM gutless virus in 293CRE cells.

The RIPA buffer (10 ml) was prepared as follows: 100 μl Igepal ca-630, 50 mg sodium deoxycholate, 500 μl 20% SDS, 10 mM β-mercapto ethanol, 1 ml 10×PBS, add water to make up 10 ml. Immediately before use, the following protease inhibitors were added to the RIPA buffer: 115 μl PMSF (from 34.8 mg/ml in isopropanol), 64 μl Benzamidine (from 15.6 mg/ml stock), 100 μl sodium orthovanadate (100 mM), 5 μl pepstatin (from 1 mg/ml stock), 1 μl leupeptin (from 5 mg/ml stock), 1 μl aprotin (from 5 mg/ml stock).

EXAMPLE 5

Composition of the Complete Viral Delivery System (CVDS)

The Complete Viral Delivery System composes of 1:1 mixture of Ham's F12 medium and DMEM, an effective amount of a gutless virus vector carrying a polynucleotide encoding a thrombomodulin protein or a variant of a thrombomodulin protein, and an a cellular oxygen carrier. Preferred oxygen carrier includes: unmodified or chemically modified hemoglobin in the range of 3 g/dl to 10 g/dl and perfluorochemical emulsions. The CVDS may optionally contain 1 mM L-glutamine (Sigma), 1.5 g/L sodium bicarbonate (Sigma), 1× antibiotic-antimycotic (GIBCO® 15240). The CVDM maintains tissue viability during the viral treatment of blood vessel.

EXAMPLE 6

Ex Vivo Treatment of Cardiovascular Disease

A vein segment is harvested from the leg and is stored in Ham's F12 medium. Gutless adenovirus suspended in CVDM is then injected into the isolated vein segment and incubated for 10 to 40 minutes depending on the desired level of transfection. The infection may be performed under pressure to enhance efficiency.

After the incubation, the vein segment is washed several times to eliminate all viral particles that have not entered the endothelial cells of the vein segment, and is then grafted into the desired treatment site. The thorough rinse avoids the spread of the viral vector to other organs of the body following in situ grafting, and any systemic immune response to the viral vector.

EXAMPLE 7

In Vivo Treatment for Peripheral Vascular Disease

In this application, the vein in the leg is treated following evacuation of the clot. A catheter is inserted in the leg vein and both the proximal and distal balloons are inflated to isolate the vein segment to be transfected. The segment is evacuated of all blood, rinsed with physiologic saline. The segment is then filled with the CVDS described above, under pressure. The isolated vein segment is exposed to the CVDS for a period of 10 to 45 minutes, depending upon the desired transfection efficiency.

EXAMPLE 8

In Vivo Treatment for Renal Disease

In this application, the vein in the kidney is treated following evacuation of the clot. A catheter is inserted in the kidney vein and both the proximal and distal balloons are inflated to isolate the vein segment to be transfected. The segment is evacuated of all blood, rinsed with physiologic saline; it is then filled with the CVDS described above, under pressure. The isolated vein segment is exposed to the CVDS for a period of 10 to 45 minutes, depending upon the desired transfection efficiency.

EXAMPLE 9

In Vivo Treatment with Virus Containing Stent

In this application, a virus-coated stent is placed at a treatment site after angioplasty. The virus is a gutless adenovirus carrying a polynucleotide encoding a thrombomodulin protein or a variant of a thrombomodulin protein. Alternatively, the virus may be embedded in the stent and is releases gradually through a time-releasing mechanism well-known to one skilled in the art.

EXAMPLE 10

In Vivo Expression of TM by Local Infusion of Viral Vectors

Figure 7:
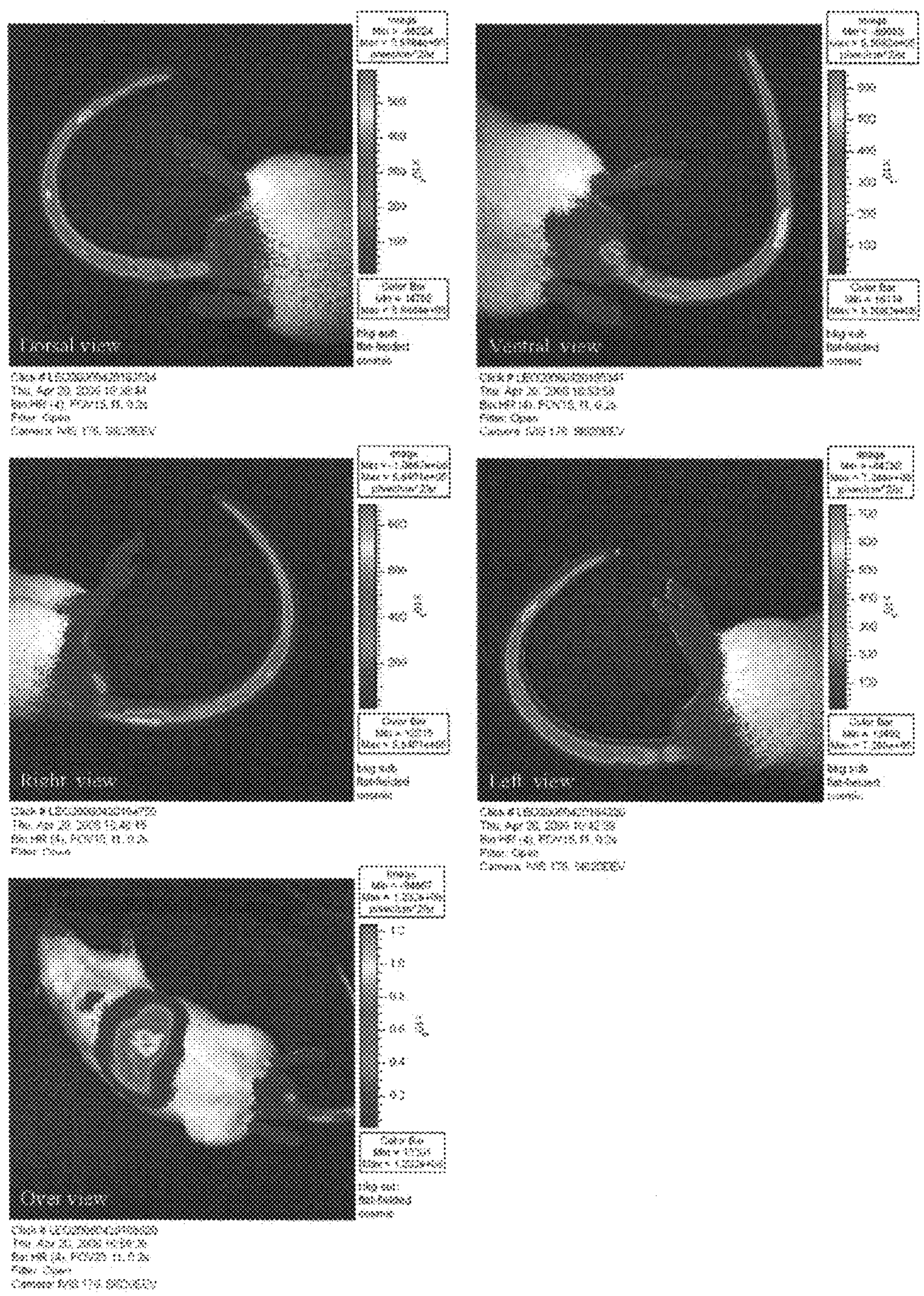
FIG. 7 is a composite of images showing gutless adenovirus-mediated luciferase expression in rat tail vein.

The tail vein of experimental rats was flushed with a solution containing a gutless adenoviral vector carrying a luciferase transgene. As shown in FIG. 7, the expression of luciferase was still very strong in the tail vein eight days after viral infection.

EXAMPLE 11

In Vivo Expression of TM by Intravenous Infusion of Viral Vectors

Material and Methods

Infection with gutless TM virus: 3 male Wistar rats weighing approximately 300 grams were intravenously injected in the tail vein with a low dose of gutless TM virus (approximately $2\times10^{10}$ viral particles) in a total volume of 500 ul of sucrose buffer. After three weeks, the animals were sacrificed and liver tissue and blood plasma was collected and immediately frozen in liquid nitrogen.

TM expression in the liver was determined by western blotting. Approximately 500 mg of liver tissue was homogenized in 2 ml of RIPA buffer. Liver protein samples (20 μg) were separated on a 7.5% polyacrylamide/SDS gel and transferred to nitrocellulose membrane. Primary antibody TM (c-17) (1:2000, Santa Cruz) and secondary antibody Polyclonal Rabbit Anti-Goat Immunoglobulins/HRP (1:4000, DakoCytomation) were used to detect the proteins.

Detection of rat Anti-TM antibodies in the plasma of TM infected rats: MK 293 cells were cultured in a 6 well cluster. 3 wells were infected with 100 μl of TM gutless virus (approximately $4\times10^9$ virus particles) and 3 wells received no virus. After 24 hours, non-infected and TM infected cells were washed with PBS and lysed in 125 μl RIPA buffer. Protein samples (16 μl) were separated on a 7.5% polyacrylamide/SDS gel and transferred to nitrocellulose membrane. Blots containing protein from both TM expressing cells and non-infected cells were incubated with primary antibody TM (c-17) (1:2000, Santa Cruz) or plasma from TM infected rats (1:20, 1:100 and 1:1000 dillution). Detection of primary antibodies was performed using Polyclonal Rabbit Anti-Goat Immunoglobulins/HRP (1:4000, DakoCytomation) and Polyclonal Rabbit Anti-Rat Immunoglobulins/HRP (1:4000, DakoCytomation), respectively. RIPA buffer was prepared as described in Example 4.

Figure 8:
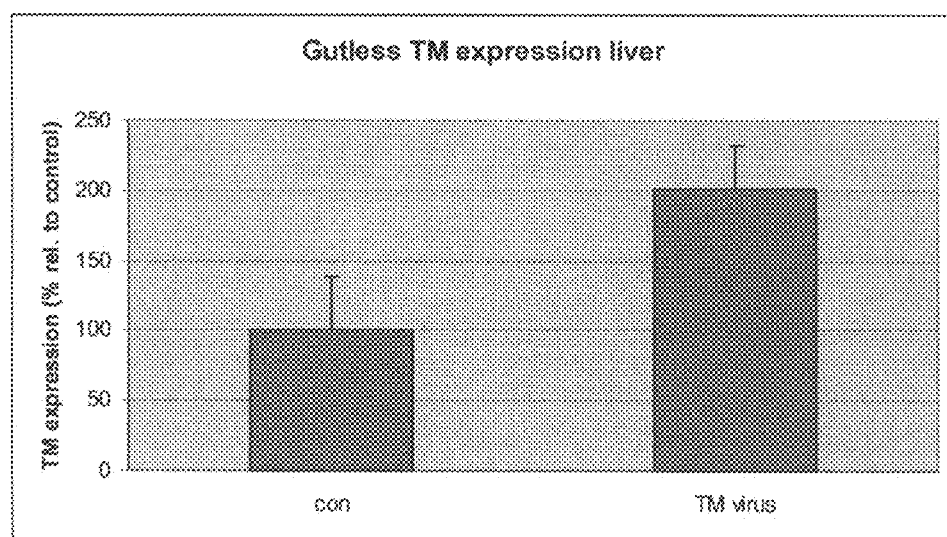
FIG. 8 is a diagram showing TM expression in livers of non-infected rats (con) and TM gutless virus infected rats (TM virus).

TM expression in the liver: No adverse effects of the injection of gutless TM virus could be detected. Animals displayed normal growth characteristics and did not suffer from excessive bleeding. Three weeks after injection, animals were sacrificed and no internal bleeding could be detected. Liver TM expression was evaluated using western-blot. TM expression was elevated two-fold above background levels, indicating modest over-expression of TM gutless virus in the liver three weeks after infection (FIG. 8).

Figure 9:
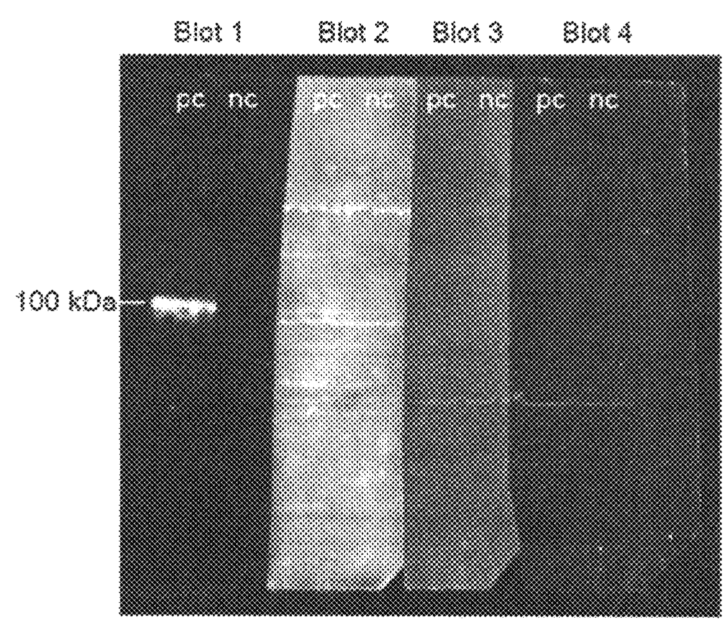
FIG. 9 is a picture of Western blots using a anti-TM antibody (blot 1) and plasma from animals infected with TM virus (blots 2-4).

To detect TM antibodies in the plasma of rats infected with the gutless TM virus, four western blots were made. Each blot contains a protein sample from human cells expressing TM (positive control) and a sample from the same cells that do not produce TM (negative control). Blot 1 was probed with a commercial antibody against TM (FIG. 9, blot 1), indicating the presence of human TM only in the positive control lane. Blots 2,3 and 4 were probed with plasma from animals infected with TM virus in the dilution 1:20, 1:100 and 1:1000, respectively. Although some immunoreactivity is observed, the plasma of rats did not lead to the specific detection of TM in the positive control lane. Therefore, the plasma of these rats do not contain detectable levels of rat IgG antibodies against human TM.

Conclusion: Intravenous administration of low dose gutless TM virus into rat tail vein resulted in modest expression of TM in the liver of the recipient rats three weeks after injection. The viral injection did not result in the production of IgG antibodies against TM.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A gutless virus vector for treating a vascular disease, comprising:

a polynucleotide encoding a thrombomodulin protein having the amino acid sequence of SEQ ID NO:2;

a regulatory element operably linked to the polynucleotide sequence; and a stuffer comprising the nucleotide sequence of SEQ ID NO:13 or SEQ ID NO:15; and wherein said regulatory element is a liver specific promoter.

2. The gutless virus vector of claim 1, wherein said liver specific promoter is selected from the group consisting of albumin promoter, alpha-1-antitrypsin promoter and alpha-fetoprotein promoter.

3. The gutless virus vector of claim 2, wherein said liver specific promoter is the albumin promoter.

4. The gutless virus vector of claim 2, wherein said liver specific promoter is the alpha-1-antitrypsin promoter.

5. The gutless virus vector of claim 2, wherein said liver specific promoter is the alpha-fetoprotein promoter.

6. A gutless virus vector for treating a vascular disease, comprising:

a polynucleotide encoding a thrombomodulin protein or a variant thereof;

a regulatory element operably linked to the polynucleotide sequence; and a stuffer comprising the nucleotide sequence of SEQ ID NO:13 and SEQ ID NO:15; and wherein said regulatory element is a liver specific promoter.

7. The gutless virus vector of claim 6, wherein said liver specific promoter is selected from the group consisting of albumin promoter, alpha-1-antitrypsin promoter, alpha-fetoprotein promoter and alpha-EF1 promoter.

8. The gutless virus vector of claim 7, wherein said liver specific promoter is the albumin promoter.

9. The gutless virus vector of claim 7, wherein said liver specific promoter is the alpha-1-antitrypsin promoter.

10. The gutless virus vector of claim 7, wherein said liver specific promoter is the alpha-fetoprotein promoter.

11. The gutless virus vector of claim 7, wherein said liver specific promoter is the alpha-EF1 promoter.

12. The method of claim 6, wherein said thrombomodulin protein has an amino acid sequence of SEQ ID NO: 2.

13. A gutless virus vector for treating a vascular disease, comprising:

a polynucleotide encoding a thrombomodulin protein;

a regulatory element operably linked to the polynucleotide sequence; and a stuffer comprising the nucleotide sequence of SEQ ID NO:13 or SEQ ID NO:15; and wherein said regulatory element is a liver specific promoter selected from the group consisting of albumin promoter, alpha-1-antitrypsin promoter, alpha-fetoprotein promoter and alpha-EF1 promoter.

14. The gutless virus vector of claim 13, wherein said liver specific promoter is the albumin promoter.

15. The gutless virus vector of claim 13, wherein said liver specific promoter is the alpha-1-antitrypsin promoter.

16. The gutless virus vector of claim 13, wherein said liver specific promoter is the alpha-fetoprotein promoter.

17. The gutless virus vector of claim 13, wherein said liver specific promoter is the alpha-EF1 promoter.

18. The method of claim 13, wherein said thrombomodulin protein has an amino acid sequence of SEQ ID NO: 2.

* * * * *

SEQUENCE LISTING

<160> NUMBER OF SEQ ID NOS: 16

<210> SEQ ID NO 1
<211> LENGTH: 13602
<212> TYPE: DNA
<213> ORGANISM: Artificial Sequence
<220> FEATURE:
<223> OTHER INFORMATION: Description of Artificial Sequence: Synthetic plasmid

<400> SEQUENCE: 1
catcatcaat aatatacctt attttggatt gaagccaata tgataatgag ggggtggagt 60
ttgtgacgtg gcgcggggcg tgggaacggg gcgggtgacg tagtagtgtg gcggaagtgt 120
gatgttgcaa gtgtggcgga acacatgtaa gcgacggatg tggcaaaagt gacgtttttg 180
gtgtgcgccg gtgtacacag gaagtgacaa ttttcgcgcg gttttaggcg gatgttgtag 240
taaatttggg cgtaaccgag taagatttgg ccattttcgc gggaaaactg aataagagga 300
agtgaaatct gaataatttt gtgttactca tagcgcgtaa tactggtacc gcggccgcct 360
cgagtctaga actagtggat cccccgggct gcaggaattc tgatggctct caaaattcct 420
gcctccttta gggataaaag actttaagac tttttaacaa aaaagaaaaa gaaaaaaaaa 480
attcctgcct cctggtgtac acacacagaa gggttccctc cccttgaatg tgaccaggat 540
ctgtgaaaat aacgggatag ccgctcctgt gattaggtta tgtggtagac tagagcaaga 600
ttctcctgct ggttttgaag aagtcagctg ccatgttgtg agactgtcat gggctagggc 660

-continued

```
atgagccttt aaatatctgg gagcaacccc tggccagcag ccagtgagaa aacgggccct    720
cagtcctaca atcacaagga actaaattct gccaacaacc tgaaggaact ttgaagagga    780
tcatgagtcc cttgattcag cttgatgagc ccctgagcag aggatacagc taacttgtac    840
tagggaagta taaaaaacat gcatgggaat gatatatatc aactttaagg ataattgtca    900
tacttctggg aatgaaggga aagaaatggg gctttagttg tattatgatc tttaatttct    960
caaaaaaaat aagatcagaa gcaaatatgg caaaatgtta atacttttgt gggtacgtag   1020
gtattcagca taccctttt tctgagttca aaatatttta taattaaaat gaaatgcagg   1080
ccaggcacag tggctcatgc ctataatacc agcactttgc gaggccgagg tgggaggatg   1140
gcttgaggcc agaccagcct ggccaacatg gcaaaacccc atctctactt aaaaaaaaaa   1200
aaactatata tatatatatg tgtgtgtgtg tgtatatata tatatgtata tatatttata   1260
tatgtgtgta tatatatata tgtatatata tttatatatg tgtgtgtata tatatatata   1320
cacacacaca catatataca tacatacata cacacacaca cacacacaat tagccaggca   1380
tggtggcgca cacctgtagt cccagctact tgggaggctg agacatgaga attgcttgaa   1440
cctgggaggc agagtagtta gtgagctgag atcataccac tgcactccag cctggtgaca   1500
gagtgagact ctgtcttaaa aaaaataaaa attaaaatta aatgcaaaag gtccaagtga   1560
attgaagagg aaaggggtat caaggaaggt tttgtggagg tgacgtttga gctgggtctt   1620
aaatgactta aacatgggat aagaagggag ggaataagga catttcaggt acgagaaata   1680
aggagcaaac agtggaaaca acctaacgtc tgtcaaccag tgaatggata acaaaaatgt   1740
aattcagatg gtatccaact tacgatggtt caacatgaga tttttctgac tttaggatag   1800
atttatcaaa gtagtaaatc cattttcaac ttatgatatt ttcaacttca gatgggttta   1860
tcaggacaca gttgaggaac acctgtctat ccatacaatt tggcaataaa aaggaaatga   1920
gtgcagatat actccacaac atgaatgaac cttgaaaaca ttaagtgaga gaagccagat   1980
acaaaaggcc acatattgta tgattctatt tatacaaaat gtccagaata ggcaaatctt   2040
atagacagca agtaggtaga tgatcagttt gctaggtgct gggggaaggg gaaatgggga   2100
gtgatggcta aggggattgg gtttctttgt ggggcaatga aaatgtttta aaattgagcg   2160
tgataatgat tgcacaatgc tgcatatata tataatctat agattatata tatataaaga   2220
gaggctgtta gacagtgata agtgatatat atatatatat acatagagag agagagagag   2280
agagagagag gctgttagtg ataagtgatc aggaaaataa aagtattgag gaggaatacg   2340
aagttgacgg tgtgaaaaca tgagatttta tataggatgg ccagggaagg ccttaatgag   2400
aaagtgactt atgagtaaaa acaagggatc ctaaacctta gcatgcatca gaatcactcg   2460
gaaacttgtt aaagcatagc ttgctgggcc tcatcacaga tattttgatt cggtaggttc   2520
ttgtctgata ttaatacttt tggtctaggg aaccacattt tgagaaccac tgagctaaag   2580
gaagtaaagg tttcccttag tttactagct ggtaacccta ggaaactgct tagcctctcg   2640
gtgctaagat acaaaatact ttagcacata ataacacatg gaaaatagtc tataaattat   2700
aaatattatt ttttatgtac caaatattac ataagacaaa atctaagcaa gatatatata   2760
tatatacata aaatataaga tatatatgta tatattatat atagataaat agagagagag   2820
agttatgttt agaaagaaaa tacttcaaac taaaaaaaga gaggtaggaa gtataccatt   2880
ccattattgg taaaaacaaa ttactaagta gtctttacaa aaaaccaatc tcactccttt   2940
agaacacaag cccaccatta aaactgatgc agaggaattt ctctccctgg cttaccttta   3000
ggatggtgca tactaagtta gaaaagtcat aaatgttata ttaaaagtaa atgtgaactt   3060
```

```
acttccacaa tcaagacatt ctagaagaaa aagagaaatg aaaatcagta caatgaataa   3120
aacggtattt ccaattataa gtcaaatcac atcataacaa ccctaaggaa ttatccaaac   3180
tcttgttttt agatgcttta ttatatcaaa ctctccttta aacaagtggc ccatctgctg   3240
ggatttggaa gcctgtaata ctgaaatttt catcataatg gaaattttaa aaacagaatt   3300
tgacccacct gtttttaaaa cactttcatt acttaacaag aggtctaatc ttgggcaagt   3360
cttgaaattt ctctggcctt agtttcccat gtgttaaatg aaacttgaag cagttggtct   3420
cttatagtct cctgactcta acattctaag aattatattt gtacaataac tcaaaaatca   3480
cataatttaa tttaccatat ggactccaaa atatattttc tcattaggct aaacttgatc   3540
tgcattttct ggatgtgtcc atattcttgg actacactaa aacatgatac caatgcttcc   3600
tctcaccata aaccctcact tcgctttcta catttaagaa ttttatagct ggaagagtcc   3660
ttaacagaaa ataccatcta ataattaccc ctcaaaatcg agaaagtcct atctgttctt   3720
atgctagtta taagaatgag gcagcatttc acataatggt tataaacact gccacaagaa   3780
gattcatgat gtgttgttta tctgtagctc tcatcatact ctgtcatata actatagcat   3840
taagatttta atgttctata tattcttcta agacagtgtt taccagagta aggcacaaaa   3900
gatccactgg tttgcaagaa agattagaac ttttaaattt tttacctcac cttgtttaat   3960
ctatattttt gtatgtattt tgtaacatat atattattat taccataaat catatataat   4020
ttaaaatgca tatattaggg gtaaatgctc aggaaacttt ttataaattg ggcatgcaaa   4080
tacaagtttg aagactcact gttctaggta ttaaaagtaa agttataacc aagtaaagct   4140
tccacctttt catgtctcaa agcagtttat tgttggaggt aagatctctt agaagcctaa   4200
acaggtccaa gtacagaatg aagtaaggct agcccataac ttgtggcaag caattcatac   4260
tatttctctc atgctgagct ctcctcagtg aagcagctac tatagacaac tgcagcctat   4320
tggtagccta ttttacaggc aggaaaaaaa ttacttttta ttcaaagtgg aactcaggac   4380
atggggagaa aatgaataca aaaaataggg tcaatccaaa ggcacacagc aaatgagtaa   4440
cacagttatg tttttttccc atttgtatga ggtcccagta aattctaagt aaactgcaaa   4500
tttaataata cactaaaaaa gccatgcaat tgttcaaatg aatcccagca tggtacaagg   4560
agtacagaca ctagagtcta aaaaacaaaa gaatgccatt attgagtttt tgaattatat   4620
caagtagtta catctctact taataaatga gaaaaacgag gataagaggc catttgataa   4680
aatgaaaata gccaagaagt ggtattagag acttgaatac aggtattcgg gtccaaagtt   4740
catctgctca aatactaact ggggaaaaga gggaaaaata tttatataca tatatatctg   4800
cacacaaaaa tacccccaaa agacaaaatg aggccaggca gggtggctca cacccgtaat   4860
cccggtactt tgggaggctg aggcaggtgg atacctgaga tcaggagttg gagatcagcc   4920
tggtcaacat ggtgaaaccc tgtctctact aaagataaaa aaattagcca ggcatggtgg   4980
cgtgcgcctg taatcccagc tacttgggag tctgaggcag gagaatcact tgaactggga   5040
aggggaggtt gcagtgagcc aagatcgtac tactgcactc cagcctgggc agcagagtga   5100
gactccatca caaaaataaa taaataaata aaatacaatg aaacagaaag ttcaaataat   5160
cccataatct taccaccaag aaataacttt cactcgttat acttattgat ttttccataa   5220
taaatgtact ttactgtgac tatcatgaaa agaaagttat tttagaaaca gagaactgtt   5280
tcagatcaaa tctatgtagt agaacagagc cattaggtgg gaaagacgag atcaaactaa   5340
atctcagaag gcctaaaagg ctaggtccat tccagcacta aaaactgacc agacaagtaa   5400
tggcttcaac agcttctaaa tatggacaaa gcatgctgaa agggaaggac aggtctaaca   5460
```

```
gtggtatatg aaatgaacag gaggggcaaa gctcatttct cctctgaagt tttccaaaga   5520
tgctgaggag gacattagtt tgacatgacc ctgatatggg acaagataat ttcacagaag   5580
ttttacatgt taaagttttc ttatagatac tcattcaagt aagcaatgaa cactaaaatc   5640
taaagaaaga aaagagcttt agagtcaggt ctgtattcaa attcaagctc taccacttac   5700
tggttctgtg actttgggca agtcttttaa ccttattaag tcttaatttc ctgatttgta   5760
aaatggggat atcgtctccc tcacaggatt gttgtgaaac ttttatgaga ttaatgcctt   5820
tatatttggc atagtgtaag taaacaataa ctggcagctt caaaaaaaaa aagcagtagc   5880
attccatcat ttattattgg ttactctcaa aaagtttttc aatgtactag aagataaata   5940
ttcaaatacc ttaatatctc cattattttc aggtaaacag catgctcctg aacaaccaat   6000
gggtcaacaa ataaattaaa agggaaatct aaaaacatct tgatattaaa ctacatggaa   6060
gcacaatata ccaaaaccaa tggttcacac taggagaatt ttaaggtaca agaaaactct   6120
ttgagatttc ttaaaataat agtatgtctg aatttattga gtgatttacc agaaactgtt   6180
gtaagagctc tacttgcatt atagcactta atcctcttaa ctctatggct gctattatca   6240
acctcaccct aatcacatat gggacacaga gaggttaagt aacttgccca aggtcagagt   6300
taggaagtac taagccatgc tttgaatcag ttgtcaggct ccggaactca cactttcagc   6360
cactacataa tactgctttg ctatctttta ggaaactatg tgagtctacc tcacatagac   6420
tcacataggt ttgttttttt ttttttttta aaggctatct tttcccccat caatgttttt   6480
tgaaggatcc caaattagag tcccacagag gcagacagca gtacttgaca atatggacat   6540
ttaaggttaa tgttggattc tactgtcttt ttactacatg acctagggaa cgataattaa   6600
cctagactgc ttccaagggt taaataaccc atttagttat actatgtaaa ttatctctta   6660
gtgattgatt gaaagcacac tgttactaat tgactcggta tgaagtgctt tttttcttc    6720
cctttcaaga tacatacctt tccagttaaa gttgagagat catctccacc aattactttt   6780
atgtcccctg ttgactggtc attctagtta aaaaaaaaaa aaactatata tatatatatc   6840
tacacacaca tatgtatatg tatatcctta tgtacacaca caaacttcaa attaaatgag   6900
aactagaaga tttgagaagt tagctagcta atatccatag cattatgata ttctaaatga   6960
tatgaattat aagaattagg tttcctgaaa tgaatgacta gaaaactttc aagtagagat   7020
tagtaaaaat taaaaagtcc taatcggcca ttactgattt gatgttttta agagtcctaa   7080
aaaatgggtt acatccattt ttaagtgggt agtattataa cagccaccca tcttcaatca   7140
cagtgatttc tgaattgtga gggaagttat tagcatgaca ggtgtctggt tctggccctg   7200
tacgattccc atgagtcaag caaattgtaa gggctggtct atatcacacc caaccccaag   7260
gatatgtccc tcaaaagtct agcccaggcc ccgtcatctt cagcatcatc tgggaaacca   7320
ggtctgatta gtagtccttt aaggaatacc tcttaggctc ccattttact gctatcacag   7380
aatccaataa aacccttaca ggagattcaa tgggaaatgc tcaacaccca ctgtagttgg   7440
tggtgacaat gaccataatt tggctgtgct ggattcagga cagaaaattt gggtgaaaga   7500
gcaggtgaac aaaagagctt cgacttgccc tagcagagag caagccatac cataccacaa   7560
agccacagca attacaacgg tgcagtacca gcacagtaaa tgaacaaagt agagcccaga   7620
aacagaccca gaactatatg aggatttagt atacaataaa gatggtattt cgagtcagta   7680
gggaaaagat gaattattca ataaatgatg tttggccaac tagtaaccca tttgggaaaa   7740
aataaaagta tggtccctac ctcacagcat acacaaaaat aaattccaga cggattaaaa   7800
tctaaatgta aaaaataaag ccataagtgg actggaagaa aatagagaat ttttttaac    7860
```

```
atccgtagaa agggtaaaaa cccaggcatg acatgaacca aaactgaaga ggttctgtaa    7920
caaatacccc cttttatata ttgggctcca acaataagaa cccataggaa aatggagaat    7980
gaacacaaat agacaattta tagaagagaa ggttataagg tgtaaaatta tatctatctg    8040
agaaacaaac actaaaacaa tgtgattcta ctgttctccc acccatactg gcaaaactta    8100
agcctgataa tatgctgagg ggaaataagc actcttgttg gtgagagtat taattggcat    8160
agcttctttt gaaaatgaca tagcaatacc tgttaaaatt gcaaacatgc atgtcactta    8220
atccagtaat cccacttctg ggaatcaatg ctacaaaaac actgacaagt atacaaagat    8280
acattcaaga gtgttcactg ggccgggtgc ggtggcttca tgcctgtaat cccagggagg    8340
cagaggcaag acgatcgctt gaccccagga gttcaaggcc agcccgagaa acacagcaag    8400
accctgtctc tctttttttt atttaaaaaa taaatgttca ctgtatcagt tgttcacaaa    8460
aacaaaccaa catgtccatt aacagggaac catttaaatt aatcaagttc atctacacaa    8520
tgtaatacca tgcaactatt aaaaagcacc tgataatcca aagcacactg agacagaata    8580
atgctattaa aaacaccaag tagtggaaca ctgtgttgcc tatgacacca tttttattca    8640
acatttaaac aaatttgtaa cagcaattac atgagtagtg acaatggcgt ttatgagact    8700
tttcactttt atgtgcttct atttttgtta tgcttctata tatacatcca tttattatgg    8760
agtgttactt tcaaaaatca caaatgggcc agtattattt ggtgttgcaa ggtgagcata    8820
tgacttctga tatcaacctt tgcatattac ttctcaattt agggaaatta cagacatccc    8880
ttattctaac taacttaaaa cccagcattt caaacataca gaattgatgg ggaaaaaaaa    8940
gaaagaagaa agaaagaaaa ggcaacaagc ttcagatgac agtgactcac atcaaattat    9000
ttataaaatc tgttaaatag tgccatcttc tggagatacc tggtattaca gtccaactcc    9060
agttgatgtc tttacagaga caagaggaat aaaggaaaaa atattcaaga actgaaaagt    9120
atggagtcat ggaaaaattg ctgtgatcca aaggctacgg tgataggaca agaaacaaga    9180
gaactccaag cagtaagaca ctgctgttct attagcatcc aaacctccat actcctgttt    9240
gccccaaggc ttttttaaaa aatagagaca ggatctcact attttgctca ggctggtctt    9300
gaactcctgg actcaagcta tcctcctgcc tcggcctcct aaagtgccga gattacaggc    9360
ttgagtcacc atacctggct atttattttt tcttaactct cttgcctggc ctatagccac    9420
catggaagct aataaagaat attaatttaa gagtaatggt atagttcact acattggaat    9480
acaggtataa gtgcctacat tgtacatgaa tggcatacat ggatcaatta ccccacctgg    9540
gtggccaaag gaactgcgcg aacctccctc cttggctgtc tggaacaagc ttcccactag    9600
atccctttac tgagtgcctc cctcatcttt aattatggtt aagtctagga taacaggact    9660
ggcaaaggtg aggggaaagc ttcctccaga gttgctctac cctctcctct accgtcctat    9720
ctcctcactc ctctcagcca aggagtccaa tctgtcctga actcagagcg tcactgtcaa    9780
ctacataaaa ttgccagaga agctctttgg gactacaaac acataccctt aatgtcttta    9840
tttctatttt gtctacctct tcagtctagg tgaaaaaata ggaaggataa tagggaagaa    9900
ctttgtttat gcctacttat ccgcccctag gaattttgaa aacctctagg tagcaataag    9960
aactgcagca tggtatagaa aaagaggagg aaagctgtat agaaatgcat aataaatggg   10020
caggaaaaga actgcttgga acaaacaggg aggttgaact ataaggagag aaagcagaga   10080
ggctaatcaa caaggctggg ttcccaagag ggcatgatga gactattact aaggtaggaa   10140
ttactaaggg ctccatgtcc ccttagtggc ttagtactat gtagcttgct ttctgcagtg   10200
aacttcagac ccttctttta ggatcctaga atggactttt tttttttatc ggaaaacagt   10260
```

-continued

```
cattctctca acattcaagc aggccccaag tctaccacac tcaatcacat tttctcttca  10320

tatcataatc tctcaaccat tctctgtcct tttaactgtt tttctatacc ctgatcaaat  10380

gccaacaaaa gtgagaatgt tagaatcatg tatttttaga ggtagactgt atctcagata  10440

aaaaaaaagg gcagatattc cattttccaa aatatgtatg cagaaaaaat aagtatgaaa  10500

ggacatatgc tcaggtaaca agttaatttg tttacttgta ttttatgaat tccctaaaac  10560

ctacgtcacc cgccccgttc ccacgccccg cgccacgtca caaactccac cccctcatta  10620

tcatattggc ttcaatccaa aataaggtat attattgatg atgttaatta acatgcatgg  10680

atccatatgc ggtgtgaaat accgcacaga tgcgtaagga gaaaataccg catcaggcgc  10740

tcttccgctt cctcgctcac tgactcgctg cgctcggtcg ttcggctgcg gcgagcggta  10800

tcagctcact caaaggcggt aatacggtta tccacagaat caggggataa cgcaggaaag  10860

aacatgtgag caaaaggcca gcaaaaggcc aggaaccgta aaaaggccgc gttgctggcg  10920

tttttccata ggctccgccc ccctgacgag catcacaaaa atcgacgctc aagtcagagg  10980

tggcgaaacc cgacaggact ataaagatac caggcgtttc cccctggaag ctccctcgtg  11040

cgctctcctg ttccgaccct gccgcttacc ggatacctgt ccgcctttct cccttcggga  11100

agcgtggcgc tttctcatag ctcacgctgt aggtatctca gttcggtgta ggtcgttcgc  11160

tccaagctgg gctgtgtgca cgaacccccc gttcagcccg accgctgcgc cttatccggt  11220

aactatcgtc ttgagtccaa cccggtaaga cacgacttat cgccactggc agcagccact  11280

ggtaacagga ttagcagagc gaggtatgta ggcggtgcta cagagttctt gaagtggtgg  11340

cctaactacg gctacactag aaggacagta tttggtatct gcgctctgct gaagccagtt  11400

accttcggaa aaagagttgg tagctcttga tccggcaaac aaaccaccgc tggtagcggt  11460

ggtttttttg tttgcaagca gcagattacg cgcagaaaaa aaggatctca agaagatcct  11520

ttgatctttt ctacggggtc tgacgctcag tggaacgaaa actcacgtta agggattttg  11580

gtcatgagat tatcaaaaag gatcttcacc tagatccttt taaattaaaa atgaagtttt  11640

aaatcaatct aaagtatata tgagtaaact tggtctgaca gttaccaatg cttaatcagt  11700

gaggcaccta tctcagcgat ctgtctattt cgttcatcca tagttgcctg actccccgtc  11760

gtgtagataa ctacgatacg ggagggctta ccatctggcc ccagtgctgc aatgataccg  11820

cgagacccac gctcaccggc tccagattta tcagcaataa accagccagc cggaagggcc  11880

gagcgcagaa gtggtcctgc aactttatcc gcctccatcc agtctattaa ttgttgccgg  11940

gaagctagag taagtagttc gccagttaat agtttgcgca acgttgttgc cattgctgca  12000

gccatgagat tatcaaaaag gatcttcacc tagatccttt tcacgtagaa agccagtccg  12060

cagaaacggt gctgaccccg gatgaatgtc agctactggg ctatctggac aagggaaaac  12120

gcaagcgcaa agagaaagca ggtagcttgc agtgggctta catggcgata gctagactgg  12180

gcggttttat ggacagcaag cgaaccggaa ttgccagctg gggcgccctc tggtaaggtt  12240

gggaagccct gcaaagtaaa ctggatggct ttcttgccgc caaggatctg atggcgcagg  12300

ggatcaagct ctgatcaaga gacaggatga ggatcgtttc gcatgattga acaagatgga  12360

ttgcacgcag gttctccggc cgcttgggtg gagaggctat tcggctatga ctgggcacaa  12420

cagacaatcg gctgctctga tgccgccgtg ttccggctgt cagcgcaggg gcgcccggtt  12480

ctttttgtca agaccgacct gtccggtgcc ctgaatgaac tgcaagacga ggcagcgcgg  12540

ctatcgtggc tggccacgac gggcgttcct tgcgcagctg tgctcgacgt tgtcactgaa  12600

gcgggaaggg actggctgct attgggcgaa gtgccggggc aggatctcct gtcatctcac  12660
```

```
cttgctcctg ccgagaaagt atccatcatg gctgatgcaa tgcggcggct gcatacgctt  12720

gatccggcta cctgcccatt cgaccaccaa gcgaaacatc gcatcgagcg agcacgtact  12780

cggatggaag ccggtcttgt cgatcaggat gatctggacg aagagcatca ggggctcgcg  12840

ccagccgaac tgttcgccag gctcaaggcg agcatgcccg acggcgagga tctcgtcgtg  12900

acccatggcg atgcctgctt gccgaatatc atggtggaaa atggccgctt ttctggattc  12960

atcgactgtg gccggctggg tgtggcggac cgctatcagg acatagcgtt ggctacccgt  13020

gatattgctg aagagcttgg cggcgaatgg gctgaccgct tcctcgtgct ttacggtatc  13080

gccgctcccg attcgcagcg catcgccttc tatcgccttc ttgacgagtt cttctgaatt  13140

ttgttaaaat tttgttaaa tcagctcatt ttttaaccaa taggccgaaa tcggcaaaat  13200

cccttataaa tcaaaagaat agaccgagat agggttgagt gttgttccag tttggaacaa  13260

gagtccacta ttaaagaacg tggactccaa cgtcaaaggg cgaaaaaccg tctatcaggg  13320

cgatggccca ctacgtgaac catcacccta atcaagtttt ttggggtcga ggtgccgtaa  13380

agcactaaat cggaacccta aagggagccc ccgatttaga gcttgacggg gaaagccggc  13440

gaacgtggcg agaaaggaag ggaagaaagc gaaaggagcg ggcgctaggg cgctggcaag  13500

tgtagcggtc acgctgcgcg taaccaccac acccgccgcg cttaatgcgc cgctacaggg  13560

cgcgtccatt cgccattcag gatcgaatta attcttaatt aa                    13602
```

```
<210> SEQ ID NO 2
<211> LENGTH: 575
<212> TYPE: PRT
<213> ORGANISM: Homo sapiens

<400> SEQUENCE: 2

Met Leu Gly Val Leu Val Leu Gly Ala Leu Ala Leu Ala Gly Leu Gly
1               5                   10                  15

Phe Pro Ala Pro Ala Glu Pro Gln Pro Gly Gly Ser Gln Cys Val Glu
            20                  25                  30

His Asp Cys Phe Ala Leu Tyr Pro Gly Pro Ala Thr Phe Leu Asn Ala
        35                  40                  45

Ser Gln Ile Cys Asp Gly Leu Arg Gly His Leu Met Thr Val Arg Ser
    50                  55                  60

Ser Val Ala Ala Asp Val Ile Ser Leu Leu Leu Asn Gly Asp Gly Gly
65                  70                  75                  80

Val Gly Arg Arg Arg Leu Trp Ile Gly Leu Gln Leu Pro Pro Gly Cys
                85                  90                  95

Gly Asp Pro Lys Arg Leu Gly Pro Leu Arg Gly Phe Gln Trp Val Thr
            100                 105                 110

Gly Asp Asn Asn Thr Ser Tyr Ser Arg Trp Ala Arg Leu Asp Leu Asn
        115                 120                 125

Gly Ala Pro Leu Cys Gly Pro Leu Cys Val Ala Val Ser Ala Ala Glu
    130                 135                 140

Ala Thr Val Pro Ser Glu Pro Ile Trp Glu Glu Gln Gln Cys Glu Val
145                 150                 155                 160

Lys Ala Asp Gly Phe Leu Cys Glu Phe His Phe Pro Ala Thr Cys Arg
                165                 170                 175

Pro Leu Ala Val Glu Pro Gly Ala Ala Ala Ala Ala Val Ser Ile Thr
            180                 185                 190

Tyr Gly Thr Pro Phe Ala Ala Arg Gly Ala Asp Phe Gln Ala Leu Pro
        195                 200                 205

Val Gly Ser Ser Ala Ala Val Ala Pro Leu Gly Leu Gln Leu Met Cys
```

```
    210                 215                 220

Thr Ala Pro Pro Gly Ala Val Gln Gly His Trp Ala Arg Glu Ala Pro
225                 230                 235                 240

Gly Ala Trp Asp Cys Ser Val Glu Asn Gly Gly Cys Glu His Ala Cys
                245                 250                 255

Asn Ala Ile Pro Gly Ala Pro Arg Cys Gln Cys Pro Ala Gly Ala Ala
            260                 265                 270

Leu Gln Ala Asp Gly Arg Ser Cys Thr Ala Ser Ala Thr Gln Ser Cys
        275                 280                 285

Asn Asp Leu Cys Glu His Phe Cys Val Pro Asn Pro Asp Gln Pro Gly
    290                 295                 300

Ser Tyr Ser Cys Met Cys Glu Thr Gly Tyr Arg Leu Ala Ala Asp Gln
305                 310                 315                 320

His Arg Cys Glu Asp Val Asp Asp Cys Ile Leu Glu Pro Ser Pro Cys
                325                 330                 335

Pro Gln Arg Cys Val Asn Thr Gln Gly Gly Phe Glu Cys His Cys Tyr
            340                 345                 350

Pro Asn Tyr Asp Leu Val Asp Gly Glu Cys Val Glu Pro Val Asp Pro
        355                 360                 365

Cys Phe Arg Ala Asn Cys Glu Tyr Gln Cys Gln Pro Leu Asn Gln Thr
    370                 375                 380

Ser Tyr Leu Cys Val Cys Ala Glu Gly Phe Ala Pro Ile Pro His Glu
385                 390                 395                 400

Pro His Arg Cys Gln Met Phe Cys Asn Gln Thr Ala Cys Pro Ala Asp
                405                 410                 415

Cys Asp Pro Asn Thr Gln Ala Ser Cys Glu Cys Pro Glu Gly Tyr Ile
            420                 425                 430

Leu Asp Asp Gly Phe Ile Cys Thr Asp Ile Asp Glu Cys Glu Asn Gly
        435                 440                 445

Gly Phe Cys Ser Gly Val Cys His Asn Leu Pro Gly Thr Phe Glu Cys
    450                 455                 460

Ile Cys Gly Pro Asp Ser Ala Leu Ala Arg His Ile Gly Thr Asp Cys
465                 470                 475                 480

Asp Ser Gly Lys Val Asp Gly Gly Asp Ser Gly Ser Gly Glu Pro Pro
                485                 490                 495

Pro Ser Pro Thr Pro Gly Ser Thr Leu Thr Pro Pro Ala Val Gly Leu
            500                 505                 510

Val His Ser Gly Leu Leu Ile Gly Ile Ser Ile Ala Ser Leu Cys Leu
        515                 520                 525

Val Val Ala Leu Leu Ala Leu Leu Cys His Leu Arg Lys Lys Gln Gly
    530                 535                 540

Ala Ala Arg Ala Lys Met Glu Tyr Lys Cys Ala Ala Pro Ser Lys Glu
545                 550                 555                 560

Val Val Leu Gln His Val Arg Thr Glu Arg Thr Pro Gln Arg Leu
                565                 570                 575
```

```
<210> SEQ ID NO 3
<211> LENGTH: 1725
<212> TYPE: DNA
<213> ORGANISM: Homo sapiens

<400> SEQUENCE: 3

atgcttgggg tcctggtcct tggcgcgctg gccctggccg gcctggggtt ccccgcaccc      60

gcagagccgc agccgggtgg cagccagtgc gtcgagcacg actgcttcgc gctctacccg     120
```

-continued

```
ggccccgcga ccttcctcaa tgccagtcag atctgcgacg gactgcgggg ccacctaatg    180

acagtgcgct cctcggtggc tgccgatgtc atttccttgc tactgaacgg cgacggcggc    240

gttggccgcc ggcgcctctg gatcggcctg cagctgccac ccggctgcgg cgaccccaag    300

cgcctcgggc ccctgcgcgg cttccagtgg gttacgggag acaacaacac cagctatagc    360

aggtgggcac ggctcgacct caatggggct cccctctgcg gcccgttgtg cgtcgctgtc    420

tccgctgctg aggccactgt gcccagcgag ccgatctggg aggagcagca gtgcgaagtg    480

aaggccgatg gcttcctctg cgagttccac ttcccagcca cctgcaggcc actggctgtg    540

gagcccggcg ccgcggctgc cgccgtctcg atcacctacg gcaccccgtt cgcggcccgc    600

ggagcggact tccaggcgct gccggtgggc agctccgccg cggtggctcc cctcggctta    660

cagctaatgt gcaccgcgcc gcccggagcg gtccaggggc actgggccag ggaggcgccg    720

ggcgcttggg actgcagcgt ggagaacggc ggctgcgagc acgcgtgcaa tgcgatccct    780

ggggctcccc gctgccagtg cccagccggc gccgccctgc aggcagacgg gcgctcctgc    840

accgcatccg cgacgcagtc ctgcaacgac ctctgcgagc acttctgcgt tcccaacccc    900

gaccagccgg gctcctactc gtgcatgtgc gagaccggct accggctggc ggccgaccaa    960

caccggtgcg aggacgtgga tgactgcata ctggagccca gtccgtgtcc gcagcgctgt   1020

gtcaacacac agggtggctt cgagtgccac tgctacccta actacgacct ggtggacggc   1080

gagtgtgtgg agcccgtgga cccgtgcttc agagccaact gcgagtacca gtgccagccc   1140

ctgaaccaaa ctagctacct ctgcgtctgc gccgagggct tcgcgcccat tccccacgag   1200

ccgcacaggt gccagatgtt ttgcaaccag actgcctgtc cagccgactg cgaccccaac   1260

acccaggcta gctgtgagtg ccctgaaggc tacatcctgg acgacggttt catctgcacg   1320

gacatcgacg agtgcgaaaa cggcggcttc tgctccgggg tgtgccacaa cctccccggt   1380

accttcgagt gcatctgcgg gcccgactcg gcccttgccc gccacattgg caccgactgt   1440

gactccggca aggtggacgg tggcgacagc ggctctggcg agcccccgcc cagcccgacg   1500

cccggctcca ccttgactcc tccggccgtg gggctcgtgc attcgggctt gctcataggc   1560

atctccatcg cgagcctgtg cctggtggtg gcgcttttgg cgctcctctg ccacctgcgc   1620

aagaagcagg gcgccgccag ggccaagatg gagtacaagt gcgcggcccc ttccaaggag   1680

gtagtgctgc agcacgtgcg gaccgagcgg acgccgcaga gactc                   1725
```

```
<210> SEQ ID NO 4
<211> LENGTH: 649
<212> TYPE: DNA
<213> ORGANISM: Homo sapiens
<220> FEATURE:
<221> NAME/KEY: modified_base
<222> LOCATION: (335)..(335)
<223> OTHER INFORMATION: a, c, g, t, unknown or other
<220> FEATURE:
<221> NAME/KEY: misc_feature
<222> LOCATION: (335)..(335)
<223> OTHER INFORMATION: n is a, c, g, or t

<400> SEQUENCE: 4

tctagacgcg ttgacattga ttattgacta gttattaata gtaatcaatt acggggtcat     60

tagttcatag cccatgatat catatggagt tccgcgttac ataacttacg gtaaatggcc    120

cgcctggctg accgcccaac gacccccgcc cattgacgtc aataatgacg tatgttccca    180

tagtaacgcc aatagggact ttccattgac gtcaatgggt ggagtattta cggtaaactg    240

cccacttggc agtacatcaa gtgtatcata tgccaagtac gccccctat tgacgtcaat    300
```

-continued

```
gacggtaaat ggcccgcctg gcattatgcc cagtncatga ccttatggga ctttcctact    360

tggcagacat ctacgtatta gtcatcgcta ttaccatggt gatgcggttt tggcagtaca    420

tcaatgggcg tggatagcgg tttgactcac ggggatttc caagtctcca ccccattgac    480

gtcaatggga gtttgttttg gcaccaaaat caacgggact ttccaaaatg tcgtaacaac    540

tccgccccat tgacgcaaat gggcggtagg cgtgtacggt gggaggtcta tataagcaga    600

gctctctggc taactagaga acccctgctt actggcttat cgagatatc                649


<210> SEQ ID NO 5
<211> LENGTH: 3693
<212> TYPE: DNA
<213> ORGANISM: Homo sapiens

<400> SEQUENCE: 5

ggcagcgcgc agcggcaaga agtgtctggg ctgggacgga caggagaggc tgtcgccatc     60

ggcgtcctgt gcccctctgc tccggcacgg ccctgtcgca gtgcccgcgc tttccccggc    120

gcctgcacgc ggcgcgcctg ggtaacatgc ttggggtcct ggtccttggc gcgctggccc    180

tggccggcct ggggttcccc gcacccgcag agccgcagcc gggtggcagc cagtgcgtcg    240

agcacgactg cttcgcgctc tacccgggcc ccgcgacctt cctcaatgcc agtcagatct    300

gcgacggact gcggggccac ctaatgacag tgcgctcctc ggtggctgcc gatgtcattt    360

ccttgctact gaacggcgac ggcggcgttg gccgccggcg cctctggatc ggcctgcagc    420

tgccacccgg ctgcggcgac cccaagcgcc tcgggcccct gcgcggcttc cagtgggtta    480

cgggagacaa caacaccagc tatagcaggt gggcacggct cgacctcaat ggggctcccc    540

tctgcggccc gttgtgcgtc gctgtctccg ctgctgaggc cactgtgccc agcgagccga    600

tctgggagga gcagcagtgc gaagtgaagg ccgatggctt cctctgcgag ttccacttcc    660

cagccacctg caggccactg gctgtggagc ccggcgccgc ggctgccgcc gtctcgatca    720

cctacggcac cccgttcgcg gcccgcggag cggacttcca ggcgctgccg gtgggcagct    780

ccgccgcggt ggctcccctc ggcttacagc taatgtgcac cgcgccgccc ggagcggtcc    840

aggggcactg ggccagggag gcgccgggcg cttgggactg cagcgtggag aacggcggct    900

gcgagcacgc gtgcaatgcg atccctgggg ctccccgctg ccagtgccca gccggcgccg    960

ccctgcaggc agacgggcgc tcctgcaccg catccgcgac gcagtcctgc aacgacctct   1020

gcgagcactt ctgcgttccc aaccccgacc agccgggctc ctactcgtgc atgtgcgaga   1080

ccggctaccg gctggcggcc gaccaacacc ggtgcgagga cgtggatgac tgcatactgg   1140

agcccagtcc gtgtccgcag cgctgtgtca acacacaggg tggcttcgag tgccactgct   1200

accctaacta cgacctggtg gacggcgagt gtgtggagcc cgtggacccg tgcttcagag   1260

ccaactgcga gtaccagtgc cagcccctga accaaactag ctacctctgc gtctgcgccg   1320

agggcttcgc gcccattccc cacgagccgc acaggtgcca gatgttttgc aaccagactg   1380

cctgtccagc cgactgcgac cccaacaccc aggctagctg tgagtgccct gaaggctaca   1440

tcctggacga cggtttcatc tgcacggaca tcgacgagtg cgaaaacggc ggcttctgct   1500

ccggggtgtg ccacaacctc cccggtacct tcgagtgcat ctgcgggccc gactcggccc   1560

ttgcccgcca cattggcacc gactgtgact ccggcaaggt ggacggtggc gacagcggct   1620

ctggcgagcc cccgcccagc ccgacgcccg gctccacctt gactcctccg gccgtggggc   1680

tcgtgcattc gggcttgctc ataggcatct ccatcgcgag cctgtgcctg gtggtggcgc   1740

ttttggcgct cctctgccac ctgcgcaaga agcagggcgc cgccagggcc aagatggagt   1800
```

acaagtgcgc ggccccttcc aaggaggtag tgctgcagca cgtgcggacc gagcggacgc 1860
cgcagagact ctgagcggcc tccgtccagg agcctggctc cgtccaggag cctgtgcctc 1920
ctcaccccca gctttgctac caaagcacct tagctggcat tacagctgga gaagaccctc 1980
cccgcacccc ccaagctgtt ttcttctatt ccatggctaa ctggcgaggg ggtgattaga 2040
gggaggagaa tgagcctcgg cctcttccgt gacgtcactg gaccactggg caatgatggc 2100
aattttgtaa cgaagacaca gactgcgatt tgtcccaggt cctcactacc gggcgcagga 2160
gggtgagcgt tattggtcgg cagccttctg ggcagacctt gacctcgtgg gctagggatg 2220
actaaaatat ttattttttt taagtattta ggtttttgtt tgtttccttt gttcttacct 2280
gtatgtctcc agtatccact ttgcacagct ctccggtctc tctctctcta caaactccca 2340
cttgtcatgt gacaggtaaa ctatcttggt gaattttttt ttcctagccc tctcacattt 2400
atgaagcaag ccccacttat tccccattct tcctagtttt ctcctcccag gaactgggcc 2460
aactcacctg agtcacccta cctgtgcctg accctacttc ttttgctctt agctgtctgc 2520
tcagacagaa cccctacatg aaacagaaac aaaaacacta aaaataaaaa tggccatttg 2580
ctttttcacc agatttgcta atttatcctg aaatttcaga ttcccagagc aaaataattt 2640
taaacaaagg ttgagatgta aaaggtatta aattgatgtt gctggactgt catagaaatt 2700
acacccaaag aggtatttat ctttactttt aaacagtgag cctgaatttt gttgctgttt 2760
tgatttgtac tgaaaaatgg taattgttgc taatcttctt atgcaatttc cttttttgtt 2820
attattactt atttttgaca gtgttgaaaa tgttcagaag gttgctctag attgagagaa 2880
gagacaaaca cctcccagga gacagttcaa gaaagcttca aactgcatga ttcatgccaa 2940
ttagcaattg actgtcactg ttccttgtca ctggtagacc aaaataaaac cagctctact 3000
ggtcttgtgg aattgggagc ttgggaatgg atcctggagg atgcccaatt agggcctagc 3060
cttaatcagg tcctcagaga atttctacca tttcagagag gccttttgga atgtggcccc 3120
tgaacaagaa ttggaagctg ccctgcccat gggagctggt tagaaatgca gaatcctagg 3180
ctccacccca tccagttcat gagaatctat atttaacaag atctgcaggg ggtgtgtctg 3240
ctcagtaatt tgaggacaac cattccagac tgcttccaat ttctggaat acatgaaata 3300 tagatcagtt ataagtagca ggccaagtca ggcccttatt ttcaagaaac tgaggaattt 3360
tctttgtgta gctttgctct ttggtagaaa aggctaggta cacagctcta gacactgcca 3420
cacagggtct gcaaggtctt tggttcagct aagctaggaa tgaaatcctg cttcagtgta 3480
tggaaataaa tgtatcatag aaatgtaact tttgtaagac aaaggttttc ctcttctatt 3540
ttgtaaactc aaaatatttg tacatagtta tttatttatt ggagataatc tagaacacag 3600
gcaaaatcct tgcttatgac atcacttgta caaaataaac aaataacaat gtgaaaaaaa 3660
aaaaaaaaaa aaaaaaaaaa aaaaaaaaaa aaa 3693

<210> SEQ ID NO 6
<211> LENGTH: 4457
<212> TYPE: DNA
<213> ORGANISM: Homo sapiens
<220> FEATURE:
<221> NAME/KEY: modified_base
<222> LOCATION: (349)..(349)
<223> OTHER INFORMATION: a, c, g, t, unknown or other
<220> FEATURE:
<221> NAME/KEY: misc_feature
<222> LOCATION: (349)..(349)
<223> OTHER INFORMATION: n is a, c, g, or t

<400> SEQUENCE: 6

```
gtttaaacgg gccctctaga cgcgttgaca ttgattattg actagttatt aatagtaatc     60
aattacgggg tcattagttc atagcccatg atatcatatg gagttccgcg ttacataact    120
tacggtaaat ggcccgcctg gctgaccgcc caacgacccc cgcccattga cgtcaataat    180
gacgtatgtt cccatagtaa cgccaatagg gactttccat tgacgtcaat gggtggagta    240
tttacggtaa actgcccact tggcagtaca tcaagtgtat catatgccaa gtacgccccc    300
ctattgacgt caatgacggt aaatggcccg cctggcatta tgcccagtnc atgaccttat    360
gggactttcc tacttggcag acatctacgt attagtcatc gctattacca tggtgatgcg    420
gttttggcag tacatcaatg ggcgtggata gcggtttgac tcacggggat ttccaagtc     480
tccaccccat tgacgtcaat gggagtttgt tttggcacca aaatcaacgg gactttccaa    540
aatgtcgtaa caactccgcc ccattgacgc aaatgggcgg taggcgtgta cggtgggagg    600
tctatataag cagagctctc tggctaacta gagaacccct gcttactggc ttatcgagat    660
atctgcagaa ttcatctgtc gactgctacc ggcagcgcgc agcggcaaga agtgtctggg    720
ctgggacgga caggagaggc tgtcgccatc ggcgtcctgt gcccctctgc tccggcacgg    780
ccctgtcgca gtgcccgcgc tttccccggc gcctgcacgc ggcgcgcctg ggtaacatgc    840
ttggggtcct ggtccttggc gcgctggccc tggccggcct ggggttcccc gcacccgcag    900
agccgcagcc gggtggcagc cagtgcgtcg agcacgactg cttcgcgctc tacccgggcc    960
ccgcgacctt cctcaatgcc agtcagatct gcgacggact gcggggccac ctaatgacag   1020
tgcgctcctc ggtggctgcc gatgtcattt ccttgctact gaacggcgac ggcggcgttg   1080
gccgccggcg cctctggatc ggcctgcagc tgccacccgg ctgcggcgac cccaagcgcc   1140
tcgggcccct gcgcggcttc cagtgggtta cgggagacaa caacaccagc tatagcaggt   1200
gggcacggct cgacctcaat ggggctcccc tctgcggccc gttgtgcgtc gctgtctccg   1260
ctgctgaggc cactgtgccc agcgagccga tctgggagga gcagcagtgc gaagtgaagg   1320
ccgatggctt cctctgcgag ttccacttcc cagccacctg caggccactg gctgtggagc   1380
ccggcgccgc ggctgccgcc gtctcgatca cctacggcac cccgttcgcg gcccgcggag   1440
cggacttcca ggcgctgccg gtgggcagct ccgccgcggt ggctcccctc ggcttacagc   1500
taatgtgcac cgcgccgccc ggagcggtcc aggggcactg ggccagggag gcgccgggcg   1560
cttgggactg cagcgtggag aacggcggct gcgagcacgc gtgcaatgcg atccctgggg   1620
ctccccgctg ccagtgccca gccggcgccg ccctgcaggc agacgggcgc tcctgcaccg   1680
catccgcgac gcagtcctgc aacgacctct gcgagcactt ctgcgttccc aaccccgacc   1740
agccgggctc ctactcgtgc atgtgcgaga ccggctaccg gctggcggcc gaccaacacc   1800
ggtgcgagga cgtggatgac tgcatactgg agcccagtcc gtgtccgcag cgctgtgtca   1860
acacacaggg tggcttcgag tgccactgct accctaacta cgacctggtg gacggcgagt   1920
gtgtggagcc cgtggacccg tgcttcagag ccaactgcga gtaccagtgc cagcccctga   1980
accaaactag ctacctctgc gtctgcgccg agggcttcgc gcccattccc cacgagccgc   2040
acaggtgcca gatgttttgc aaccagactg cctgtccagc cgactgcgac cccaacaccc   2100
aggctagctg tgagtgccct gaaggctaca tcctggacga cggtttcatc tgcacggaca   2160
tcgacgagtg cgaaaacggc ggcttctgct ccggggtgtg ccacaacctc cccggtacct   2220
tcgagtgcat ctgcgggccc gactcggccc ttgcccgcca cattggcacc gactgtgact   2280
ccggcaaggt ggacggtggc gacagcggct ctggcgagcc cccgcccagc ccgacgcccg   2340
gctccacctt gactcctccg gccgtggggc tcgtgcattc gggcttgctc ataggcatct   2400
```

```
ccatcgcgag cctgtgcctg gtggtggcgc ttttggcgct cctctgccac ctgcgcaaga   2460

agcagggcgc cgccagggcc aagatggagt acaagtgcgc ggccccttcc aaggaggtag   2520

tgctgcagca cgtgcggacc gagcggacgc cgcagagact ctgagcggcc tccgtccagg   2580

agcctggctc cgtccaggag cctgtgcctc ctcacccccca gctttgctac caaagcacct   2640

tagctggcat tacagctgga gaagaccctc cccgcacccc ccaagctgtt ttcttctatt   2700

ccatggctaa ctggcgaggg ggtgattaga gggaggagaa tgagcctcgg cctcttccgt   2760

gacgtcactg gaccactggg caatgatggc aattttgtaa cgaagacaca gactgcgatt   2820

tgtcccaggt cctcactacc gggcgcagga gggtgagcgt tattggtcgg cagccttctg   2880

ggcagacctt gacctcgtgg gctagggatg actaaaatat ttattttttt taagtattta   2940

ggtttttgtt tgtttccttt gttcttacct gtatgtctcc agtatccact ttgcacagct   3000

ctccggtctc tctctctcta caaactccca cttgtcatgt gacaggtaaa ctatcttggt   3060

gaattttttt ttcctagccc tctcacattt atgaagcaag ccccacttat tccccattct   3120

tcctagtttt ctcctcccag gaactgggcc aactcacctg agtcacccta cctgtgcctg   3180

accctacttc ttttgctctt agctgtctgc tcagacagaa cccctacatg aaacagaaac   3240

aaaaacacta aaaataaaaa tggccatttg ctttttcacc agatttgcta atttatcctg   3300

aaatttcaga ttcccagagc aaaataattt taaacaaagg ttgagatgta aaaggtatta   3360

aattgatgtt gctggactgt catagaaatt acacccaaag aggtatttat ctttactttt   3420

aaacagtgag cctgaatttt gttgctgttt tgatttgtac tgaaaaatgg taattgttgc   3480

taatcttctt atgcaatttc ctttttttgtt attattactt atttttgaca gtgttgaaaa   3540

tgttcagaag gttgctctag attgagagaa gagacaaaca cctcccagga gacagttcaa   3600

gaaagcttca aactgcatga ttcatgccaa ttagcaattg actgtcactg ttccttgtca   3660

ctggtagacc aaaataaaac cagctctact ggtcttgtgg aattgggagc ttgggaatgg   3720

atcctggagg atgcccaatt agggcctagc cttaatcagg tcctcagaga atttctacca   3780

tttcagagag gccttttgga atgtggcccc tgaacaagaa ttggaagctg ccctgcccat   3840

gggagctggt tagaaatgca gaatcctagg ctccacccca tccagttcat gagaatctat   3900

atttaacaag atctgcaggg ggtgtgtctg ctcagtaatt tgaggacaac cattccagac   3960

tgcttccaat tttctggaat acatgaaata tagatcagtt ataagtagca ggccaagtca   4020

ggcccttatt ttcaagaaac tgaggaattt tctttgtgta gctttgctct ttggtagaaa   4080

aggctaggta cacagctcta gacactgcca cacagggtct gcaaggtctt tggttcagct   4140

aagctaggaa tgaaatcctg cttcagtgta tggaaataaa tgtatcatag aaatgtaact   4200

tttgtaagac aaaggttttc ctcttctatt ttgtaaactc aaaatatttg tacatagtta   4260

tttatttatt ggagataatc tagaacacag gcaaaatcct tgcttatgac atcacttgta   4320

caaaataaac aaataacaat gtgaaaaaaa aaaaaaaaaa aaaaaaaaaa aaaaaaaaaa   4380

aaaggtagca gtcgacagat gaattccacc acactggact agtggatccg agctcggtac   4440

caagcttaag tttaaac                                                 4457
```

```
<210> SEQ ID NO 7
<211> LENGTH: 17534
<212> TYPE: DNA
<213> ORGANISM: Artificial Sequence
<220> FEATURE:
<223> OTHER INFORMATION: Description of Artificial Sequence: Synthetic
      plasmid
<220> FEATURE:
<221> NAME/KEY: modified_base
```

```
<222> LOCATION: (730)..(730)
<223> OTHER INFORMATION: a, c, g, t, unknown or other
<220> FEATURE:
<221> NAME/KEY: misc_feature
<222> LOCATION: (730)..(730)
<223> OTHER INFORMATION: n is a, c, g, or t

<400> SEQUENCE: 7

catcatcaat aatatacctt attttggatt gaagccaata tgataatgag gggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tactggtacc gcggccgcct    360

cgagtctaga actagtggat cccccaaacg ggccctctag acgcgttgac attgattatt    420

gactagttat taatagtaat caattacggg gtcattagtt catagcccat gatatcatat    480

ggagttccgc gttacataac ttacggtaaa tggcccgcct ggctgaccgc ccaacgaccc    540

ccgcccattg acgtcaataa tgacgtatgt tcccatagta acgccaatag ggactttcca    600

ttgacgtcaa tgggtggagt atttacggta aactgcccac ttggcagtac atcaagtgta    660

tcatatgcca agtacgcccc ctattgacg tcaatgacgg taaatggccc gcctggcatt    720

atgcccagtn catgacctta tgggactttc ctacttggca gacatctacg tattagtcat    780

cgctattacc atggtgatgc ggttttggca gtacatcaat gggcgtggat agcggtttga    840

ctcacgggga tttccaagt ctccacccca ttgacgtcaa tgggagtttg ttttggcacc    900

aaaatcaacg ggactttcca aaatgtcgta acaactccgc cccattgacg caaatgggcg    960

gtaggcgtgt acggtgggag gtctatataa gcagagctct ctggctaact agagaacccc   1020

tgcttactgg cttatcgaga tatctgcaga attcatctgt cgactgctac cggcagcgcg   1080

cagcggcaag aagtgtctgg gctgggacgg acaggagagg ctgtcgccat cggcgtcctg   1140

tgcccctctg ctccggcacg gccctgtcgc agtgcccgcg ctttccccgg cgcctgcacg   1200

cggcgcgcct gggtaacatg cttggggtcc tggtccttgg cgcgctggcc ctggccggcc   1260

tggggttccc cgcacccgca gagccgcagc cgggtggcag ccagtgcgtc gagcacgact   1320

gcttcgcgct ctacccgggc cccgcgacct tcctcaatgc cagtcagatc tgcgacggac   1380

tgcggggcca cctaatgaca gtgcgctcct cggtggctgc cgatgtcatt tccttgctac   1440

tgaacggcga cggcggcgtt ggccgccggc gcctctggat cggcctgcag ctgccacccg   1500

gctgcggcga ccccaagcgc ctcgggcccc tgcgcggctt ccagtgggtt acgggagaca   1560

acaacaccag ctatagcagg tgggcacggc tcgacctcaa tggggctccc ctctgcggcc   1620

cgttgtgcgt cgctgtctcc gctgctgagg ccactgtgcc cagcgagccg atctgggagg   1680

agcagcagtg cgaagtgaag gccgatggct tcctctgcga gttccacttc ccagccacct   1740

gcaggccact ggctgtggag cccggcgccg cggctgccgc cgtctcgatc acctacggca   1800

ccccgttcgc ggcccgcgga gcggacttcc aggcgctgcc ggtgggcagc tccgccgcgg   1860

tggctcccct cggcttacag ctaatgtgca ccgcgccgcc cggagcggtc caggggcact   1920

gggccaggga ggcgccgggc gcttgggact gcagcgtgga gaacggcggc tgcgagcacg   1980

cgtgcaatgc gatccctggg gctccccgct gccagtgccc agccggcgcc gccctgcagg   2040

cagacgggcg ctcctgcacc gcatccgcga cgcagtcctg caacgacctc tgcgagcact   2100

tctgcgttcc caaccccgac cagccgggct cctactcgtg catgtgcgag accggctacc   2160
```

-continued

```
ggctggcggc cgaccaacac cggtgcgagg acgtggatga ctgcatactg gagcccagtc   2220
cgtgtccgca gcgctgtgtc aacacacagg gtggcttcga gtgccactgc taccctaact   2280
acgacctggt ggacggcgag tgtgtggagc ccgtggaccc gtgcttcaga gccaactgcg   2340
agtaccagtg ccagcccctg aaccaaacta gctacctctg cgtctgcgcc gagggcttcg   2400
cgcccattcc ccacgagccg cacaggtgcc agatgttttg caaccagact gcctgtccag   2460
ccgactgcga ccccaacacc caggctagct gtgagtgccc tgaaggctac atcctggacg   2520
acggtttcat ctgcacggac atcgacgagt gcgaaaacgg cggcttctgc tccggggtgt   2580
gccacaacct ccccggtacc ttcgagtgca tctgcgggcc cgactcggcc cttgcccgcc   2640
acattggcac cgactgtgac tccggcaagg tggacggtgg cgacagcggc tctggcgagc   2700
ccccgcccag cccgacgccc ggctccacct tgactcctcc ggccgtgggg ctcgtgcatt   2760
cgggcttgct cataggcatc tccatcgcga gcctgtgcct ggtggtggcg cttttggcgc   2820
tcctctgcca cctgcgcaag aagcagggcg ccgccagggc caagatggag tacaagtgcg   2880
cggccccttc caaggaggta gtgctgcagc acgtgcggac cgagcggacg ccgcagagac   2940
tctgagcggc ctccgtccag gagcctggct ccgtccagga gcctgtgcct cctcaccccc   3000
agctttgcta ccaaagcacc ttagctggca ttacagctgg agaagaccct ccccgcaccc   3060
cccaagctgt ttcttctat tccatggcta actggcgagg gggtgattag agggaggaga   3120
atgagcctcg gcctcttccg tgacgtcact ggaccactgg gcaatgatgg caattttgta   3180
acgaagacac agactgcgat ttgtcccagg tcctcactac cgggcgcagg agggtgagcg   3240
ttattggtcg gcagccttct gggcagacct tgacctcgtg ggctagggat gactaaaata   3300
tttattttt ttaagtattt aggtttttgt ttgtttcctt tgttcttacc tgtatgtctc   3360
cagtatccac tttgcacagc tctccggtct ctctctctct acaaactccc acttgtcatg   3420
tgacaggtaa actatcttgg tgaatttttt tttcctagcc ctctcacatt tatgaagcaa   3480
gccccactta ttccccattc ttcctagttt tctcctccca ggaactgggc caactcacct   3540
gagtcaccct acctgtgcct gaccctactt cttttgctct tagctgtctg ctcagacaga   3600
accccctacat gaaacagaaa caaaaacact aaaaataaaa atggccattt gctttttcac   3660
cagatttgct aatttatcct gaaatttcag attcccagag caaaataatt ttaaacaaag   3720
gttgagatgt aaaaggtatt aaattgatgt tgctggactg tcatagaaat tacacccaaa   3780
gaggtattta tctttacttt taaacagtga gcctgaattt tgttgctgtt ttgatttgta   3840
ctgaaaaatg gtaattgttg ctaatcttct tatgcaattt cctttttgt tattattact   3900
tatttttgac agtgttgaaa atgttcagaa ggttgctcta gattgagaga agagacaaac   3960
acctcccagg agacagttca agaaagcttc aaactgcatg attcatgcca attagcaatt   4020
gactgtcact gttccttgtc actggtagac caaaataaaa ccagctctac tggtcttgtg   4080
gaattgggag cttgggaatg gatcctggag gatgcccaat tagggcctag ccttaatcag   4140
gtcctcagag aatttctacc atttcagaga ggccttttgg aatgtggccc ctgaacaaga   4200
attggaagct gccctgccca tgggagctgg ttagaaatgc agaatcctag gctccacccc   4260
atccagttca tgagaatcta tatttaacaa gatctgcagg gggtgtgtct gctcagtaat   4320
ttgaggacaa ccattccaga ctgcttccaa ttttctggaa tacatgaaat atagatcagt   4380
tataagtagc aggccaagtc aggcccttat tttcaagaaa ctgaggaatt ttctttgtgt   4440
agctttgctc tttggtagaa aaggctaggt acacagctct agacactgcc acacagggtc   4500
tgcaaggtct ttggttcagc taagctagga atgaaatcct gcttcagtgt atggaaataa   4560
```

```
atgtatcata gaaatgtaac ttttgtaaga caaaggtttt cctcttctat tttgtaaact   4620
caaaatattt gtacatagtt atttatttat tggagataat ctagaacaca ggcaaaatcc   4680
ttgcttatga catcacttgt acaaaataaa caaataacaa tgtgaaaaaa aaaaaaaaaa   4740
aaaaaaaaaa aaaaaaaaaa aaaaggtagc agtcgacaga tgaattccac cacactggac   4800
tagtggatcc gagctcggta ccaagcttaa gtttgggctg caggaattct gatggctctc   4860
aaaattcctg cctcctttag ggataaaaga ctttaagact ttttaacaaa aaagaaaaag   4920
aaaaaaaaaa ttcctgcctc ctggtgtaca cacacagaag ggttccctcc ccttgaatgt   4980
gaccaggatc tgtgaaaata acgggatagc cgctcctgtg attaggttat gtggtagact   5040
agagcaagat tctcctgctg gttttgaaga agtcagctgc catgttgtga gactgtcatg   5100
ggctagggca tgagccttta aatatctggg agcaacccct ggccagcagc cagtgagaaa   5160
acgggccctc agtcctacaa tcacaaggaa ctaaattctg ccaacaacct gaaggaactt   5220
tgaagaggat catgagtccc ttgattcagc ttgatgagcc cctgagcaga ggatacagct   5280
aacttgtact agggaagtat aaaaaacatg catgggaatg atatatatca actttaagga   5340
taattgtcat acttctggga atgaagggaa agaaatgggg ctttagttgt attatgatct   5400
ttaatttctc aaaaaaaata agatcagaag caaatatggc aaaatgttaa tacttttgtg   5460
ggtacgtagg tattcagcat accctttttt ctgagttcaa aatattttat aattaaaatg   5520
aaatgcaggc caggcacagt ggctcatgcc tataatacca gcactttgcg aggccgaggt   5580
gggaggatgg cttgaggcca gaccagcctg gccaacatgg caaaacccca tctctactta   5640
aaaaaaaaaa aactatatat atatatatgt gtgtgtgtgt gtatatatat atatgtatat   5700
atatttatat atgtgtgtat atatatatat gtatatatat ttatatatgt gtgtgtatat   5760
atatatatac acacacacac atatatacat acatacatac acacacacac acacacaatt   5820
agccaggcat ggtggcgcac acctgtagtc ccagctactt gggaggctga gacatgagaa   5880
ttgcttgaac ctgggaggca gagtagttag tgagctgaga tcataccact gcactccagc   5940
ctggtgacag agtgagactc tgtcttaaaa aaaataaaaa ttaaaattaa atgcaaaagg   6000
tccaagtgaa ttgaagagga aaggggtatc aaggaaggtt ttgtggaggt gacgtttgag   6060
ctgggtctta aatgacttaa acatgggata agaagggagg gaataaggac atttcaggta   6120
cgagaaataa ggagcaaaca gtggaaacaa cctaacgtct gtcaaccagt gaatggataa   6180
caaaaatgta attcagatgg tatccaactt acgatggttc aacatgagat ttttctgact   6240
ttaggataga tttatcaaag tagtaaatcc attttcaact tatgatattt tcaacttcag   6300
atgggtttat caggacacag ttgaggaaca cctgtctatc catacaattt ggcaataaaa   6360
aggaaatgag tgcagatata ctccacaaca tgaatgaacc ttgaaaacat taagtgagag   6420
aagccagata caaaaggcca catattgtat gattctattt atacaaaatg tccagaatag   6480
gcaaatctta tagacagcaa gtaggtagat gatcagtttg ctaggtgctg gggaagggg   6540
aaatggggag tgatggctaa ggggattggg tttctttgtg gggcaatgaa aatgttttaa   6600
aattgagcgt gataatgatt gcacaatgct gcatatatat ataatctata gattatatat   6660
atataaagag aggctgttag acagtgataa gtgatatata tatatatata catagagaga   6720
gagagagaga gagagagagg ctgttagtga taagtgatca ggaaaataaa agtattgagg   6780
aggaatacga agttgacggt gtgaaaacat gagattttat ataggatggc cagggaaggc   6840
cttaatgaga aagtgactta tgagtaaaaa caagggatcc taaaccttag catgcatcag   6900
aatcactcgg aaacttgtta aagcatagct tgctgggcct catcacagat attttgattc   6960
```

```
ggtaggttct tgtctgatat taatactttt ggtctaggga accacatttt gagaaccact   7020
gagctaaagg aagtaaaggt ttcccttagt ttactagctg gtaacactgg cccaggaggc   7080
ctttctggtg acccctaagg aattatccaa actcttgttt ttagatgctt tattatatca   7140
aactctcctt taaacaagtg gcccatctgc tgggatttgg aagcctgtaa tactgaaatt   7200
ttcatcataa tggaaatttt aaaaacagaa tttgacccac ctgtttttaa aacactttca   7260
ttacttaaca agaggtctaa tcttgggcaa gtcttgaaat ttctctggcc ttagtttccc   7320
atgtgttaaa tgaaacttga agcagttggt ctcttatagt ctcctgactc taacattcta   7380
agaattatat ttgtacaata actcaaaaat cacataattt aatttaccat atggactcca   7440
aaatatattt tctcattagg ctaaacttga tctgcatttt ctggatgtgt ccatattctt   7500
ggactacact aaaacatgat accaatgctt cctctcacca taaaccctca cttcgctttc   7560
tacatttaag aattttatag ctggaagagt ccttaacaga aaataccatc taataattac   7620
ccctcaaaat cgagaaagtc ctatctgttc ttatgctagt tataagaatg aggcagcatt   7680
tcacataatg gttataaaca ctgccacaag aagattcatg atgtgttgtt tatctgtagc   7740
tctcatcata ctctgtcata taactatagc attaagattt taatgttcta tatattcttc   7800
taagacagtg tttaccagag taaggcacaa aagatccact ggtttgcaag aaagattaga   7860
acttttaaat tttttacctc accttgttta atctatattt ttgtatgtat tttgtaacat   7920
atatattatt attaccataa atcatatata atttaaaatg catatattag gggtaaatgc   7980
tcaggaaact ttttataaat tgggcatgca aatacaagtt tgaagactca ctgttctagg   8040
tattaaaagt aaagttataa ccaagtaaag cttccacctt ttcatgtctc aaagcagttt   8100
attgttggag gtaagatctc ttagaagcct aaacaggtcc aagtacagaa tgaagtaagg   8160
ctagcccata acttgtggca agcaattcat actatttctc tcatgctgag ctctcctcag   8220
tgaagcagct actatagaca actgcagcct attggtagcc tattttacag gcaggaaaaa   8280
aattactttt tattcaaagt ggaactcagg acatggggag aaaatgaata caaaaaatag   8340
ggtcaatcca aaggcacaca gcaaatgagt aacacagtta tgttttttttc ccatttgtat   8400
gaggtcccag taaattctaa gtaaactgca aatttaataa tacactaaaa aagccatgca   8460
attgttcaaa tgaatcccag catggtacaa ggagtacaga cactagagtc taaaaaacaa   8520
aagaatgcca ttattgagtt tttgaattat atcaagtagt tacatctcta cttaataaat   8580
gagaaaaacg aggataagag gccatttgat aaaatgaaaa tagccaagaa gtggtattag   8640
agacttgaat acaggtattc gggtccaaag ttcatctgct caaatactaa ctggggaaaa   8700
gagggaaaaa tatttatata catatatatc tgcacacaaa aatacccccca aaagacaaaa   8760
tgaggccagg cagggtggct cacacccgta atcccggtac tttgggaggc tgaggcaggt   8820
ggatacctga gatcaggagt tggagatcag cctggtcaac atggtgaaac cctgtctcta   8880
ctaaagataa aaaaattagc caggcatggt ggcgtgcgcc tgtaatccca gctacttggg   8940
agtctgaggc aggagaatca cttgaactgg gaaggggagg ttgcagtgag ccaagatcgt   9000
actactgcac tccagcctgg gcagcagagt gagactccat cacaaaaata aataaataaa   9060
taaaatacaa tgaaacagaa agttcaaata atcccataat cttaccacca agaaataact   9120
ttcactcgtt atacttattg atttttccat aataaatgta ctttactgtg actatcatga   9180
aaagaaagtt attttagaaa cagagaactg tttcagatca aatctatgta gtagaacaga   9240
gccattaggt gggaaagacg agatcaaact aaatctcaga aggcctaaaa ggctaggtcc   9300
attccagcac taaaaactga ccagacaagt aatggcttca acagcttcta aatatggaca   9360
```

```
aagcatgctg aaagggaagg acaggtctaa cagtggtata tgaaatgaac aggaggggca   9420
aagctcattt ctcctctgaa gttttccaaa gatgctgagg aggacattag tttgacatga   9480
ccctgatatg ggacaagata atttcacaga agttttacat gttaaagttt tcttatagat   9540
actcattcaa gtaagcaatg aacactaaaa tctaaagaaa gaaaagagct ttagagtcag   9600
gtctgtattc aaattcaagc tctaccactt actggttctg tgactttggg caagtctttt   9660
aaccttatta agtcttaatt tcctgatttg taaaatgggg atatcgtctc cctcacagga   9720
ttgttgtgaa acttttatga gattaatgcc tttatatttg gcatagtgta agtaaacaat   9780
aactggcagc ttcaaaaaaa aaaagcagta gcattccatc atttattatt ggttactctc   9840
aaaaagtttt tcaatgtact agaagataaa tattcaaata ccttaatatc tccattattt   9900
tcaggtaaac agcatgctcc tgaacaacca atgggtcaac aaataaatta aaagggaaat   9960
ctaaaaacat cttgatatta aactacatgg aagcacaata taccaaaacc aatggttcac  10020
actaggagaa ttttaaggta caagaaaact ctttgagatt tcttaaaata atagtatgtc  10080
tgaatttatt gagtgattta ccagaaactg ttgtaagagc tctacttgca ttatagcact  10140
taatcctctt aactctatgg ctgctattat caacctcacc ctaatcacat atgggacaca  10200
gagaggttaa gtaacttgcc caaggtcaga gttaggaagt actaagccat gctttgaatc  10260
agttgtcagg ctccggaact cacactttca gccactacat aatactgctt tgctatcttt  10320
taggaaacta tgtgagtcta cctcacatag actcacatag gtttgttttt tttttttttt  10380
taaaggctat cttttccccc atcaatgttt tttgaaggat cccaaattag agtcccacag  10440
aggcagacag cagtacttga caatatggac atttaaggtt aatgttggat tctactgtct  10500
ttttactaca tgacctaggg aacgataatt aacctagact gcttccaagg gttaaataac  10560
ccatttagtt atactatgta aattatctct tagtgattga ttgaaagcac actgttacta  10620
attgactcgg tatgaagtgc tttttttttct tccctttcaa gatacatacc tttccagtta  10680
aagttgagag atcatctcca ccaattactt ttatgtcccc tgttgactgg tcattctagt  10740
taaaaaaaaa aaaaactata tatatatata tctacacaca catatgtata tgtatatcct  10800
tatgtacaca cacaaacttc aaattaaatg agaactagaa gatttgagaa gttagctagc  10860
taatatccat agcattatga tattctaaat gatatgaatt ataagaatta ggtttcctga  10920
aatgaatgac tagaaaactt tcaagtagag attagtaaaa attaaaaagt cctaatcggc  10980
cattactgat ttgatgtttt taagagtcct aaaaaaatggg ttacatccat ttttaagtgg  11040
gtagtattat aacagccacc catcttcaat cacagtgatt tctgaattgt gagggaagtt  11100
attagcatga caggtgtctg gttctggccc tgtacgattc ccatgagtca agcaaattgt  11160
aagggctggt ctatatcaca cccaacccca aggatatgtc cctcaaaagt ctagcccagg  11220
ccccgtcatc ttcagcatca tctgggaaac caggtctgat tagtagtcct ttaaggaata  11280
cctcttaggc tcccatttta ctgctatcac agaatccaat aaaaccctta caggagattc  11340
aatgggaaat gctcaacacc cactgtagtt ggtggtgaca atgaccataa tttggctgtg  11400
ctggattcag gacagaaaat ttgggtgaaa gagcaggtga acaaaagagc ttcgacttgc  11460
cctagcagag agcaagccat accataccac aaagccacag caattacaac ggtgcagtac  11520
cagcacagta aatgaacaaa gtagagccca gaaacagacc cagaactata tgaggattta  11580
gtatacaata aagatggtat ttcgagtcag tagggaaaag atgaattatt caataaatga  11640
tgtttggcca actagtaacc catttgggaa aaaataaaag tatggtccct acctcacagc  11700
atacacaaaa ataaattcca gacggattaa aatctaaatg taaaaaataa agccataagt  11760
```

```
ggactggaag aaaatagaga attttttttta acatccgtag aaagggtaaa aacccaggca  11820
tgacatgaac caaaactgaa gaggttctgt aacaaatacc cccttttata tattgggctc  11880
caacaataag aacccatagg aaaatggaga atgaacacaa atagacaatt tatagaagag  11940
aaggttataa ggtgtaaaat tatatctatc tgagaaacaa acactaaaac aatgtgattc  12000
tactgttctc ccacccatac tggcaaaact taagcctgat aatatgctga ggggaaataa  12060
gcactcttgt tggtgagagt attaattggc atagcttctt ttgaaaatga catagcaata  12120
cctgttaaaa ttgcaaacat gcatgtcact taatccagta atcccacttc tgggaatcaa  12180
tgctacaaaa acactgacaa gtatacaaag atacattcaa gagtgttcac tgggccgggt  12240
gcggtggctt catgcctgta atcccaggga ggcagaggca agacgatcgc ttgaccccag  12300
gagttcaagg ccagcccgag aaacacagca agaccctgtc tctctttttt ttatttaaaa  12360
aataaatgtt cactgtatca gttgttcaca aaaacaaacc aacatgtcca ttaacaggga  12420
accatttaaa ttaatcaagt tcatctacac aatgtaatac catgcaacta ttaaaaagca  12480
cctgataatc caaagcacac tgagacagaa taatgctatt aaaaacacca agtagtggaa  12540
cactgtgttg cctatgacac catttttatt caacatttaa acaaatttgt aacagcaatt  12600
acatgagtag tgacaatggc gtttatgaga cttttcactt ttatgtgctt ctatttttgt  12660
tatgcttcta tatatacatc catttattat ggagtgttac tttcaaaaat cacaaatggg  12720
ccagtattat ttggtgttgc aaggtgagca tatgacttct gatatcaacc tttgcatatt  12780
acttctcaat ttagggaaat tacagacatc ccttattcta actaacttaa aacccagcat  12840
ttcaaacata cagaattgat ggggaaaaaa aagaaagaag aaagaaagaa aaggcaacaa  12900
gcttcagatg acagtgactc acatcaaatt atttataaaa tctgttaaat agtgccatct  12960
tctggagata cctggtatta cagtccaact ccagttgatg tctttacaga gacaagagga  13020
ataaaggaaa aaatattcaa gaactgaaaa gtatggagtc atggaaaaat tgctgtgatc  13080
caaaggctac ggtgatagga caagaaacaa gagaactcca agcagtaaga cactgctgtt  13140
ctattagcat ccaaacctcc atactcctgt ttgccccaag gctttttttaa aaaatagaga  13200
caggatctca ctattttgct caggctggtc ttgaactcct ggactcaagc tatcctcctg  13260
cctcggcctc ctaaagtgcc gagattacag gcttgagtca ccatacctgg ctatttattt  13320
tttcttaact ctcttgcctg gcctatagcc accatggaag ctaataaaga atattaattt  13380
aagagtaatg gtatagttca ctacattgga atacaggtat aagtgcctac attgtacatg  13440
aatggcatac atggatcaat taccccacct gggtggccaa aggaactgcg cgaacctccc  13500
tccttggctg tctggaacaa gcttcccact agatcccttt actgagtgcc tccctcatct  13560
ttaattatgg ttaagtctag gataacagga ctggcaaagg tgaggggaaa gcttcctcca  13620
gagttgctct accctctcct ctaccgtcct atctcctcac tcctctcagc caaggagtcc  13680
aatctgtcct gaactcagag cgtcactgtc aactacataa aattgccaga gaagctcttt  13740
gggactacaa acacataccc ttaatgtctt tatttctatt ttgtctacct cttcagtcta  13800
ggtgaaaaaa taggaaggat aatagggaag aactttgttt atgcctactt atccgcccct  13860
aggaattttg aaaacctcta ggtagcaata agaactgcag catggtatag aaaaagagga  13920
ggaaagctgt atagaaatgc ataataaatg ggcaggaaaa gaactgcttg gaacaaacag  13980
ggaggttgaa ctataaggag agaaagcaga gaggctaatc aacaaggctg ggttcccaag  14040
agggcatgat gagactatta ctaaggtagg aattactaag ggctccatgt ccccttagtg  14100
gcttagtact atgtagcttg ctttctgcag tgaacttcag acccttcttt taggatccta  14160
```

```
gaatggactt ttttttttta tcggaaaaca gtcattctct caacattcaa gcaggcccca  14220
agtctaccac actcaatcac attttctctt catatcataa tctctcaacc attctctgtc  14280
cttttaactg tttttctata ccctgatcaa atgccaacaa aagtgagaat gttagaatca  14340
tgtattttta gaggtagact gtatctcaga taaaaaaaaa gggcagatat tccattttcc  14400
aaaatatgta tgcagaaaaa ataagtatga aaggacatat gctcaggtaa caagttaatt  14460
tgtttacttg tattttatga attccctaaa acctacgtca cccgccccgt tcccacgccc  14520
cgcgccacgt cacaaactcc acccccctcat tatcatattg gcttcaatcc aaaataaggt  14580
atattattga tgatgttaat taacatgcat ggatccatat gcggtgtgaa ataccgcaca  14640
gatgcgtaag gagaaaatac cgcatcaggc gctcttccgc ttcctcgctc actgactcgc  14700
tgcgctcggt cgttcggctg cggcgagcgg tatcagctca ctcaaaggcg gtaatacggt  14760
tatccacaga atcaggggat aacgcaggaa agaacatgtg agcaaaaggc cagcaaaagg  14820
ccaggaaccg taaaaaggcc gcgttgctgg cgtttttcca taggctccgc ccccctgacg  14880
agcatcacaa aaatcgacgc tcaagtcaga ggtggcgaaa cccgacagga ctataaagat  14940
accaggcgtt tccccctgga agctccctcg tgcgctctcc tgttccgacc ctgccgctta  15000
ccggatacct gtccgccttt ctcccttcgg gaagcgtggc gctttctcat agctcacgct  15060
gtaggtatct cagttcggtg taggtcgttc gctccaagct gggctgtgtg cacgaacccc  15120
ccgttcagcc cgaccgctgc gccttatccg gtaactatcg tcttgagtcc aacccggtaa  15180
gacacgactt atcgccactg gcagcagcca ctggtaacag gattagcaga gcgaggtatg  15240
taggcggtgc tacagagttc ttgaagtggt ggcctaacta cggctacact agaaggacag  15300
tatttggtat ctgcgctctg ctgaagccag ttaccttcgg aaaaagagtt ggtagctctt  15360
gatccggcaa acaaaccacc gctggtagcg gtggtttttt tgtttgcaag cagcagatta  15420
cgcgcagaaa aaaaggatct caagaagatc ctttgatctt ttctacgggg tctgacgctc  15480
agtggaacga aaactcacgt taagggattt tggtcatgag attatcaaaa aggatcttca  15540
cctagatcct tttaaattaa aaatgaagtt ttaaatcaat ctaaagtata tatgagtaaa  15600
cttggtctga cagttaccaa tgcttaatca gtgaggcacc tatctcagcg atctgtctat  15660
ttcgttcatc catagttgcc tgactccccg tcgtgtagat aactacgata cgggagggct  15720
taccatctgg ccccagtgct gcaatgatac cgcgagaccc acgctcaccg gctccagatt  15780
tatcagcaat aaaccagcca gccggaaggg ccgagcgcag aagtggtcct gcaactttat  15840
ccgcctccat ccagtctatt aattgttgcc gggaagctag agtaagtagt tcgccagtta  15900
atagtttgcg caacgttgtt gccattgctg cagccatgag attatcaaaa aggatcttca  15960
cctagatcct tttcacgtag aaagccagtc cgcagaaacg gtgctgaccc cggatgaatg  16020
tcagctactg ggctatctgg acaagggaaa acgcaagcgc aaagagaaag caggtagctt  16080
gcagtgggct tacatggcga tagctagact gggcggtttt atggacagca agcgaaccgg  16140
aattgccagc tggggcgccc tctggtaagg ttgggaagcc ctgcaaagta aactggatgg  16200
ctttcttgcc gccaaggatc tgatggcgca ggggatcaag ctctgatcaa gagacaggat  16260
gaggatcgtt tcgcatgatt gaacaagatg gattgcacgc aggttctccg gccgcttggg  16320
tggagaggct attcggctat gactgggcac aacagacaat cggctgctct gatgccgccg  16380
tgttccggct gtcagcgcag gggcgcccgg ttctttttgt caagaccgac ctgtccggtg  16440
ccctgaatga actgcaagac gaggcagcgc ggctatcgtg gctggccacg acgggcgttc  16500
cttgcgcagc tgtgctcgac gttgtcactg aagcgggaag ggactggctg ctattgggcg  16560
```

```
aagtgccggg gcaggatctc ctgtcatctc accttgctcc tgccgagaaa gtatccatca  16620

tggctgatgc aatgcggcgg ctgcatacgc ttgatccggc tacctgccca ttcgaccacc  16680

aagcgaaaca tcgcatcgag cgagcacgta ctcggatgga agccggtctt gtcgatcagg  16740

atgatctgga cgaagagcat caggggctcg cgccagccga actgttcgcc aggctcaagg  16800

cgagcatgcc cgacggcgag gatctcgtcg tgacccatgg cgatgcctgc ttgccgaata  16860

tcatggtgga aaatggccgc ttttctggat tcatcgactg tggccggctg ggtgtggcgg  16920

accgctatca ggacatagcg ttggctaccc gtgatattgc tgaagagctt ggcggcgaat  16980

gggctgaccg cttcctcgtg ctttacggta tcgccgctcc cgattcgcag cgcatcgcct  17040

tctatcgcct tcttgacgag ttcttctgaa ttttgttaaa atttttgtta aatcagctca  17100

tttttaacc aataggccga aatcggcaaa atcccttata aatcaaaaga atagaccgag  17160

atagggttga gtgttgttcc agtttggaac aagagtccac tattaaagaa cgtggactcc  17220

aacgtcaaag ggcgaaaaac cgtctatcag ggcgatggcc cactacgtga accatcaccc  17280

taatcaagtt ttttggggtc gaggtgccgt aaagcactaa atcggaaccc taaagggagc  17340

ccccgattta gagcttgacg gggaaagccg gcgaacgtgg cgagaaagga agggaagaaa  17400

gcgaaaggag cgggcgctag ggcgctggca agtgtagcgg tcacgctgcg cgtaaccacc  17460

acacccgccg cgcttaatgc gccgctacag ggcgcgtcca ttcgccattc aggatcgaat  17520

taattcttaa ttaa                                                    17534
```

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 8

```
gtaacactgg cccaggaggc ctttctggtg acccc                             35
```

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 9

```
tgaccgggtc ctccggaaag accactgggg att                               33
```

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 10

```
tagttccttc tgcctggaat ac                                           22
```

<210> SEQ ID NO 11
<211> LENGTH: 22
<212> TYPE: DNA
<213> ORGANISM: Artificial Sequence
<220> FEATURE:

<223> OTHER INFORMATION: Description of Artificial Sequence: Synthetic primer

<400> SEQUENCE: 11
caagtcacaa ggatggacta ca 22

<210> SEQ ID NO 12
<211> LENGTH: 18524
<212> TYPE: DNA
<213> ORGANISM: Homo sapiens

<400> SEQUENCE: 12
tagttccttc tgcctggaat acttcctcat ctcacttgct ttcctgcctg gcagcttcct 60
acttgccctc tggaaccagc tctagggtca ccacatctct gcttctgagt gcctcctcag 120
acacagtctg tatttcctct tccaagctct catcacaaac attgtgctgt attatatgtt 180
tctgtgtggt cttccttcta tgaggaagcc ttggaaagca ggagacttat tttagtcttc 240
tttatgtttc ttttattccc aacacattat gtctgcccca tagacctttt caataaatga 300
ttattgagtt agtgactcct tttacatgct gacaaatgtg gctcttatta ctccccattt 360
cagtatcaca tatttgtaaa agtgaatcct tcttaatcgt tttacttttc tcctagtaaa 420
ttcctcatct atgcctgtct gctgctgttc tctgtgctgc tggcccttcg tttggatggc 480
atcatacagt ggagttactg ggctgtcttt gctccaatat ggctgtggaa gttaatggtc 540
attgttggag cctcagttgg aactggagtc tgggcacgaa atcctcaata tcggtaatac 600
tgctttatac aacccattgg tctctagcat gagggagcaa tatcttgact tttctcactt 660
ttgatgaagt aaggaccatt ttattttcta cctatctggg gtcttagaac tatagtataa 720
gctaacagat ctcttctgtg tttttgaaaa tttagtcttt ggtatgtatt ttcttacaaa 780
agcagtgcca tttgggggta agttgccagc cagctcacag atgcctatat aatccaaaat 840
gcacccaaaa tacagaactg gtatgccata ctagactaag cagcatgaaa ccaccctgtt 900
tttaggaaaa gacactcata ttatgtttgg tcatgaaaga tctttctcca atacagtttt 960
ggaactgggg ctccccttgt cccaccctcc tagtcccaga gctttaggac tattagcagt 1020
gtaggggagg tggcttgacc aggagaccat gagtccctga gacagcagct ggggaatgag 1080
gaaagtcaaa gattggatgc cgagaaggaa agcagagcct ttgggggcag gggagagggg 1140
taccctttac cgtttccaac tcttgccctc cctgctcttg gatgcctccg ctggcccaaa 1200
ttcctgggag ttgctcacgc cagcatgcaa cctgcttgtt gctgggacct gcgagagtct 1260
ttcccttctc tgccacagag actgtaacta cataaaggga aaaaggggga cttaagactg 1320
ggaggctatt atgaacctcc actgggaaaa tgaggagtac aggaattccc agaaggcagc 1380
tgctcatgtg ggaaaagtgt aaagttgaaa ctaccgcacc tttttttttt tttttttttt 1440
tttttttttt ttgagacaga gtttcgctct tgttgcccag gctggagtgc aatggtgtga 1500
tctcggccca ctgcagcctc cacatcccgg gttcaagtga ttctcctgcc tcggcctcct 1560
gagtagctgg gattacaggc acctgccacc atgcccagct aatttttgt atttttagta 1620 gagatagggt ttcaccatgc caggctagtt ttgaactcct gacatcaggt gatccacccg 1680
ccttggcctc ctgaagtgct gggattacag gtgtgagcca ccacgtccgg ccactacatc 1740
aactttttaa atttttgttt actaaatatg aaaatgattc agattgtgta aattacatat 1800
cacatacatg tctaagaact gtaaaacagt tacacagaga gccttggcag gtgagggaca 1860
ttcatgtata gctgtttcag agttcttaga ttttttttga aagattgatg acctgtgtgg 1920
ctgtatgtgt tttatttttt tatgagatat tttcagatat ctaatattaa ttgcttctca 1980

```
aagaatgcaa agttaaataa acatttaggt tctactaatt gatatttaga atatattcaa   2040
acttctcttt gttggtctta tttaagatgt tttgagcaag gaaaggaatt gtgtatgtgg   2100
ggttgaatgt aaggaatgta caggcgtggt cattctcatg ttaacattaa ccagtggaac   2160
atggttgggt cctacaggaa taacctctga tagcattttc tctatgatct aacttccggt   2220
gtatttgtca cccacaatac atgtatatca taaatgttca tctgtatttt gaataaacat   2280
tgtaggcctt tcagatgcat tatagagcct tttcctgatt agcggcctta ccattgctca   2340
attgtagatc tgttaaggtt attgtgcatg atacttagct aattaaactg attttgtttg   2400
agaacagttt taactcttgt tcttctttct ctttcatgtg caggtgttaa tttatcttaa   2460
tggaatagaa aggaaaatga aaatcattta tacgttttat ttgcatttaa aaatagcacc   2520
taacaatagt tactactatc ttgaaatata actggcactt gttcatagaa ctagagttat   2580
ttttataata ttgtgtgaag ggtggtttac atggtttctt gaaaaatgag gatcatgaga   2640
cttaaggggt atttgcctgg ttttagcagc agaagcaaat cagcttgaat aatcttggaa   2700
gtaactcttg ttgttgaatt taaagatgtg aacagaagtg tttatgtaca ttgtcaggga   2760
aataagaact ggctattact tttgagaata tccttatacg gttaaaacat taaattctgg   2820
tttggttgta atgttcattt tgtattatgt agtagttctt cgatgtttca gagattgcct   2880
accaaagctt aggtttaagt tagctttcta cctgatttcc ctttgctttt gtcaaatttt   2940
caagtaaaat tcaaagtata aatataagtt ggtatttgcc ctgaactgct tgcttatagt   3000
ggagattctg aactgagggt gttttcttct tctctccctt ttttagagca gaaggagaaa   3060
cgtgtgtgga gtttaaagcc atgttgattg cagtgggcat ccacttgctc ttgttgatgt   3120
ttgaagttct ggtctgtgac agaatcgaga gaggaagcca tttctggctc ctggtcttca   3180
tgccgctgtt ctttgtttcc ccggtgtctg ttgcagcttg cgtttggggc tttcgacatg   3240
acaggtcact agaggtgaga tttcatatat ttaagaatgt tttccacttt gggaggtcaa   3300
ggcaggtgga tcacttgagg tcaggagttt gagaccagcc tggccaacat ggtgaaaccc   3360
catctctact aataatacaa aaattagccg ggtgtggtgg catgcgccag taatcccagc   3420
ttctccggag gctgaggcgg gagaatctct tgaacccagg aggcggaggt tgcagtgagc   3480
caagattgaa ccattgcact ccagcctggg tgacagaatg aaactccgtc ttaaaaaaaa   3540
aaaaaaagaa tgttttcaaa agtaaaatat tttgctcagt tattcagatg tcaatttctt   3600
accctttgtt aggaagagct tgatcattac caactctaca tcatgagaca acaaggcaac   3660
aaaagatgat ggaaataaca atttttcttt cttcacttag aacactagct tttcacccag   3720
gacatcagcc ttctcccagc ttcacatcct gtatcaatca gacagaaaca gaactgatag   3780
gttagataca gatatatgta taaagagagt taaggaactg gctcacatta ctgtggggct   3840
ggcaagtctg aaatctccag ggcaggtgaa caggctggag acctaggagg agttgacact   3900
gcagtcctgg cacagaattt tttcctctcc aggaaaccac agtttttgct tttaaggcct   3960
tcacctgatt gcatgaggcc cacccatgct atggagggta gtctccttta ttcaaagtca   4020
gtaccttcac tgcaacagca agcttagtgt ttgattaaat aactgggtac tatagcccag   4080
ccaagttgac actcaaaact gaccatctcc ccacctcaga ccccatgatt tagcacctcc   4140
cctgctgtct ggttagctta tcctgatgtg cccctgtgtt tgtttattca ttcaataaac   4200
atttatcaag tatttactag atgccaagcc ctttttccct aagcatagag gatatgcaga   4260
tgaataaaat accaggacta gtaataatag taatgaaagt aattgcagat aacgtttatt   4320
gagcacttac tgtgtgccag gcattgtgcg aggcacatta catgtggtag ttttcttact   4380
```

```
aactaactct gtgaggtagg tccagagaag ataagtcatt tgttcatggc cacatgtgaa   4440
ggggcaggac caggattccg tttgagtcag cccgactcta aagcccgggc acataactac   4500
ataactgcat agaagctgag ggcccaaagc tgaatactga tgggttgagg ggagaactag   4560
aggctgtaga tgcctggttt tgagccgtgt ggatgaagag tgaagggaga agactgcagt   4620
tggcttagga agtaaacata gcagctgtag ggtgggtcag gcatataagc ctagacccca   4680
ggtatgggcg tgaggggaag gtatgtagac agagggacgg tgatggagca aggccctgtg   4740
ggactcaggg agaatgggac ctagagcacc aggaagggtt tggccttgaa caaggggagc   4800
tattccctga ttttcatgct ggtggaaagg ccacagcatg ggtatagtgg taggtaggag   4860
tgagccgtgg agggagagta tctgatggtc cactttcacc ctccctacaa ttcccagttt   4920
atatcaggga cttgagcatc catggatttt ggtatccaca gggggtcctg gaaccaatcc   4980
cccacagata ctgagggaca actatacaag gactaggact gcattgggcc tgaattacag   5040
aaagtaagtc tttcatatat tcacactcta ggcattcctg cccttggaag aaacaacata   5100
ccaggagctg agctccctcc tcctgtgatg caagaacagt acctatgttg gtgagggggt   5160
ggtctggagt aggctcatac agagatggga aggaggagtt gagggtctgc caggaagccc   5220
tgtgttggga gggaagggat ggcatttttg ggacacattg aagcctagag gcaggaaaca   5280
ctccatcagc tgagtggact gtggcgattc agatccgacg ggagcacaag gtggaaagga   5340
aggaactgtg ggagttgaga agagagggag cctctacaga gggattgggg caaatagggg   5400
ccacgtcctc agcccacaga gcatgtgctg aagtgcccca ggcaccccag tgcactcaca   5460
gggcaccagg ggatagtgga cattttgagg aaaacagtaa tacctgacat ttgttgggac   5520
accatacaaa ctactagctt gaaatagttt acaggtttat ttttaggcca cactgcattc   5580
ctttcagtga cgtcgtatct ttaagaagct gggttttcag cagttgctgt gaaaacaaaa   5640
aaggctaatg ctgtgtgaaa atccgggtga agaacaggta acgagtggga gcaccttgtc   5700
tgattccaag gcgtgggaaa tggtgagcta cctgacaggc acacgcatcc cactgggaat   5760
tagttttggt tatttaagaa taatattaac atttttcttt agatttatat gaattatttt   5820
ttctagtggc tacttagaaa tacttactaa gttagatgta attacttaaa tcagtgcaac   5880
tgttggcatt cccagccaca ttagggattt cttttggcct agaggtctat ggaggaatta   5940
ctaaattccc catgtaccta tgtactgaga acttttggga agctctgggc ctggtcccag   6000
atttcaattt tgtgggcaag aatgtacttt accagagtga ggagcagcct gcagggcgtt   6060
tgggctggag gcgggaggtt agtaaggggt tgctgaagtg gtaggcggat ggtgccgaag   6120
aaggcctcac taggcagtca tcatcaggat aggaagtggg cacgggattc aggagaaatc   6180
tggactttac agtggacagg atgtggtgac tgaacgtgac agtgtgggaa aaagaatgca   6240
gggtgattcc cgggctcatg gcttgagaaa tgagaccact gttgtgcctc caagtgacat   6300
gggaggctat agaaagtgac atgggaggct atagaaagtg acatgggagg ccatagaaag   6360
tgacatggga ggccatagaa agtgacatgg gaggccatag aaagtgacaa gggaggccat   6420
agaaagtgac atgggaggcc atagtgacat gggaggccat agaaagtgac atgggaggct   6480
atagaaagtg acatgggagg ccatagaaag tgacatggga ggccatagaa agtgacatgg   6540
gaggccatag tgacatggga ggccatagaa agtgacatgg gaggctatag aaagaggaga   6600
tacaaggttc taagtgcagg cgataatgat ctctatttgg gactggcttc atttgaggtg   6660
cctttaggag agccgagtgg cctatgcaca gctgggtctg ctatgcagca ggaaggctaa   6720
gttggagaca gatgtgagaa ctaaccatga aggaggtaat aatgcagacc aagggtctgg   6780
```

```
ttgaaatttc ttctccccca gtccagggtg cagcgggtga gtgaaaatat gtgtgtttgt   6840
gtgtctgtct tcctagtcgg gagagaagac tgagtttgtg gctctgcgga gcatcaccat   6900
ttaaggaggg ggaaaaggag acagaaggaa ttaccagaac actccagagg gctccaagac   6960
tgtatggtgg gatctagatg gccaggagga ggggagcaaa aaggaaagag tcatccacag   7020
tatcagtagg atgccagttg aagtgttttt gctgcctccc ggttatcggt gactttgatg   7080
aaagctgtct tctggtggtc atgggggtgg aggccagatc acaaggaagc tgggaatggt   7140
agatgagata gtaggggctt gcatattcat tactgtctcg cagagagaaa cctgaggcta   7200
agaggggtct tggatcaaag gatggggtgg gtttatctgg tttcggggct tttgttttta   7260
atgagaagga gtcatttctg tgctgctagg agggatcaat ggaataggtg gggttaaaga   7320
tacagtacgg aatctacagt tgatggcttg atgtgacaag gtcctcaagg agcctgaaag   7380
gaaggggtgg ggtccaaggg caaaaccgag gtatgagaag aaggatgcac aaggatggtt   7440
tcgagtagac agtattgttg gtagggacat gaaggaagtt tagtggtcta ttgcagctag   7500
cctgtgttcc cagtgaacct ggaaacaagg ttctcatctg tgctcaggcc tcaggccaga   7560
aagggcaagg cagcagaggg gcaaggcagc aggctgagcc ccatttcccc ttgccataat   7620
actgctgtgc ccctctggta ccgaaaatca ggagtttcca gtgcaatata atattataca   7680
agttacactg tattataatg tgtattgtct tttagtgtgt taaccaaatt actgcagtat   7740
taaatgcaaa ttatactttg tttaactgat tcttctcttc atttttagtt agaaatcctg   7800
tgttctgtca acattctcca gtttatattc attgccttaa gactggacaa gatcatccac   7860
tggccctggc ttgtatgtaa cttttaaaat ccttaaataa acttcttttt tattataaaa   7920
gtaattcata ttcactgtac aaagcttgga aaagacggac aagcagaagt aatagcctaa   7980
tagtcaccca taatcccacc atggggagat aacatggtta gtgtttttat gtctgtgttt   8040
tatacaaaca gtttggatat aactgtgtgc accattttgt atcctgattt ttttgtttta   8100
atgttgtatc ataaacattt tatcatgtta ataaaaggtc tttataaaca tgacttctaa   8160
agtttaattg atacaaaata ttcttcaagt gcatgtatca gaccatcctc ttatttctaa   8220
aatatggtat ttccattgtt gccagtgttg aatgatttta aatcatactg cagtatatat   8280
gtttatgcat taaaattttt gccttttgtt ttttggttgt tttcttagga aatagtccag   8340
aaatagtgtt actgagctag aggttgggaa ctatttgaga ttcctatata cgtatactgc   8400
actgccaact tgcttttcca aaagccatac ctggccaggc gcagtggctt acacttacag   8460
tcccagcact ttgggaggcc gaggtgagct gatcacttga gctcaggagt tcgagaccaa   8520
cctgtgcaat gtagcaagac cctgtctcaa aagaaaaaaa aaaaaagcca tacccattta   8580
cactcttgct ggtggtggca tctatgtcat gcttctaaac tgtgacttca gttactgggc   8640
atttggttga aattaactgt gaataaatgg gtagatggat gcagagatag aaagataagt   8700
ggcaaggtag aaattagaga acacagtata gattccacta ttaaatgcat ggaaaaaaga   8760
tggagactaa aggcagaaga gttccattgc cactgggagg taaggtcatg ctagtgtttt   8820
tgttcggttt tattttctct gttgtttgat gtataatttt gcatacaata tattttatgt   8880
attaaatata gctaccctta aaaagtgaaa agtatagtaa agaattggga gcagagaaga   8940
aatgaaggga acctaagtat actccatatt taaagatggg aataatcact tctgcccaaa   9000
gtctttgata aaacattcat aataaaaaat attcagtcac tcatcctaca acttcacagt   9060
gctgtatctg gagaatggtc attgggttca aaactgtttc tgttgtgacg tgaaggaaac   9120
atatctaaac aagaccaaat tttttcgtat aagatactgt cagggaaaaa aaagattagt   9180
```

```
aattttgaga gctttccaca aatgagaaga aagatttttt ctgcccttca tcctctgtag   9240
atcccagttg atgaagcagt ctgagtacat gtttcccata gtgagcaaga gaaaacaagg   9300
aagcctattg agatctaaca ttccacccat gaagggaact tcagtaaaaa ggagaatctc   9360
atcacagaat ggggaacggg gaagaaaggc tgtgcataga ctctgcagag aaacctacaa   9420
tcaagaactg gtcaggagaa gtaaaattcg tatgccaact caaatcatag atctaaaaga   9480
aaatgtaaaa ctatagatct gttaggaaat aacataggac agaatctttg ggtttgcaa    9540
ttaggcagag agtacttaga aatggcactg ttaatatggt ccatacgaga gagaaatcat   9600
aaatttggac ttcctcaaaa ttaaaatgaa atgaagacag gccacagact gggagaaaat   9660
atttgcaaag cacacatcaa aacactgact tgcacccaga acatacagag aactcttaaa   9720
aactcaaaac tgcaaaaaga aacacctaaa aattggcaaa agagttgaca atttgcgaag   9780
gggatataca catggcgaaa aagcacagga aaagatgctc aacgccatta caggttaggg   9840
aagacaaact acaaccagga tgagggcccg aaacacatgg cttcagaatg gtgaaactca   9900
gcaacactga cgaggccacg tgcctgggag gatgcagagg aactgggaca ctccagtgtt   9960
actggcggga aggcaggtgg tacgggcact gtagaaaatg gtttggccat ctctgatgca  10020
gttaaaagcg cacttcccgt gggacttggc tgccccactc ctgggtataa gatttacccc  10080
cagagaagtg aaagcgcgca gccttgtaga aacccacaca ccagtgtttg tagcagtctt  10140
gtttgcattt tggatagcgg ccttgtttgg ttttcacaaa ccaccctcag cggacagtca  10200
gataaactgt aggcatccat acaatggaat accactcaga tctgagaggg aacgacctgt  10260
ggatacaggg agggaacaac ttggatgaat ctcattagag acattatgtg gatggcggga  10320
agccagtctc aacaggttac ttgtctcgcg atgccatcta cataaagttc cagcagagac  10380
aaaagtacag tgagagaaca gatcagtgtt tgccggggct aatggtgggg acggtgtgat  10440
agtgaaggga cagcacggag agttttgcag ggtgacagac ctcttctgca tcctgccaac  10500
ggctgtgtga atctacttgt gtgaagactc agggaactca caccaaagga agacggtcac  10560
ttttcctact gtatgataga taattaataa aaagggagaa cggaggagtg tcgtcccagg  10620
aggcagggca ggagggcgaa gacgtgtcac aggggagcct ggccaagtgg cgcccccgga  10680
actcgtcctc tgggcttgtg tgtggatgag acaaggtcta cctggtacga cagggacata  10740
ctgggaatgc gcccttgccg tggaggcggg gacccggcag cgctacgtat ccagcatcaa  10800
cctgtatcca gcatcaaccc gccaagttca ctaacttggt aggggtgagg ttagggatcc  10860
ttaggagccc aggcagccag actttctggg gagcccattc ccatttgtgt tgccaaagta  10920
cccccagcag gttgtgggaa tgttgcctgt gaagagagtc tgttggggtg agatcttgtg  10980
tgtgtgcaca gggtgacagt tgtgtcccat ttcccgggaa gctgtgatgg cagcagaacc  11040
tagaggagcc tgagagagtg tgggagagtg ggcctctgga agagtagagg ctgcggagcc  11100
aggtgcaggg ctgtctgtca cccaaaggaa gagggactga tgactcactg agcgtgtgtg  11160
tcccctggtg gcagcaggcc ccatagtgaa cataccatac cttttctgtc ctgagcgatg  11220
ctcccagcag tcctgggaga tggaacggtc cttattcggc tcacaggaag gaccgcctta  11280
actggacaga cacagcaagg tgctaaagat gccttccatc agaggccagg ttggaagctc  11340
taaagagact tctcttgctg ttctctcacc cacccccagg ttgtgtgtgt cccgctgtgg  11400
attctcatgt cctttctgtg cctggtggtc ctctactaca ttgtgtggtc cgtcttgttc  11460
ttgcgctcta tggatgtgat tgcggacagc gcaggacaca cataaccatg gccctgagct  11520
ggatgaccat cgtcgtgccc cttcttacat ttgaggtaag cgttccacgg gaagcctctt  11580
```

```
cagcccctga agcttgcgct tcccctgaca ggattctgca cccctagaaa ggcagcctct  11640
gtccctcgag ctcacagtga gcccactcca ggagagggga gagaacacag ccatctccga  11700
gagggagctt cggtgaaagg agagcatcct tcctttctct tgggggcagc acgtggggct  11760
ggcagggaga agagtgcacc tttttagcca tggtgcctct gtatggctcc agtttccact  11820
ctggggaaag cagagtggga tgtcagattt gtgtattgga gtcacgtgga gaattctaga  11880
atgggagctg ttgactcctt agaacaaaca cccggaggag tttgccataa aactgctggc  11940
actgggaact tttcaagtgg ataggctatt gccgagctct gaagagggac ataaaagctc  12000
atttcgagct ttccccaggg ataggtggtt tcctgccttt ttctggcggt gctgatgttc  12060
cctcttgtgg gagctcacgc gggggtgggg tggtggggag gaactgccta atgaagtctg  12120
gcttccgcct ctgcccattt tcggtgctgg catcaaccgg gactatgtct ctttctttag  12180
attctgctgg ttcacaaact ggatggccac aacgccttct cctgcatccc gatctttgtc  12240
cccctttggc tctcgttgat cacgctgatg gcaaccacat ttggacagaa gggaggaaac  12300
cactgtatgt actcagcatt tcagaagtcc ttggtgtgtg tctggggggg gaccaggggg  12360
tggggggtgg cggatagaag tctaggaagg gatgagtccc cgagggcccc aatttagaag  12420
cttgtgtggg aaagtgaggg ctgaggaaat tctgggacct tctaagggaa gggcatgccg  12480
taactctggt gttctgctgg cctgcaccgg gacttttctc gcagtgcacg ctgccatttg  12540
aggtagaacc agacacggca ggcaacctct cagagatccc gttccctcct ctgcaaaatg  12600
gggatcaaga cagattcttc ccaggcccgg gagggtttga tggaaaatcc acatctccca  12660
cccaaacctg ggattcatcc taggtccctg ttggccgctc tgcctccccc atatccttgc  12720
tgccatcacc cgagtcttgc ctgtcttgcc ttgctaacac tctattcccc tccacctgct  12780
tgctgaggca gacacttcca aaacgatctc tgcagagggt gccttcctgg caaggctgtg  12840
ggctccatgg cacggaagcc cagagcattg cccttcggaa agccagtggg tttgggggca  12900
gggcctcact gcagcccagc agcccgggct gtgcttgctg tttgtgcctc tgccccctac  12960
cccgcacccg ggagcaggga gggcttgcac cgagctgaca ctccagtagc ctacagagag  13020
gagtagtggg actgggaaag tggctttaag gtggctccat gagttcaggc cccctcctgg  13080
ccaacccgtg catgactacc gccctcacgg attccagagg gtgacagaaa tcttgttctt  13140
gggtggcact gtcatccatg agtttatcct ggctggagaa gattagcgga agacaccgta  13200
gtctgcgcac cacagatatt ttgagactca ctggagcagt agttctcaaa tttgggcatc  13260
cagcagaatc ccaaaagggc caggaaaagg ggaccgctgg agcccaccct agcccgactc  13320
agtttctgga ggtctgggct ggggcccgag aatggcatcc ctaactaggc cccgtggacg  13380
ctgtccctgc cggtccggga accccactcc aagcaccaca gagctagcat ttgcacttct  13440
tccccatttt gggtactcaa gccctgttca ggctttgtga ctcaggagtc tggataaagt  13500
atgttatgac attgtaggag tgaaacttct tgttacggaa agaaagttaa caggaaggtc  13560
agttgagcct cgtgtgtgaa ataaaaaatt cttatttttc agggtggttt ggtatccgca  13620
aagatttctg tcagtttctg cttgaaatct tcccatttct acgagaatat ggaaacattt  13680
cctatgatct ccatcacgaa gataatgaag aaaccgaaga gaccccagtt ccggagcccc  13740
ctaaaatcgc acccatgttt cgaaagaagg ccagggtggt cattacccag agccctggga  13800
agtatgtgct cccacctccc aaattaaata tcgaaatgcc agattagatg ccacttccgg  13860
ggacagagct taagtggact gggacgcact ctctccgcct tcctctgccc cctcgttcac  13920
cccgcagacc agaaccagta ctggagctgg gtctccaggt acgtccatct catgccttgt  13980
```

```
ttgcatccag cgcctatcag ccactcacca cgacgggacg cggaagtggc aggtgacggg  14040
ggtgtgtgcc agcagatgcg gatgccagga agagtgtgag aacaggggtg ggattaccgt  14100
ctgtctggga ggggctccag gtacccctct tccccgtcag acccactggg agatggctgc  14160
ttgccaggcc cccagaagga acatctgtct atacggtgct gaaatcccaa tcaaaagtat  14220
tgtttagaaa tgtatttctc cacagggctg acctcctgca gctcgctgag cactcccagg  14280
tcctcagcac tcccaggtcg tggctggggc agtcagtagg aactgtaact atgtctctga  14340
tgcaccacgt gtttagacac agcacagtcc tttttctgt tcctactgtg gaagtagttt  14400
ctctttgggc atgctgacag cagtttttca tagcctcacg gatgagccct ttctacggga  14460
gtgactccat gcttgtatac agagtattta tacaaatgtt ttagcatctt catatgcggt  14520
gttaacccct agttctgtac agcatattct gttcaagtat ttttttacaa gcttgtgctg  14580
taggcacatg ccttctgctg cagaagtgga cgcccgtggc acactccccc cccccccccg  14640
tggggtgcca cgccttcatg ggacattgcc acttctgccc tggaactcgt gcaggtacgt  14700
agtagctgct actgccacaa cggcaacacc aagcaagaga tggtccatgc ttttctgacg  14760
ttctcagaat agtggctagc ttcaaacctg acaagcgctg cttgaagccg gaacactaga  14820
gaatgttgct gagagcagaa acggccacgc gggtcacgac tatgcgtggg aaagtctcaa  14880
gcttccctcc tgccagcaac aagaaggctt tggagtaggc atgatgtttt cacgtgtgcg  14940
tgccgtttct ccaagcactg caggttccac cgtgtgtcag aggctgcaag tttaacatcc  15000
tcctgcctga aaacaaatag gtcctttgct gaaaagaggg taaaaaaaga gctttgatct  15060
tctcagccag gagaagaggg tggtgttttc acgcgggcaa ctgctcgccg gcctacatgg  15120
ggttaattca agtctgctgc gagcacgact ccgccccttgg cactggcctc cagcaagccc  15180
tgttctcttt ggggtacagg ggaacgggat ggtttagact ttcctgctca gtgtgtaaaa  15240
aatgtagcta aagccactat ttttgctctc cttaagctgt tcaataaacc ggttcctcat  15300
tttacacgtg catgatgtgt atcttctttg ctggatgggc caggaaactg gagtggtcct  15360
ctcagccagc ctcagaggaa agaaatctct agctggcaca ggcagccagt gagtgaggct  15420
ggcggctgca ggggcacagc ctttagaatg agtccttcag tgcacaggtc ccagggtata  15480
cggggtagtg ggaggaagga ggggacgcct cgcagatgcc actgttggct gggctacacc  15540
ttgccacact tgttactgct taggaggctt tctggagtgt tccttgggtg ctacgacaat  15600
ctgcagcaga cactgtcctt tcaccgctcc tggtcctcgt ttgctcccca gtgatgtcaa  15660
cagctgagga ctgctcacgc tgcaacaaaa ggctctgcag tcgctgtcta gcttgcccta  15720
gtcgtctcta gagttctgcc tgaactgaaa ctcaagtggg gttcagctca tgacttgtgg  15780
caattgacca ggaaattcac cagttgctgt ggctggaagg attttcagtc ctgtgggttg  15840
taaccagagg ccacaggtgg attctgcctt aggctcatga gatttccgac ttgctgttga  15900
agaaaatgcc ttgtgaagtg acaacagtag ctctgaccca actgccggtg cctcgctagt  15960
tcctatacgt cccactggat cctcacagcc ccgggaagca ggtgctacta ctcttatccc  16020
cgggaggaga cagaggccga gagaggttaa gtgacgtgcc caagtcacac agctcggcag  16080
cggccgggtt gagcatcagc agtctgtttg cagacccctc actgtcaccc cctgagccag  16140
tgcgccttgg gccctgcggt caggatgtct caagcgtgga ggcatcaccg gttcgtggca  16200
gtctctggaa ggtcactgag ctctgtgccc agaatcgagt cgggggagtc tgtgcagagg  16260
tggccctgtg tgtggggaca gtgtgtgaca cagacactgc tttggatgga cacctctccc  16320
gtgacctcct agcatccaat cccaaaggaa caactgttgc agagatggac cgctggacac  16380
```

```
aaacccacgt gcgtttctct ggagacactg gccaaggaaa acaaaacatg ctcgaaggcc  16440
aacagctgca tgccccaccg cgatgtgacc gcagacaccc ggggtgtaga agggtctctg  16500
cctggtgggg ggacacgtgc aggccgagga gaggcaggaa ggaggctgcc tccgactccc  16560
cactggactg catggcgacg gcgtgtggtg gggcagtcag ctaagccatt tgcctaaggg  16620
gctgtcgggc atctgcgtgc tggggaccga cagtgtgggt gtgttaggag gatctgtatg  16680
gagcacattg ctgcctctgg ctaggacagg gtggaaaggg tggcgtggct acagcctgac  16740
ccatgggcac cgtcctaccc tttgttctgt gcttccgagt gtcagtcatg tgctggggtc  16800
tgtgggccca tgactcagac ggtgagctct gaccttcctg agccagggct ttgctgtagt  16860
tgtgcctggc tcaggagctc taggacaagg ggaccgctcc aggtctgcat ctacggtgtg  16920
gcagggcccc tcggcactct tgtgcactag tgtcatcttt cccattgaaa tgactgtgag  16980
gaccagaatg tgcacatgca gatgggcagc tacttgtctg ccttggccct ttattacaca  17040
acttgctggg ggtggagatg ccaccccccg gcagtcagag cccctttatg atgtcatggg  17100
gctggttaca tgactgccaa ggggtgctgc tggccacact gcactagcaa gtttgccaga  17160
tggaggacaa gcgatcattg agtatggctc gctgtgaaga aagaaattcg agaggacagg  17220
atcatggctt ggaaagggtg cctttccctc cccagttgca gtcagagacc taccttcacc  17280
cagcagatcc ttcccctgcc tgggacgacc cggggtccac tgggagccct aacttgaggc  17340
tgctgacaga agaaatcgct ttccaacctc tggccgagga agcttcgttc agaaggccgc  17400
accctgacgg tgacgtcccg ccccagggag aagataatct cctctccctc ccctttccac  17460
agaaactgtg gagactggtc agcagcaacc agttttcgtc catctggtgg gatgacagtg  17520
gggcttgtag agtgatcaat caaaaactct ttgaaaagga gattctcaaa agggacgtcg  17580
cacacaaagt gtttgccaca acttcgataa agagcttctt ccgccagcta aacttgtatg  17640
gcttccgaaa acggcgtcaa tgcactttca ggaccttcac ccgcattttc tccgcaaaaa  17700
ggctggtctc catcttgaat aaggtaatga acgacaagcc tctggagggg ttaagtcggt  17760
gggctctggg gcctggtcgg gtggaagtcc caggactgcc tcctgggaag tgggcgacct  17820
caggcagggt gtggggccat cgctgtgggc ctgtgtcccc ctctgggtgg aggtgacatg  17880
aactaagagt gaatgtgggg agagggctga ggatggtgcg ggcccctctc gagtgtgtaa  17940
aatatcacag gtgccaagta gccgtatctg cgtgtcgtcc tccccggggc cagccatgtc  18000
atctggtggt tgctgtgtcc ccctgactcc acagcacatt accctgtgag gtgagcaggc  18060
caggggagtc tggtatttgt accactgtca ccctagctgg tgtctggaga ggtgctcaag  18120
tggaagcact gaagggcgcc tggcgcagga ggtgcagatg ctcctgctgc ccttggtagg  18180
tgggcccctg gtgtggaaga gccagtaccc agggcctcca acccagccgg ggtgcattct  18240
gttgccagct gacactgcat gggggaggcc cagaatcttc ttccctcctg gtctgcaact  18300
tcaaagaccc tttccgccgg ccatggacac cctaatctgc cattttgagg ctttttccaa  18360
gacggaaagg cccgccacaa cttggtaaac cttgacgatg tgaacgcgag tccccagctt  18420
cctttgggga ctgggacctt ttccagaaag gcctcctggg ccagtagagt tctcttgcac  18480
aggggcgtag atggttggta gttgtagtcc atccttgtga cttg                   18524
```

<210> SEQ ID NO 13
<211> LENGTH: 7695
<212> TYPE: DNA
<213> ORGANISM: Homo sapiens

<400> SEQUENCE: 13

```
ggcccaggag gcctttctgg aaaaggtccc agtccccaaa ggaagctggg gactcgcgtt     60
cacatcgtca aggtttacca agttgtggcg ggcctttccg tcttggaaaa agcctcaaaa    120
tggcagatta gggtgtccat ggccggcgga aagggtcttt gaagttgcag accaggaggg    180
aagaagattc tgggcctccc ccatgcagtg tcagctggca acagaatgca ccccggctgg    240
gttggaggcc ctgggtactg gctcttccac accaggggcc cacctaccaa gggcagcagg    300
agcatctgca cctcctgcgc caggcgccct tcagtgcttc cacttgagca cctctccaga    360
caccagctag ggtgacagtg gtacaaatac cagactcccc tggcctgctc acctcacagg    420
gtaatgtgct gtggagtcag gggacacag caaccaccag atgacatggc tggccccggg     480
gaggacgaca cgcagatacg gctacttggc acctgtgata ttttacacac tcgagagggg    540
cccgcaccat cctcagccct ctccccacat tcactcttag ttcatgtcac ctccacccag    600
agggggacac aggcccacag cgatggcccc acaccctgcc tgaggtcgcc cacttcccag    660
gaggcagtcc tgggacttcc acccgaccag gccccagagc ccaccgactt aacccctcca    720
gaggcttgtc gttcattacc ttattcaaga tggagaccag ccttttgcg gagaaaatgc     780
gggtgaaggt cctgaaagtg cattgacgcc gttttcggaa gccatacaag tttagctggc    840
ggaagaagct ctttatcgaa gttgtggcaa acactttgtg tgcgacgtcc cttttgagaa    900
tctccttttc aaagagtttt tgattgatca ctctacaagc cccactgtca tcccaccaga    960
tggacgaaaa ctggttgctg ctgaccagtc tccacagttt ctgtggaaag gggagggaga   1020
ggagattatc ttctccctgg ggcgggacgt caccgtcagg gtgcggcctt ctgaacgaag   1080
cttcctcggc cagaggttgg aaagcgattt cttctgtcag cagcctcaag ttagggctcc   1140
cagtggaccc cgggtcgtcc caggcagggg aaggatctgc tgggtgaagg taggtctctg   1200
actgcaactg gggagggaaa ggcacccttt ccaagccatg atcctgtcct ctcgaatttc   1260
tttcttcaca gcgagccata ctcaatgatc gcttgtcctc catctggcaa acttgctagt   1320
gcagtgtggc cagcagcacc ccttggcagt catgtaacca gccccatgac atcataaagg   1380
ggctctgact gccggggggt ggcatctcca cccccagcaa gttgtgtaat aaagggccaa   1440
ggcagacaag tagctgccca tctgcatgtg cacattctgg tcctcacagt catttcaatg   1500
ggaaagatga cactagtgca caagagtgcc gaggggccct gccacaccgt agatgcagac   1560
ctggagcggt ccccttgtcc tagagctcct gagccaggca caactacagc aaagccctgg   1620
ctcaggaagg tcagagctca ccgtctgagt catgggccca cagaccccag cacatgactg   1680
acactcggaa gcacagaaca aagggtagga cggtgcccat gggtcaggct gtagccacgc   1740
caccctttcc accctgtcct agccagaggc agcaatgtgc tccatacaga tcctcctaac   1800
acacccacac tgtcggtccc cagcacgcag atgcccgaca gcccccttagg caaatggctt  1860
agctgactgc cccaccacac gccgtcgcca tgcagtccag tggggagtcg gaggcagcct   1920
ccttcctgcc tctcctcggc ctgcacgtgt ccccccacca ggcagagacc cttctacacc   1980
ccgggtgtct gcggtcacat cgcggtgggg catgcagctg ttggccttcg agcatgtttt   2040
gttttccttg gccagtgtct ccagagaaac gcacgtgggt ttgtgtccag cggtccatct   2100
ctgcaacagt tgttcctttg ggattggatg ctaggaggtc acgggagagg tgtccatcca   2160
aagcagtgtc tgtgtcacac actgtcccca cacacaggc cacctctgca cagactcccc    2220
cgactcgatt ctgggcacag agctcagtga ccttccagag actgccacga accggtgatg   2280
cctccacgct tgagacatcc tgaccgcagg gcccaaggcg cactggctca gggggtgaca   2340
gtgaggggtc tgcaaacaga ctgctgatgc tcaacccggc cgctgccgag ctgtgtgact   2400
```

```
tgggcacgtc acttaacctc tctcggcctc tgtctcctcc cggggataag agtagtagca   2460
cctgcttccc ggggctgtga ggatccagtg ggacgtatag gaactagcga ggcaccggca   2520
gttgggtcag agctactgtt gtcacttcac aaggcatttt cttcaacagc aagtcggaaa   2580
tctcatgagc ctaaggcaga atccacctgt ggcctctggt tacaacccac aggactgaaa   2640
atccttccag ccacagcaac tggtgaattt cctggtcaat tgccacaagt catgagctga   2700
accccacttg agtttcagtt caggcagaac tctagagacg actagggcaa gctagacagc   2760
gactgcagag ccttttgttg cagcgtgagc agtcctcagc tgttgacatc actggggagc   2820
aaacgaggac caggagcggt gaaaggacag tgtctgctgc agattgtcgt agcacccaag   2880
gaacactcca gaaagcctcc taagcagtaa caagtgtggc aaggtgtagc ccagccaaca   2940
gtggcatctg cgaggcgtcc cctccttcct cccactaccc cgtataccct gggacctgtg   3000
cactgaagga ctcattctaa aggctgtgcc cctgcagccg ccagcctcac tcactggctg   3060
cctgtgccag ctagagattt ctttcctctg aggctggctg agaggaccac tccagtttcc   3120
tggcccatcc agcaaagaag atacacatca tgcacgtgta aaatgaggaa ccggtttatt   3180
gaacagctta aggagagcaa aaatagtggc tttagctaca tttttacac actgagcagg   3240
aaagtctaaa ccatcccgtt cccctgtacc ccaaagagaa cagggcttgc tggaggccag   3300
tgccaagggc ggagtcgtgc tcgcagcaga cttgaattaa ccccatgtag gccggcgagc   3360
agttgcccgc gtgaaaacac caccctcttc tcctggctga gaagatcaaa gctctttttt   3420
taccctcttt tcagcaaagg acctatttgt tttcaggcag gaggatgtta aacttgcagc   3480
ctctgacaca cggtggaacc tgcagtgctt ggagaaacgg cacgcacacg tgaaaacatc   3540
atgcctactc caaagccttc ttgttgctgg caggagggaa gcttgagact ttcccacgca   3600
tagtcgtgac ccgcgtggcc gtttctgctc tcagcaacat tctctagtgt tccggcttca   3660
agcagcgctt gtcaggtttg aagctagcca ctattctgag aacgtcagaa aagcatggac   3720
catctcttgc ttggtgttgc cgttgtggca gtagcagcta ctacgtacct gcacgagttc   3780
cagggcagaa gtggcaatgt cccatgaagg cgtggcaccc cacggggggg gggggggagt   3840
gtgccacggg cgtccacttc tgcagcagaa ggcatgtgcc tacagcacaa gcttgtaaaa   3900
aaatacttga acagaatatg ctgtacagaa ctaggggtta acaccgcata tgaagatgct   3960
aaaacatttg tataaatact ctgtatacaa gcatggagtc actcccgtag aaagggctca   4020
tccgtgaggc tatgaaaaac tgctgtcagc atgcccaaag agaaactact tccacagtag   4080
gaacagaaaa aaggactgtg ctgtgtctaa acacgtggtg catcagagac atagttacag   4140
ttcctactga ctgccccagc cacgacctgg gagtgctgag gacctgggag tgctcagcga   4200
gctgcaggag gtcagccctg tggagaaata catttctaaa caatactttt gattgggatt   4260
tcagcaccgt atagacagat gttccttctg gggcctggc aagcagccat ctcccagtgg   4320
gtctgacggg gaagaggggt acctggagcc cctcccagac agacggtaat cccacccctg   4380
ttctcacact cttcctggca tccgcatctg ctggcacaca cccccgtcac ctgccacttc   4440
cgcgtcccgt cgtggtgagt ggctgatagg cgctggatgc aaacaaggca tgagatggac   4500
gtacctggag acccagctcc agtactggtt ctggtctgcg gggtgaacga gggggcagag   4560
gaaggcggag agagtgcgtc ccagtccact taagctctgt ccccggaagt ggcatctaat   4620
ctggcatttc gatatttaat ttgggaggtg ggagcacata cttcccaggg ctctgggtaa   4680
tgaccaccct ggccttcttt cgaaacatgg gtgcgatttt agggggctcc ggaactgggg   4740
tctcttcggt ttcttcatta tcttcgtgat ggagatcata ggaaatgttt ccatattctc   4800
```

-continued

```
gtagaaatgg gaagatttca agcagaaact gacagaaatc tttgcggata ccaaaccacc   4860
ctgaaaaata agaatttttt atttcacaca cgaggctcaa ctgaccttcc tgttaacttt   4920
ctttccgtaa caagaagttt cactcctaca atgtcataac atactttatc cagactcctg   4980
agtcacaaag cctgaacagg gcttgagtac ccaaaatggg gaagaagtgc aaatgctagc   5040
tctgtggtgc ttggagtggg gttcccggac cggcagggac agcgtccacg ggcctagtt   5100
agggatgcca ttctcgggcc ccagcccaga cctccagaaa ctgagtcggg ctagggtggg   5160
ctccagcggt cccctttcc tggccctttt gggattctgc tggatgccca aatttgagaa   5220
ctactgctcc agtgagtctc aaaatatctg tggtgcgcag actacggtgt cttccgctaa   5280
tcttctccag ccaggataaa ctcatggatg acagtgccac ccaagaacaa gatttctgtc   5340
accctctgga atccgtgagg gcggtagtca tgcacgggtt ggccaggagg gggcctgaac   5400
tcatggagcc accttaaagc cactttccca gtcccactac tcctctctgt aggctactgg   5460
agtgtcagct cggtgcaagc cctccctgct cccgggtgcg gggtaggggg cagaggcaca   5520
aacagcaagc acagcccggg ctgctgggct gcagtgaggc cctgccccca aacccactgg   5580
ctttccgaag ggcaatgctc tgggcttccg tgccatggag cccacagcct tgccaggaag   5640
gcaccctctg cagagatcgt tttggaagtg tctgcctcag caagcaggtg gaggggaata   5700
gagtgttagc aaggcaagac aggcaagact cgggtgatgg cagcaaggat atgggggagg   5760
cagagcggcc aacagggacc taggatgaat cccaggtttg ggtgggagat gtggattttc   5820
catcaaaccc tcccgggcct gggaagaatc tgtcttgatc cccattttgc agaggaggga   5880
acgggatctc tgagaggttg cctgccgtgt ctggttctac ctcaaatggc agcgtgcact   5940
gcgagaaaag tcccggtgca ggccagcaga acaccagagt tacggcatgc ccttccctta   6000
gaaggtccca gaatttcctc agccctcact ttcccacaca agcttctaaa ttggggccct   6060
cggggactca tcccttccta gacttctatc cgccaccccc cacccccctgg tcccccccca   6120
gacacacacc aaggacttct gaaatgctga gtacatacag tggtttcctc ccttctgtcc   6180
aaatgtggtt gccatcagcg tgatcaacga gagccaaagg gggacaaaga tcgggatgca   6240
ggagaaggcg ttgtggccat ccagtttgtg aaccagcaga atctaaagaa agagacatag   6300
tcccggttga tgccagcacc gaaaatgggc agaggcggaa gccagacttc attaggcagt   6360
tcctccccac caccccaccc ccgcgtgagc tcccacaaga gggaacatca gcaccgccag   6420
aaaaaggcag gaaaccacct atccctgggg aaagctcgaa atgagctttt atgtccctct   6480
tcagagctcg gcaatagcct atccacttga aaagttccca gtgccagcag ttttatggca   6540
aactcctccg ggtgtttgtt ctaaggagtc aacagctccc attctagaat tctccacgtg   6600
actccaatac acaaatctga catcccactc tgctttcccc agagtggaaa ctggagccat   6660
acagaggcac catggctaaa aaggtgcact cttctccctg ccagccccac gtgctgcccc   6720
caagagaaag gaaggatgct ctcctttcac cgaagctccc tctcggagat ggctgtgttc   6780
tctcccctct cctggagtgg gctcactgtg agctcgaggg acagaggctg cctttctagg   6840
ggtgcagaat cctgtcaggg gaagcgcaag cttcaggggc tgaagaggct tcccgtggaa   6900
cgcttacctc aaatgtaaga aggggcacga cgatggtcat ccagctcagg gccatggtta   6960
tgtgtgtcct gcgctgtccg caatcacatc catagagcgc aagaacaaga cggaccacac   7020
aatgtagtag aggaccacca ggcacagaaa ggacatgaga atccacagcg ggacacacac   7080
aacctggggg tgggtgagag aacagcaaga gaagtctctt tagagcttcc aacctggcct   7140
ctgatggaag gcatctttag caccttgctg tgtctgtcca gttaaggcgg tccttcctgt   7200
```

```
gagccgaata aggaccgttc catctcccag gactgctggg agcatcgctc aggacagaaa   7260

aggtatggta tgttcactat ggggcctgct gccaccaggg gacacacacg ctcagtgagt   7320

catcagtccc tcttcctttg ggtgacagac agccctgcac ctggctccgc agcctctact   7380

cttccagagg cccactctcc cacactctct caggctcctc taggttctgc tgccatcaca   7440

gcttcccggg aaatgggaca caactgtcac cctgtgcaca cacacaagat ctcaccccaa   7500

cagactctct tcacaggcaa cattcccaca acctgctggg ggtactttgg caacacaaat   7560

gggaatgggc tccccagaaa gtctggctgc ctgggctcct aaggatccct aacctcaccc   7620

ctaccaagtt agtgaacttg gcgggttgat gctggataca ggttgatgct ggatacgtag   7680

cgctgccggg tgacc                                                    7695
```

```
<210> SEQ ID NO 14
<211> LENGTH: 9014
<212> TYPE: DNA
<213> ORGANISM: Artificial Sequence
<220> FEATURE:
<223> OTHER INFORMATION: Description of Artificial Sequence: Synthetic
      plasmid

<400> SEQUENCE: 14
```

```
gggcgaattg ggcccgacgt cgcatgctcc cggccgccat ggcggccgcg ggaattcgat     60

atcactagtg aattcgcggc cggcgattgg gcccgacgtc gcatgctccc ggccgccatg    120

gcggccgcgg gaattcgatt ccttaattaa gtcgactggg acccaaactt tggagtcgtt    180

gacagatgtg acaggtgaag cctgggatga catcgccaaa aatgcaacgt ctcactcatt    240

gtcactactc ccagggctca gtcgtcactg ggaaaaatct ccagaaggta gcgcgggcca    300

aggtgacagg tgtctgccaa gatctgcccg ccagactccc gggcggcgcg ctccctccct    360

gcaggccttc agcccgtcag catccccttc ctcggggccc tgctcactcc cagcctccat    420

ccccctgcca tctcctccgc cggtcgcgtg cggacacaag gatggggacc tcccagcgag    480

gagcgctctg ggcggggctc cggacgcatg cgcggccctc gtacggaagc ccggaaggag    540

gggcaggggg cggtggctca ggtttctccg ggcggcggcg gcggcggcgg cggcgacggc    600

gacggcgacg gcagcgggga cggcagcagt agcgggagca gcagcgtgga cgcggctggc    660

gctggcgcca tgaacccgct gtaaggcgca ggctgtgcag cacggggtgc gggggaggag    720

gaggaggacg ccgcggtgaa gttctccgcc atgaacctga ggggcctctt ccaggacttc    780

aacccgaggt gaggcggcgt cgttggcgcc cccgggagtc cgcgctgcgg gctcgggcgc    840

gggctggtgt tcggctccgg ggaggcacgg cgggcgagat gctgcagccc gaggacccgg    900

gcgcctgccc gagcctccct gcgggtgcaa gcggtcccca ggcaaaacag tcggcctcgg    960

cgcccgcccg cttcctcctc ccgtgcccgg tgctttcagc ccctgcccgg ccacggccgg   1020

aagggcccgg ccgcgagccc cgtcctgccc caagggaacc ccattctttt ctgcttgctg   1080

tccctcattg gtgtcccaac ttcttcgtct cggttccatc ctcttctgcg ccgctgcggg   1140

ccctccattc tccgcgtcag ggccgtctca ctcgacccaa cacccctacc cccaccccag   1200

ctgtttcctc cagttcctcg cagtccttgg ggttttcctt gggtttatgc ccatccctct   1260

cttgtttgct tctttgttga acggatacct gaaacactgt tgaatccttg gagtcagtgt   1320

cggggtatgg caatacctta tataatgcat ttctgggtga gcctgatcat tttccatact   1380

cattttctca tcagtcttca ctacaagttt atttgcagga agtagatatt gctgtccttc   1440

ttttccagat ggggaacacc cagtggacag tgtggagaaa acactggcta agcactcaag   1500
```

```
cgcctgtcct tgcacttgcc cgactgtttt gtaactgttc tttaccccag gctgtgagct   1560

ccctgaagct gagaccatct cctgctcatc tcagtgtccc cagcgcctcc cacccaccgt   1620

atctggcaca tagtaggcac atataaaatg tttgtggaac taaactgagc ccaaagactt   1680

ggattggaga cgaggccata tgtaactggg tgattctctg cccttctttg gcccttctgt   1740

aaaatgagga gttggcctaa ctgatctctt aaatgcacta ctctccgaaa ggagtatccg   1800

tttcccttat ttgccagttg ggaagacgtg ctcagtaaat atttgtgtgc tgtaacctat   1860

gttaggtgct ttagatgctg gcggtctcag catggggtga agaagggctt gtacacttaa   1920

gatgccttac agtactgtgc agtgctgtac tgcgggggcc aactctgggg acctatgcct   1980

tggctgcttg ttgaggatga aaggaagttt taggggagta tttgtatgtt gagggtgcag   2040

tctccctagg gatggtgaca ttttaacttg tgagtcattg tgactttgta tgtgccctta   2100

ttccactttg agttcatgtt ctggttagga gtgccagtgt ctctaacacg gtgcagacat   2160

tatcattgtt ggcttcgaag gcatagagga ggtaacagaa ctaactgcag tcccttcctc   2220

tgctgcatca gggggttaag attggtctgc agggtagtag ggttggtgct gtggctggac   2280

aagccctgta tgtcttctat ttggagatgg tgataagaaa gttaagtaaa aactgaattg   2340

ttttgtgccc ttgggcaact cacttatcta ttgttttatc tgtagaatga gtataatctc   2400

tcagtggggt agggaggcca attaaggatt gattacaaag tgccttacaa atagaaagct   2460

acagtgactt gtttgcaagg tgacagagaa ttcagaagcc tcaagaaact gccttaagtg   2520

atcaaacagg ctaacggagt tgccaaagca aaatagtgct gcactgatac tacctttaac   2580

cgtttttttcc tttagccctt ttccccccaa aaaaattagt atatgaaatt acagtgaaat   2640

acctggtatc taagcagatt tatagtaatt ctcaacatat tcatcaatct cttaattcta   2700

cctgcattaa aatgtatttc tacctgaaaa gtttaaaggt cttttatact gtgccatttt   2760

cctgattcat tgttgccaga ggtagtgagt tccttaattt tacagatatt tcaagaggac   2820

attggccagg tattattggt aaatcagatt tgttttttta gctggtagtg tttcacctct   2880

cctgagcact cctagttttt gacagtgtgc tttagtctcc ttccatgctg aggaaggcct   2940

tctctatagg agaaagaaaa ctgaggggtg tacacaggaa gttaccttat gctggggact   3000

caaaccttga tgctactgct ttgctccctg cctctatttt tgaaccaatt caacatctcc   3060

ctcctacccc aggaccttgt cacacactgt tctctttacc aggaatgttt ccctctcttt   3120

tcctctcctc cagacctagt gaactcctat ttatcctcac ttggcacttg ctaagggaag   3180

cattcctgac ttccctgacc agatttactg ctccctgttt ctacagttcc tgtagtattt   3240

actactcctc catcatagtg catatttgta cccttgtgtc tgtctggatg cttatttgat   3300

taatacctgc ctcccccact aaactttaag ctccatgggg tcaaggccgt gactgtgtca   3360

gtatcgtagc ctgcatactt ggaatagtac ctggctcaat aaatatttgt ggagtaaata   3420

actgaataac tctccagagc ctataagata aatctagagc tgctgctttc aatcactgct   3480

ttcctggtgg tctgtggcct ggttctcttt cttctcacac tcttcccacc ttcagagtgc   3540

agccattgct ttggagagat gggagagaac atggcactaa ggcagaatat ggctatattt   3600

actttgaaga gcatgtcttt gtcatagaaa tagtcactgt catggtttgg tgggtcccaa   3660

ggcatgggtc atggctccag atcccctttc cagccttttg gatcttggta agtctgaacc   3720

cactgctgcg ttggcaaggc tctggaaact atagtgacag agaatgattc acaagtgtca   3780

acactcagat gtacagggct gccagctgac ccactctacc tatttccatc tggcactgaa   3840

ctggttgatc atgaacttct tttcataatt gctttttagt tatgcaggtt aagacatgcc   3900
```

-continued

```
gaaacagatg taccggaccc acaaacaagt ccttccttga atgcctgagg cttcctaaca   3960
gtgaaagagc cctgttctta gagtaggcaa actgattctg aggcattgta ggtggtaggg   4020
atctggtagt aggtagcatt aggtgggctc ccggcactca ccatggagcc ttgaaatttt   4080
ctgctacttt gggggagttg ctggttcaga gaaggccctt ccaccctggt agccatgtgg   4140
cactggaagg ctgtgaaaac tctgctgggc cttcttagtc atctgttgtg agctcctgat   4200
gggagtgtgg tgtatccctc aggtgtgcta gactggaaca aaggctgaga agtgttgctc   4260
tgggggttcc aacttgtggg catggggtac tgatgagatc agtagtgttt ggagacttct   4320
gtatgctcca tcttcagaag acattctgga gtccatataa gttatcttgt ctcttgtttg   4380
aagcaggaaa aaggaatgcg attgctggta atatagttca ctaaagtcag ctacctggcc   4440
tctaacagtt atttgcaaag tatattataa cattgattcc tcaaacatct agattcctat   4500
ctcgtgccaa gtgatgtact aggtgctcta agtacaaaaa taaaggaata tagtcctcct   4560
ctcaatgcgt aagcctagtg gaagaagcag aaatgaaagg gaaataagaa ttcaatagag   4620
tatgaggcat tacagtgaaa gaaaccaaat gtcttagaag tacaaatggc agagctacta   4680
attctgtctc gagcaggcag ggaagagtct atagtggaaa tgacttttga gctagatttt   4740
gaattgagct agtcttttga gccagacttt tgagctagaa ttgtagggtt gtcatcagac   4800
cagagagtag gaagggtacc ttgtgaggaa gagagagaga gatcagattg ttactgtgtc   4860
tatgtagaaa aggaagacat aagaaactcc attttgatct gtactaagaa aaattgtttc   4920
tgctttgaga tgctgttaac ctgtaacttt agtcccaacc ctgtgctcac agaaacctgt   4980
gctgtaatga atcaaggttt aatggattta gggctgtgca ggatgtacct tgttaacaat   5040
atgtttgcag gcagtatgct tggtaaaagt catcgccatt ctccattctc gattaaccag   5100
ggacacagtg cactgcggaa ggccgcaggg acatctgccc aagaaagcct gggtattgtc   5160
caaggtttcc ccccactgag acagcctgag atatggcctt gtgggaaagg aaagacctta   5220
ccacccccca gcccgacacc cgtaaagtgt ctgtgctgag gaggagtagt gaaagagcgg   5280
ggcctctttg cagttgagat aagaggaagg cttctgtctc ctgctcatcc ctgggaatgg   5340
aatgtctctg tgtaaagctg accattccca ttcgttctat tctgagatag gagaaaacca   5400
ccctgtggct ggaggcgaag tatgctggca gcaatactgc tctgttactc tttgctacac   5460
tgagttgttt gggtaaagag aaacataaat ctagcctgcg tgcacatcca ggcacagtac   5520
ctttccttga acttattcat gatacagatt cctttgctca cgtttccctg ctgaccttct   5580
ccccacctgt tgccctgcta cactcccctc gctaagatag taaaaataat gatcagtaaa   5640
tactgaggta actcagaggc tagcgctggt gcgggtcctc cgtatgctga gtgccggtcc   5700
cctgggccca ctgttctttc tctatacttt gtttctgtgt cttatttctt ttctcagtct   5760
cgtcccacct gacgagaaat acccacaggt gtggaggggc tggccccttt cagtatctca   5820
gaagggacaa agtacacaaa ggcatggggt catgatagtg cctggtatgt tcaggtagtg   5880
aagaggtcca tgtggtatga gcactgcaga tgatatgtgt cgtatgaatt aaaaatacat   5940
agttactgca aatagttttt acaggttatt gtttttaaga aagcagtatc taatgcacga   6000
gtgtactgtc agtactgtca atgaactact taccactcaa gtgactgctt acgcgtcgaa   6060
tcactagtga attcgcggcc gcctgcaggt cgaccatatg ggagagctcc caacgcgttg   6120
gatgcatagc ttgagtattc tatagtgtca cctaaatagc ttggcgtaat catggtcata   6180
gctgtttcct gtgtgaaatt gttatccgct cacaattcca cacaacatac gagccggaag   6240
cataaagtgt aaagcctggg gtgcctaatg agtgagctaa ctcacattaa ttgcgttgcg   6300
```

-continued

```
ctcactgccc gctttccagt cgggaaacct gtcgtgccag ctgcattaat gaatcggcca   6360
acgcgcgggg agaggcggtt tgcgtattgg gcgctcttcc gcttcctcgc tcactgactc   6420
gctgcgctcg gtcgttcggc tgcggcgagc ggtatcagct cactcaaagg cggtaatacg   6480
gttatccaca gaatcagggg ataacgcagg aaagaacatg tgagcaaaag gccagcaaaa   6540
ggccaggaac cgtaaaaagg ccgcgttgct ggcgtttttc cataggctcc gcccccctga   6600
cgagcatcac aaaaatcgac gctcaagtca gaggtggcga aacccgacag gactataaag   6660
ataccaggcg tttccccctg gaagctccct cgtgcgctct cctgttccga ccctgccgct   6720
taccggatac ctgtccgcct ttctcccttc gggaagcgtg gcgctttctc atagctcacg   6780
ctgtaggtat ctcagttcgg tgtaggtcgt tcgctccaag ctgggctgtg tgcacgaacc   6840
ccccgttcag cccgaccgct gcgccttatc cggtaactat cgtcttgagt ccaacccggt   6900
aagacacgac ttatcgccac tggcagcagc cactggtaac aggattagca gagcgaggta   6960
tgtaggcggt gctacagagt tcttgaagtg gtggcctaac tacggctaca ctagaagaac   7020
agtatttggt atctgcgctc tgctgaagcc agttaccttc ggaaaaagag ttggtagctc   7080
ttgatccggc aaacaaacca ccgctggtag cggtggtttt tttgtttgca agcagcagat   7140
tacgcgcaga aaaaaaggat ctcaagaaga tcctttgatc ttttctacgg ggtctgacgc   7200
tcagtggaac gaaaactcac gttaagggat tttggtcatg agattatcaa aaaggatctt   7260
cacctagatc cttttaaatt aaaaatgaag ttttaaatca atctaaagta tatatgagta   7320
aacttggtct gacagttacc aatgcttaat cagtgaggca cctatctcag cgatctgtct   7380
atttcgttca tccatagttg cctgactccc cgtcgtgtag ataactacga tacgggaggg   7440
cttaccatct ggccccagtg ctgcaatgat accgcgagac ccacgctcac cggctccaga   7500
tttatcagca ataaaccagc cagccggaag ggccgagcgc agaagtggtc ctgcaacttt   7560
atccgcctcc atccagtcta ttaattgttg ccgggaagct agagtaagta gttcgccagt   7620
taatagtttg cgcaacgttg ttgccattgc tacaggcatc gtggtgtcac gctcgtcgtt   7680
tggtatggct tcattcagct ccggttccca acgatcaagg cgagttacat gatcccccat   7740
gttgtgcaaa aaagcggtta gctccttcgg tcctccgatc gttgtcagaa gtaagttggc   7800
cgcagtgtta tcactcatgg ttatggcagc actgcataat tctcttactg tcatgccatc   7860
cgtaagatgc ttttctgtga ctggtgagta ctcaaccaag tcattctgag aatagtgtat   7920
gcggcgaccg agttgctctt gcccggcgtc aatacgggat aataccgcgc cacatagcag   7980
aactttaaaa gtgctcatca ttggaaaacg ttcttcgggg cgaaaactct caaggatctt   8040
accgctgttg agatccagtt cgatgtaacc cactcgtgca cccaactgat cttcagcatc   8100
ttttactttc accagcgttt ctgggtgagc aaaaacagga aggcaaaatg ccgcaaaaaa   8160
gggaataagg gcgacacgga aatgttgaat actcatactc ttcctttttc aatattattg   8220
aagcatttat cagggttatt gtctcatgag cggatacata tttgaatgta tttagaaaaa   8280
taaacaaata ggggttccgc gcacatttcc ccgaaaagtg ccacctgatg cggtgtgaaa   8340
taccgcacag atgcgtaagg agaaaatacc gcatcaggaa attgtaagcg ttaatatttt   8400
gttaaaattc gcgttaaatt tttgttaaat cagctcattt tttaaccaat aggccgaaat   8460
cggcaaaatc ccttataaat caaaagaata gaccgagata gggttgagtg ttgttccagt   8520
ttggaacaag agtccactat taaagaacgt ggactccaac gtcaaagggc gaaaaaccgt   8580
ctatcagggc gatggcccac tacgtgaacc atcaccctaa tcaagttttt tggggtcgag   8640
gtgccgtaaa gcactaaatc ggaaccctaa agggagcccc cgatttagag cttgacgggg   8700
```

```
aaagccggcg aacgtggcga gaaaggaagg gaagaaagcg aaaggagcgg gcgctagggc   8760

gctggcaagt gtagcggtca cgctgcgcgt aaccaccaca cccgccgcgc ttaatgcgcc   8820

gctacagggc gcgtccattc gccattcagg ctgcgcaact gttgggaagg gcgatcggtg   8880

cgggcctctt cgctattacg ccagctggcg aaagggggat gtgctgcaag gcgattaagt   8940

tgggtaacgc cagggttttc ccagtcacga cgttgtaaaa cgacggccag tgaattgtaa   9000

tacgactcac tata                                                     9014
```

<210> SEQ ID NO 15
<211> LENGTH: 5954
<212> TYPE: DNA
<213> ORGANISM: Homo sapiens

<400> SEQUENCE: 15

```
ggccgcggga attcgattcc ttaattaagt cgactgggac ccaaactttg gagtcgttga     60

cagatgtgac aggtgaagcc tgggatgaca tcgccaaaaa tgcaacgtct cactcattgt    120

cactactccc agggctcagt cgtcactggg gaaaatctcc agaaggtagc gcgggccaag    180

gtgacaggtg tctgccaaga tctgcccgcc agactcccgg gcggcgcgct ccctccctgc    240

aggccttcag cccgtcagca tccccttcct cggggccctg ctcactccca gcctccatcc    300

ccctgccatc tcctccgccg gtcgcgtgcg gacacaagga tggggacctc ccagcgagga    360

gcgctctggg cggggctccg gacgcatgcg cggccctcgt acggaagccc ggaaggaggg    420

gcagggggcg gtggctcagg tttctccggg cggcggcggc ggcggcggcg gcgacggcga    480

cggcgacggc agcggggacg gcagcagtag cgggagcagc agcgtggacg cggctggcgc    540

tggcgccatg aacccgctgt aaggcgcagg ctgtgcagca cggggtgcgg gggaggagga    600

ggaggacgcc gcggtgaagt tctccgccat gaacctgagg ggcctcttcc aggacttcaa    660

cccgaggtga ggcggcgtcg ttggcgcccc cgggagtccg cgctgcgggc tcgggcgcgg    720

gctggtgttc ggctccgggg aggcacggcg ggcgagatgc tgcagcccga ggacccgggc    780

gcctgcccga gcctccctgc gggtgcaagc ggtccccagg caaaacagtc ggcctcggcg    840

cccgcccgct tcctcctccc gtgcccggtg ctttcagccc ctgcccggcc acggccggaa    900

gggcccggcc gcgagccccg tcctgcccca agggaacccc attcttttct gcttgctgtc    960

cctcattggt gtcccaactt cttcgtctcg gttccatcct cttctgcgcc gctgcgggcc   1020

ctccattctc cgcgtcaggg ccgtctcact cgacccaaca cccctacccc caccccagct   1080

gtttcctcca gttcctcgca gtccttgggg ttttccttgg gtttatgccc atccctctct   1140

tgtttgcttc tttgttgaac ggatacctga aacactgttg aatccttgga gtcagtgtcg   1200

gggtatggca ataccttata taatgcattt ctgggtgagc ctgatcattt tccatactca   1260

ttttctcatc agtcttcact acaagtttat ttgcaggaag tagatattgc tgtccttctt   1320

ttccagatgg ggaacaccca gtggacagtg tggagaaaac actggctaag cactcaagcg   1380

cctgtccttg cacttgcccg actgttttgt aactgttctt taccccaggc tgtgagctcc   1440

ctgaagctga gaccatctcc tgctcatctc agtgtcccca gcgcctccca cccaccgtat   1500

ctggcacata gtaggcacat ataaaatgtt tgtggaacta aactgagccc aaagacttgg   1560

attggagacg aggccatatg taactgggtg attctctgcc cttctttggc ccttctgtaa   1620

aatgaggagt tggcctaact gatctcttaa atgcactact ctccgaaagg agtatccgtt   1680

tcccttattt gccagttggg aagacgtgct cagtaaatat ttgtgtgctg taacctatgt   1740

taggtgcttt agatgctggc ggtctcagca tggggtgaag aagggcttgt acacttaaga   1800
```

```
tgccttacag tactgtgcag tgctgtactg cgggggccaa ctctggggac ctatgccttg   1860
gctgcttgtt gaggatgaaa ggaagtttta ggggagtatt tgtatgttga gggtgcagtc   1920
tccctaggga tggtgacatt ttaacttgtg agtcattgtg actttgtatg tgcccttatt   1980
ccactttgag ttcatgttct ggttaggagt gccagtgtct ctaacacggt gcagacatta   2040
tcattgttgg cttcgaaggc atagaggagg taacagaact aactgcagtc ccttcctctg   2100
ctgcatcagg gggttaagat tggtctgcag ggtagtaggg ttggtgctgt ggctggacaa   2160
gccctgtatg tcttctattt ggagatggtg ataagaaagt taagtaaaaa ctgaattgtt   2220
ttgtgccctt gggcaactca cttatctatt gttttatctg tagaatgagt ataatctctc   2280
agtggggtag ggaggccaat taaggattga ttacaaagtg ccttacaaat agaaagctac   2340
agtgacttgt ttgcaaggtg acagagaatt cagaagcctc aagaaactgc cttaagtgat   2400
caaacaggct aacggagttg ccaaagcaaa atagtgctgc actgatacta cctttaaccg   2460
tttttccttt tagccctttt ccccccaaaa aaattagtat atgaaattac agtgaaatac   2520
ctggtatcta agcagattta tagtaattct caacatattc atcaatctct taattctacc   2580
tgcattaaaa tgtatttcta cctgaaaagt ttaaaggtct tttatactgt gccattttcc   2640
tgattcattg ttgccagagg tagtgagttc cttaatttta cagatatttc aagaggacat   2700
tggccaggta ttattggtaa atcagatttg tttttttagc tggtagtgtt tcacctctcc   2760
tgagcactcc tagtttttga cagtgtgctt tagtctcctt ccatgctgag gaaggccttc   2820
tctataggag aaagaaaact gaggggtgta cacaggaagt taccttatgc tggggactca   2880
aaccttgatg ctactgcttt gctccctgcc tctatttttg aaccaattca acatctccct   2940
cctaccccag gaccttgtca cacactgttc tctttaccag gaatgtttcc ctctcttttc   3000
ctctcctcca gacctagtga actcctattt atcctcactt ggcacttgct aagggaagca   3060
ttcctgactt ccctgaccag atttactgct ccctgtttct acagttcctg tagtatttac   3120
tactcctcca tcatagtgca tatttgtacc cttgtgtctg tctggatgct tatttgatta   3180
atacctgcct cccccactaa actttaagct ccatggggtc aaggccgtga ctgtgtcagt   3240
atcgtagcct gcatacttgg aatagtacct ggctcaataa atatttgtgg agtaaataac   3300
tgaataactc tccagagcct ataagataaa tctagagctg ctgctttcaa tcactgcttt   3360
cctggtggtc tgtggcctgg ttctctttct tctcacactc ttcccacctt cagagtgcag   3420
ccattgcttt ggagagatgg gagagaacat ggcactaagg cagaatatgg ctatatttac   3480
tttgaagagc atgtctttgt catagaaata gtcactgtca tggtttggtg ggtcccaagg   3540
catgggtcat ggctccagat ccccttcca gccttttgga tcttggtaag tctgaaccca   3600
ctgctgcgtt ggcaaggctc tggaaactat agtgacagag aatgattcac aagtgtcaac   3660
actcagatgt acagggctgc cagctgaccc actctaccta tttccatctg gcactgaact   3720
ggttgatcat gaacttcttt tcataattgc tttttagtta tgcaggttaa gacatgccga   3780
aacagatgta ccggacccac aaacaagtcc ttccttgaat gcctgaggct tcctaacagt   3840
gaaagagccc tgttcttaga gtaggcaaac tgattctgag gcattgtagg tggtagggat   3900
ctggtagtag gtagcattag gtgggctccc ggcactcacc atggagcctt gaaattttct   3960
gctactttgg gggagttgct ggttcagaga aggcccttcc accctggtag ccatgtggca   4020
ctggaaggct gtgaaaactc tgctgggcct tcttagtcat ctgttgtgag ctcctgatgg   4080
gagtgtggtg tatccctcag gtgtgctaga ctggaacaaa ggctgagaag tgttgctctg   4140
gggttccaa cttgtgggca tggggtactg atgagatcag tagtgtttgg agacttctgt    4200
```

```
atgctccatc ttcagaagac attctggagt ccatataagt tatcttgtct cttgtttgaa   4260

gcaggaaaaa ggaatgcgat tgctggtaat atagttcact aaagtcagct acctggcctc   4320

taacagttat ttgcaaagta tattataaca ttgattcctc aaacatctag attcctatct   4380

cgtgccaagt gatgtactag gtgctctaag tacaaaaata aaggaatata gtcctcctct   4440

caatgcgtaa gcctagtgga agaagcagaa atgaaaggga aataagaatt caatagagta   4500

tgaggcatta cagtgaaaga aaccaaatgt cttagaagta caaatggcag agctactaat   4560

tctgtctcga gcaggcaggg aagagtctat agtggaaatg acttttgagc tagattttga   4620

attgagctag tcttttgagc cagacttttg agctagaatt gtagggttgt catcagacca   4680

gagagtagga agggtacctt gtgaggaaga gagagagaga tcagattgtt actgtgtcta   4740

tgtagaaaag gaagacataa gaaactccat tttgatctgt actaagaaaa attgtttctg   4800

ctttgagatg ctgttaacct gtaactttag tcccaaccct gtgctcacag aaacctgtgc   4860

tgtaatgaat caaggtttaa tggatttagg gctgtgcagg atgtaccttg ttaacaatat   4920

gtttgcaggc agtatgcttg gtaaaagtca tcgccattct ccattctcga ttaaccaggg   4980

acacagtgca ctgcggaagg ccgcagggac atctgcccaa gaaagcctgg gtattgtcca   5040

aggtttcccc ccactgagac agcctgagat atggccttgt gggaaaggaa agaccttacc   5100

accccccagc ccgacacccg taaagtgtct gtgctgagga ggagtagtga aagagcgggg   5160

cctctttgca gttgagataa gaggaaggct tctgtctcct gctcatccct gggaatggaa   5220

tgtctctgtg taaagctgac cattcccatt cgttctattc tgagatagga gaaaaccacc   5280

ctgtggctgg aggcgaagta tgctggcagc aatactgctc tgttactctt tgctacactg   5340

agttgtttgg gtaaagagaa acataaatct agcctgcgtg cacatccagg cacagtacct   5400

ttccttgaac ttattcatga tacagattcc tttgctcacg tttccctgct gaccttctcc   5460

ccacctgttg ccctgctaca ctcccctcgc taagatagta aaaataatga tcagtaaata   5520

ctgaggtaac tcagaggcta gcgctggtgc gggtcctccg tatgctgagt gccggtcccc   5580

tgggcccact gttctttctc tatactttgt ttctgtgtct tatttctttt ctcagtctcg   5640

tcccacctga cgagaaatac ccacaggtgt ggaggggctg gcccctttca gtatctcaga   5700

agggacaaag tacacaaagg catggggtca tgatagtgcc tggtatgttc aggtagtgaa   5760

gaggtccatg tggtatgagc actgcagatg atatgtgtcg tatgaattaa aaatacatag   5820

ttactgcaaa tagtttttac aggttattgt ttttaagaaa gcagtatcta atgcacgagt   5880

gtactgtcag tactgtcaat gaactactta ccactcaagt gactgcttac gcgtcgaatc   5940

actagtgaat tcgc                                                     5954
```

<210> SEQ ID NO 16
<211> LENGTH: 30756
<212> TYPE: DNA
<213> ORGANISM: Homo sapiens
<220> FEATURE:
<221> NAME/KEY: modified_base
<222> LOCATION: (5934)..(5934)
<223> OTHER INFORMATION: a, c, g, t, unknown or other
<220> FEATURE:
<221> NAME/KEY: misc_feature
<222> LOCATION: (5934)..(5934)
<223> OTHER INFORMATION: n is a, c, g, or t

<400> SEQUENCE: 16

```
gtacggaagc ccggaaggag gggcaggggg cggtggctca ggtttctccg ggcggcggcg     60

gcggcggcgg cggcgacggc gacggcgacg gcagcgggga cggcagcagt agcgggagca    120
```

-continued

```
gcagcgtgga cgcggctggc gctggcgcca tgaacccgct gtaaggcgca ggctgtgcag     180
cacggggtgc gggggaggag gaggaggacg ccgcggtgaa gttctccgcc atgaacctga     240
ggggcctctt ccaggacttc aacccgaggt gaggcggcgt cgttggcgcc cccgggagtc     300
cgcgctgcgg gctcgggcgc gggctggtgt tcggctccgg ggaggcacgg cgggcgagat     360
gctgcagccc gaggacccgg gcgcctgccc gagcctccct gcgggtgcaa gcggtcccca     420
ggcaaaacag tcggcctcgg cgcccgcccg cttcctcctc ccgtgcccgg tgctttcagc     480
ccctgcccgg ccacggccgg aagggcccgg ccgcgagccc cgtcctgccc caagggaacc     540
ccattctttt ctgcttgctg tccctcattg gtgtcccaac ttcttcgtct cggttccatc     600
ctcttctgcg ccgctgcggg ccctccattc tccgcgtcag ggccgtctca ctcgacccaa     660
cacccctacc cccaccccag ctgtttcctc cagttcctcg cagtccttgg ggttttcctt     720
gggtttatgc ccatccctct cttgtttgct tctttgttga acggatacct gaaacactgt     780
tgaatccttg gagtcagtgt cggggtatgg caatacctta tataatgcat ttctgggtga     840
gcctgatcat tttccatact cattttctca tcagtcttca ctacaagttt atttgcagga     900
agtagatatt gctgtccttc ttttccagat ggggaacacc cagtggacag tgtggagaaa     960
acactggcta agcactcaag cgcctgtcct tgcacttgcc cgactgtttt gtaactgttc    1020
tttaccccag gctgtgagct ccctgaagct gagaccatct cctgctcatc tcagtgtccc    1080
cagcgcctcc cacccaccgt atctggcaca tagtaggcac atataaaatg tttgtggaac    1140
taaactgagc ccaaagactt ggattggaga cgaggccata tgtaactggg tgattctctg    1200
cccttctttg gcccttctgt aaaatgagga gttggcctaa ctgatctctt aaatgcacta    1260
ctctccgaaa ggagtatccg tttcccttat ttgccagttg ggaagacgtg ctcagtaaat    1320
atttgtgtgc tgtaacctat gttaggtgct ttagatgctg gcggtctcag catggggtga    1380
agaagggctt gtacacttaa gatgccttac agtactgtgc agtgctgtac tgcgggggcc    1440
aactctgggg acctatgcct tggctgcttg ttgaggatga aaggaagttt taggggagta    1500
tttgtatgtt gagggtgcag tctccctagg gatggtgaca ttttaacttg tgagtcattg    1560
tgactttgta tgtgccctta ttccactttg agttcatgtt ctggttagga gtgccagtgt    1620
ctctaacacg gtgcagacat tatcattgtt ggcttcgaag gcatagagga ggtaacagaa    1680
ctaactgcag tcccttcctc tgctgcatca gggggttaag attggtctgc agggtagtag    1740
ggttggtgct gtggctggac aagccctgta tgtcttctat ttggagatgg tgataagaaa    1800
gttaagtaaa aactgaattg ttttgtgccc ttgggcaact cacttatcta ttgttttatc    1860
tgtagaatga gtataatctc tcagtggggt agggaggcca attaaggatt gattacaaag    1920
tgccttacaa atagaaagct acagtgactt gtttgcaagg tgacagagaa ttcagaagcc    1980
tcaagaaact gccttaagtg atcaaacagg ctaacggagt tgccaaagca aaatagtgct    2040
gcactgatac tacctttaac cgttttttcc tttagccctt ttccccccaa aaaaattagt    2100
atatgaaatt acagtgaaat acctggtatc taagcagatt tatagtaatt ctcaacatat    2160
tcatcaatct cttaattcta cctgcattaa aatgtatttc tacctgaaaa gtttaaaggt    2220
cttttatact gtgccatttt cctgattcat tgttgccaga ggtagtgagt tccttaattt    2280
tacagatatt tcaagaggac attggccagg tattattggt aaatcagatt tgttttttta    2340
gctggtagtg tttcacctct cctgagcact cctagttttt gacagtgtgc tttagtctcc    2400
ttccatgctg aggaaggcct tctctatagg agaaagaaaa ctgaggggtg tacacaggaa    2460
gttaccttat gctggggact caaaccttga tgctactgct ttgctccctg cctctatttt    2520
```

```
tgaaccaatt caacatctcc ctcctacccc aggaccttgt cacacactgt tctctttacc   2580
aggaatgttt ccctctcttt tcctctcctc cagacctagt gaactcctat ttatcctcac   2640
ttggcacttg ctaagggaag cattcctgac ttccctgacc agatttactg ctccctgttt   2700
ctacagttcc tgtagtattt actactcctc catcatagtg catatttgta cccttgtgtc   2760
tgtctggatg cttatttgat taatacctgc ctccccccact aaactttaag ctccatgggg   2820
tcaaggccgt gactgtgtca gtatcgtagc ctgcatactt ggaatagtac ctggctcaat   2880
aaatatttgt ggagtaaata actgaataac tctccagagc ctataagata aatctagagc   2940
tgctgctttc aatcactgct ttcctggtgg tctgtggcct ggttctcttt cttctcacac   3000
tcttcccacc ttcagagtgc agccattgct ttggagagat gggagagaac atggcactaa   3060
ggcagaatat ggctatattt actttgaaga gcatgtcttt gtcatagaaa tagtcactgt   3120
catggtttgg tgggtcccaa ggcatgggtc atggctccag atcccctttc cagccttttg   3180
gatcttggta agtctgaacc cactgctgcg ttggcaaggc tctggaaact atagtgacag   3240
agaatgattc acaagtgtca acactcagat gtacagggct gccagctgac ccactctacc   3300
tatttccatc tggcactgaa ctggttgatc atgaacttct tttcataatt gctttttagt   3360
tatgcaggtt aagacatgcc gaaacagatg taccggaccc acaaacaagt ccttccttga   3420
atgcctgagg cttcctaaca gtgaaagagc cctgttctta gagtaggcaa actgattctg   3480
aggcattgta ggtggtaggg atctggtagt aggtagcatt aggtgggctc ccggcactca   3540
ccatggagcc ttgaaatttt ctgctacttt gggggagttg ctggttcaga gaaggccctt   3600
ccaccctggt agccatgtgg cactggaagg ctgtgaaaac tctgctgggc cttcttagtc   3660
atctgttgtg agctcctgat gggagtgtgg tgtatccctc aggtgtgcta gactggaaca   3720
aaggctgaga agtgttgctc tgggggttcc aacttgtggg catggggtac tgatgagatc   3780
agtagtgttt ggagacttct gtatgctcca tcttcagaag acattctgga gtccatataa   3840
gttatcttgt ctcttgtttg aagcaggaaa aaggaatgcg attgctggta atatagttca   3900
ctaaagtcag ctacctggcc tctaacagtt atttgcaaag tatattataa cattgattcc   3960
tcaaacatct agattcctat ctcgtgccaa gtgatgtact aggtgctcta agtacaaaaa   4020
taaaggaata tagtcctcct ctcaatgcgt aagcctagtg gaagaagcag aaatgaaagg   4080
gaaataagaa ttcaatagag tatgaggcat tacagtgaaa gaaaccaaat gtcttagaag   4140
tacaaatggc agagctacta attctgtctc gagcaggcag ggaagagtct atagtggaaa   4200
tgacttttga gctagatttt gaattgagct agtcttttga gccagacttt tgagctagaa   4260
ttgtagggtt gtcatcagac cagagagtag gaagggtacc ttgtgaggaa gagagagaga   4320
gatcagattg ttactgtgtc tatgtagaaa aggaagacat aagaaactcc attttgatct   4380
gtactaagaa aaattgtttc tgctttgaga tgctgttaac ctgtaacttt agtcccaacc   4440
ctgtgctcac agaaacctgt gctgtaatga atcaaggttt aatggattta gggctgtgca   4500
ggatgtacct tgttaacaat atgtttgcag gcagtatgct tggtaaaagt catcgccatt   4560
ctccattctc gattaaccag ggacacagtg cactgcggaa ggccgcaggg acatctgccc   4620
aagaaagcct gggtattgtc caaggtttcc ccccactgag acagcctgag atatggcctt   4680
gtgggaaagg aaagacctta ccaccccccca gcccgacacc cgtaaagtgt ctgtgctgag   4740
gaggagtagt gaaagagcgg ggcctctttg cagttgagat aagaggaagg cttctgtctc   4800
ctgctcatcc ctgggaatgg aatgtctctg tgtaaagctg accattccca ttcgttctat   4860
tctgagatag gagaaaacca ccctgtggct ggaggcgaag tatgctggca gcaatactgc   4920
```

```
tctgttactc tttgctacac tgagttgttt gggtaaagag aaacataaat ctagcctgcg   4980
tgcacatcca ggcacagtac ctttccttga acttattcat gatacagatt cctttgctca   5040
cgtttccctg ctgaccttct ccccacctgt tgccctgcta cactcccctc gctaagatag   5100
taaaaataat gatcagtaaa tactgaggta actcagaggc tagcgctggt gcgggtcctc   5160
cgtatgctga gtgccggtcc cctgggccca ctgttctttc tctatacttt gtttctgtgt   5220
cttatttctt ttctcagtct cgtcccacct gacgagaaat acccacaggt gtggaggggc   5280
tggccccttt cagtatctca gaagggacaa agtacacaaa ggcatggggt catgatagtg   5340
cctggtatgt tcaggtagtg aagaggtcca tgtggtatga gcactgcaga tgatatgtgt   5400
cgtatgaatt aaaaatacat agttactgca aatagttttt acaggttatt gtttttaaga   5460
aagcagtatc taatgcacga gtgtactgtc agtactgtca atgaactact taccactcaa   5520
gtgactgctt acgcgtcgaa tcactagtga attcgcggcc gcctcgagtc tagaactagt   5580
ggatccccca aacgggccct ctagacgcgt tgacattgat tattgactag ttattaatag   5640
taatcaatta cggggtcatt agttcatagc ccatgatatc atatggagtt ccgcgttaca   5700
taacttacgg taaatggccc gcctggctga ccgcccaacg acccccgccc attgacgtca   5760
ataatgacgt atgttcccat agtaacgcca atagggactt tccattgacg tcaatgggtg   5820
gagtatttac ggtaaactgc ccacttggca gtacatcaag tgtatcatat gccaagtacg   5880
ccccctatt gacgtcaatg acggtaaatg gcccgcctgg cattatgccc agtncatgac    5940
cttatgggac tttcctactt ggcagacatc tacgtattag tcatcgctat taccatggtg   6000
atgcggtttt ggcagtacat caatgggcgt ggatagcggt ttgactcacg gggatttcc    6060
aagtctccac cccattgacg tcaatgggag tttgttttgg caccaaaatc aacgggactt   6120
tccaaaatgt cgtaacaact ccgccccatt gacgcaaatg ggcggtaggc gtgtacggtg   6180
ggaggtctat ataagcagag ctctctggct aactagagaa cccctgctta ctggcttatc   6240
gagatatctg cagaattcat ctgtcgactg ctaccggcag cgcgcagcgg caagaagtgt   6300
ctgggctggg acggacagga gaggctgtcg ccatcggcgt cctgtgcccc tctgctccgg   6360
cacggccctg tcgcagtgcc cgcgctttcc ccggcgcctg cacgcggcgc gcctgggtaa   6420
catgcttggg gtcctggtcc ttggcgcgct ggccctggcc ggcctggggt tccccgcacc   6480
cgcagagccg cagccgggtg gcagccagtg cgtcgagcac gactgcttcg cgctctaccc   6540
gggccccgcg accttcctca atgccagtca gatctgcgac ggactgcggg gccacctaat   6600
gacagtgcgc tcctcggtgg ctgccgatgt catttccttg ctactgaacg gcgacggcgg   6660
cgttggccgc cggcgcctct ggatcggcct gcagctgcca cccggctgcg gcgaccccaa   6720
gcgcctcggg cccctgcgcg gcttccagtg ggttacggga gacaacaaca ccagctatag   6780
caggtgggca cggctcgacc tcaatggggc tcccctctgc ggcccgttgt gcgtcgctgt   6840
ctccgctgct gaggccactg tgcccagcga gccgatctgg gaggagcagc agtgcgaagt   6900
gaaggccgat ggcttcctct gcgagttcca cttcccagcc acctgcaggc cactggctgt   6960
ggagcccggc gccgcggctg ccgccgtctc gatcacctac ggcaccccgt tcgcggcccg   7020
cggagcggac ttccaggcgc tgccggtggg cagctccgcc gcggtggctc ccctcggctt   7080
acagctaatg tgcaccgcgc cgcccggagc ggtccagggg cactgggcca gggaggcgcc   7140
gggcgcttgg gactgcagcg tggagaacgg cggctgcgag cacgcgtgca atgcgatccc   7200
tggggctccc cgctgccagt gcccagccgg cgccgccctg caggcagacg ggcgctcctg   7260
caccgcatcc gcgacgcagt cctgcaacga cctctgcgag cacttctgcg ttcccaaccc   7320
```

```
cgaccagccg ggctcctact cgtgcatgtg cgagaccggc taccggctgg cggccgacca   7380
acaccggtgc gaggacgtgg atgactgcat actggagccc agtccgtgtc cgcagcgctg   7440
tgtcaacaca cagggtggct tcgagtgcca ctgctaccct aactacgacc tggtggacgg   7500
cgagtgtgtg gagcccgtgg acccgtgctt cagagccaac tgcgagtacc agtgccagcc   7560
cctgaaccaa actagctacc tctgcgtctg cgccgagggc ttcgcgccca ttccccacga   7620
gccgcacagg tgccagatgt tttgcaacca gactgcctgt ccagccgact gcgaccccaa   7680
cacccaggct agctgtgagt gccctgaagg ctacatcctg gacgacggtt tcatctgcac   7740
ggacatcgac gagtgcgaaa acggcggctt ctgctccggg gtgtgccaca acctccccgg   7800
taccttcgag tgcatctgcg ggcccgactc ggcccttgcc cgccacattg gcaccgactg   7860
tgactccggc aaggtggacg gtggcgacag cggctctggc gagcccccgc ccagcccgac   7920
gcccggctcc accttgactc ctccggccgt ggggctcgtg cattcgggct tgctcatagg   7980
catctccatc gcgagcctgt gcctggtggt ggcgcttttg gcgctcctct gccacctgcg   8040
caagaagcag ggcgccgcca gggccaagat ggagtacaag tgcgcggccc cttccaagga   8100
ggtagtgctg cagcacgtgc ggaccgagcg gacgccgcag agactctgag cggcctccgt   8160
ccaggagcct ggctccgtcc aggagcctgt gcctcctcac cccagcttt gctaccaaag    8220
caccttagct ggcattacag ctggagaaga ccctccccgc accccccaag ctgttttctt   8280
ctattccatg gctaactggc gagggggtga ttagagggag gagaatgagc ctcggcctct   8340
tccgtgacgt cactggacca ctgggcaatg atggcaattt tgtaacgaag acacagactg   8400
cgatttgtcc caggtcctca ctaccgggcg caggagggtg agcgttattg gtcggcagcc   8460
ttctgggcag accttgacct cgtgggctag ggatgactaa aatatttatt tttttaagt    8520
atttaggttt ttgtttgttt cctttgttct tacctgtatg tctccagtat ccactttgca   8580
cagctctccg gtctctctct ctctacaaac tcccacttgt catgtgacag gtaaactatc   8640
ttggtgaatt tttttttcct agccctctca catttatgaa gcaagcccca cttattcccc   8700
attcttccta gttttctcct cccaggaact gggccaactc acctgagtca ccctacctgt   8760
gcctgaccct acttcttttg ctcttagctg tctgctcaga cagaacccct acatgaaaca   8820
gaaacaaaaa cactaaaaat aaaaatggcc atttgctttt tcaccagatt tgctaattta   8880
tcctgaaatt tcagattccc agagcaaaat aattttaaac aaaggttgag atgtaaaagg   8940
tattaaattg atgttgctgg actgtcatag aaattacacc caaagaggta tttatcttta   9000
cttttaaaca gtgagcctga attttgttgc tgttttgatt tgtactgaaa aatggtaatt   9060
gttgctaatc ttcttatgca atttcctttt ttgttattat tacttatttt tgacagtgtt   9120
gaaaatgttc agaaggttgc tctagattga gagaagagac aaacacctcc caggagacag   9180
ttcaagaaag cttcaaactg catgattcat gccaattagc aattgactgt cactgttcct   9240
tgtcactggt agaccaaaat aaaaccagct ctactggtct tgtggaattg ggagcttggg   9300
aatggatcct ggaggatgcc caattagggc ctagccttaa tcaggtcctc agagaatttc   9360
taccatttca gagaggcctt ttggaatgtg gcccctgaac aagaattgga agctgccctg   9420
cccatgggag ctggttagaa atgcagaatc ctaggctcca ccccatccag ttcatgagaa   9480
tctatattta acaagatctg cagggggtgt gtctgctcag taatttgagg acaaccattc   9540
cagactgctt ccaatttttct ggaatacatg aaatatagat cagttataag tagcaggcca   9600
agtcaggccc ttattttcaa gaaactgagg aattttcttt gtgtagcttt gctctttggt   9660
agaaaaggct aggtacacag ctctagacac tgccacacag ggtctgcaag gtctttggtt   9720
```

```
cagctaagct aggaatgaaa tcctgcttca gtgtatggaa ataaatgtat catagaaatg   9780
taacttttgt aagacaaagg ttttcctctt ctattttgta aactcaaaat atttgtacat   9840
agttatttat ttattggaga taatctagaa cacaggcaaa atccttgctt atgacatcac   9900
ttgtacaaaa taaacaaata acaatgtgaa aaaaaaaaaa aaaaaaaaaa aaaaaaaaaa   9960
aaaaaaaagg tagcagtcga cagatgaatt ccaccacact ggactagtgg atccgagctc  10020
ggtaccaagc ttaagtttgg gctgcaggaa ttctgatggc tctcaaaatt cctgcctcct  10080
ttagggataa aagactttaa gactttttaa caaaaaagaa aaagaaaaaa aaaattcctg  10140
cctcctggtg tacacacaca gaagggttcc ctccccttga atgtgaccag gatctgtgaa  10200
aataacggga tagccgctcc tgtgattagg ttatgtggta gactagagca agattctcct  10260
gctggttttg aagaagtcag ctgccatgtt gtgagactgt catgggctag ggcatgagcc  10320
tttaaatatc tgggagcaac ccctggccag cagccagtga gaaaacgggc cctcagtcct  10380
acaatcacaa ggaactaaat tctgccaaca acctgaagga actttgaaga ggatcatgag  10440
tcccttgatt cagcttgatg agcccctgag cagaggatac agctaacttg tactagggaa  10500
gtataaaaaa catgcatggg aatgatatat atcaacttta aggataattg tcatacttct  10560
gggaatgaag ggaaagaaat ggggctttag ttgtattatg atctttaatt tctcaaaaaa  10620
aataagatca gaagcaaata tggcaaaatg ttaatacttt tgtgggtacg taggtattca  10680
gcataccctt ttttctgagt tcaaaatatt ttataattaa aatgaaatgc aggccaggca  10740
cagtggctca tgcctataat accagcactt tgcgaggccg aggtgggagg atggcttgag  10800
gccagaccag cctggccaac atggcaaaac cccatctcta cttaaaaaaa aaaaaactat  10860
atatatatat atgtgtgtgt gtgtgtatat atatatatgt atatatattt atatatgtgt  10920
gtatatatat atatgtatat atatttatat atgtgtgtgt atatatatat atacacacac  10980
acacatatat acatacatac atacacacac acacacacac aattagccag gcatggtggc  11040
gcacacctgt agtcccagct acttgggagg ctgagacatg agaattgctt gaacctggga  11100
ggcagagtag ttagtgagct gagatcatac cactgcactc cagcctggtg acagagtgag  11160
actctgtctt aaaaaaaata aaaattaaaa ttaaatgcaa aaggtccaag tgaattgaag  11220
aggaaagggg tatcaaggaa ggttttgtgg aggtgacgtt tgagctgggt cttaaatgac  11280
ttaaacatgg gataagaagg gagggaataa ggacatttca ggtacgagaa ataaggagca  11340
aacagtggaa acaacctaac gtctgtcaac cagtgaatgg ataacaaaaa tgtaattcag  11400
atggtatcca acttacgatg gttcaacatg agatttttct gactttagga tagatttatc  11460
aaagtagtaa atccattttc aacttatgat attttcaact tcagatgggt ttatcaggac  11520
acagttgagg aacacctgtc tatccataca atttggcaat aaaaaggaaa tgagtgcaga  11580
tatactccac aacatgaatg aaccttgaaa acattaagtg agagaagcca gatacaaaag  11640
gccacatatt gtatgattct atttatacaa aatgtccaga ataggcaaat cttatagaca  11700
gcaagtaggt agatgatcag tttgctaggt gctgggggaa ggggaaatgg ggagtgatgg  11760
ctaaggggat tgggtttctt tgtggggcaa tgaaaatgtt ttaaaattga gcgtgataat  11820
gattgcacaa tgctgcatat atatataatc tatagattat atatatataa agagaggctg  11880
ttagacagtg ataagtgata tatatatata tatacataga gagagagaga gagagagaga  11940
gaggctgtta gtgataagtg atcaggaaaa taaaagtatt gaggaggaat acgaagttga  12000
cggtgtgaaa acatgagatt ttatatagga tggccaggga aggccttaat gagaaagtga  12060
cttatgagta aaaacaaggg atcctaaacc ttagcatgca tcagaatcac tcggaaactt  12120
```

-continued

```
gttaaagcat agcttgctgg gcctcatcac agatattttg attcggtagg ttcttgtctg  12180
atattaatac ttttggtcta gggaaccaca ttttgagaac cactgagcta aaggaagtaa  12240
aggtttccct tagtttacta gctggtaaca ctggcccagg aggcctttct ggaaaaggtc  12300
ccagtcccca aaggaagctg ggactcgcg ttcacatcgt caaggtttac caagttgtgg  12360
cgggcctttc cgtcttggaa aaagcctcaa aatggcagat tagggtgtcc atggccggcg  12420
gaaagggtct ttgaagttgc agaccaggag ggaagaagat tctgggcctc ccccatgcag  12480
tgtcagctgg caacagaatg caccccggct gggttggagg ccctgggtac tggctcttcc  12540
acaccagggg cccacctacc aagggcagca ggagcatctg cacctcctgc gccaggcgcc  12600
cttcagtgct tccacttgag cacctctcca gacaccagct agggtgacag tggtacaaat  12660
accagactcc cctggcctgc tcacctcaca gggtaatgtg ctgtggagtc agggggacac  12720
agcaaccacc agatgacatg gctggccccg gggaggacga cacgcagata cggctacttg  12780
gcacctgtga tattttacac actcgagagg ggcccgcacc atcctcagcc ctctccccac  12840
attcactctt agttcatgtc acctccaccc agagggggac acaggcccac agcgatggcc  12900
ccacaccctg cctgaggtcg cccacttccc aggaggcagt cctgggactt ccacccgacc  12960
aggccccaga gcccaccgac ttaacccctc cagaggcttg tcgttcatta ccttattcaa  13020
gatggagacc agccttttg cggagaaaat gcgggtgaag gtcctgaaag tgcattgacg  13080
ccgttttcgg aagccataca agtttagctg gcggaagaag ctctttatcg aagttgtggc  13140
aaacactttg tgtgcgacgt cccttttgag aatctccttt tcaaagagtt tttgattgat  13200
cactctacaa gccccactgt catcccacca gatggacgaa aactggttgc tgctgaccag  13260
tctccacagt ttctgtggaa aggggaggga gaggagatta tcttctccct ggggcgggac  13320
gtcaccgtca gggtgcggcc ttctgaacga agcttcctcg gccagaggtt ggaaagcgat  13380
ttcttctgtc agcagcctca agttagggct cccagtggac cccgggtcgt cccaggcagg  13440
ggaaggatct gctgggtgaa ggtaggtctc tgactgcaac tggggaggga aaggcaccct  13500
ttccaagcca tgatcctgtc ctctcgaatt tctttcttca cagcgagcca tactcaatga  13560
tcgcttgtcc tccatctggc aaacttgcta gtgcagtgtg gccagcagca cccccttggca  13620
gtcatgtaac cagccccatg acatcataaa ggggctctga ctgccggggg gtggcatctc  13680
cacccccagc aagttgtgta ataaagggcc aaggcagaca agtagctgcc catctgcatg  13740
tgcacattct ggtcctcaca gtcatttcaa tgggaaagat gacactagtg cacaagagtg  13800
ccgaggggcc ctgccacacc gtagatgcag acctggagcg gtccccttgt cctagagctc  13860
ctgagccagg cacaactaca gcaaagccct ggctcaggaa ggtcagagct caccgtctga  13920
gtcatgggcc cacagacccc agcacatgac tgacactcgg aagcacagaa caaagggtag  13980
gacggtgccc atgggtcagg ctgtagccac gccacccttt ccaccctgtc ctagccagag  14040
gcagcaatgt gctccataca gatcctccta acacacccac actgtcggtc cccagcacgc  14100
agatgcccga cagcccctta ggcaaatggc ttagctgact gccccaccac acgccgtcgc  14160
catgcagtcc agtggggagt cggaggcagc ctccttcctg cctctcctcg gcctgcacgt  14220
gtccccccac caggcagaga cccttctaca ccccgggtgt ctgcggtcac atcgcggtgg  14280
ggcatgcagc tgttggcctt cgagcatgtt ttgttttcct tggccagtgt ctccagagaa  14340
acgcacgtgg gtttgtgtcc agcggtccat ctctgcaaca gttgttcctt tgggattgga  14400
tgctaggagg tcacgggaga ggtgtccatc caaagcagtg tctgtgtcac acactgtccc  14460
cacacacagg gccacctctg cacagactcc cccgactcga ttctgggcac agagctcagt  14520
```

```
gaccttccag agactgccac gaaccggtga tgcctccacg cttgagacat cctgaccgca  14580
gggcccaagg cgcactggct cagggggtga cagtgagggg tctgcaaaca gactgctgat  14640
gctcaacccg gccgctgccg agctgtgtga cttgggcacg tcacttaacc tctctcggcc  14700
tctgtctcct cccggggata agagtagtag cacctgcttc ccggggctgt gaggatccag  14760
tgggacgtat aggaactagc gaggcaccgg cagttgggtc agagctactg ttgtcacttc  14820
acaaggcatt ttcttcaaca gcaagtcgga aatctcatga gcctaaggca gaatccacct  14880
gtggcctctg gttacaaccc acaggactga aaatccttcc agccacagca actggtgaat  14940
ttcctggtca attgccacaa gtcatgagct gaaccccact tgagtttcag ttcaggcaga  15000
actctagaga cgactagggc aagctagaca gcgactgcag agccttttgt tgcagcgtga  15060
gcagtcctca gctgttgaca tcactgggga gcaaacgagg accaggagcg gtgaaaggac  15120
agtgtctgct gcagattgtc gtagcaccca aggaacactc cagaaagcct cctaagcagt  15180
aacaagtgtg gcaaggtgta gcccagccaa cagtggcatc tgcgaggcgt cccctccttc  15240
ctcccactac cccgtatacc ctgggacctg tgcactgaag gactcattct aaaggctgtg  15300
cccctgcagc cgccagcctc actcactggc tgcctgtgcc agctagagat ttctttcctc  15360
tgaggctggc tgagaggacc actccagttt cctggcccat ccagcaaaga agatacacat  15420
catgcacgtg taaaatgagg aaccggttta ttgaacagct taaggagagc aaaaatagtg  15480
gctttagcta cattttttac acactgagca ggaaagtcta aaccatcccg ttcccctgta  15540
ccccaaagag aacagggctt gctggaggcc agtgccaagg gcggagtcgt gctcgcagca  15600
gacttgaatt aaccccatgt aggccggcga gcagttgccc gcgtgaaaac accaccctct  15660
tctcctggct gagaagatca aagctctttt tttaccctct tttcagcaaa ggacctattt  15720
gttttcaggc aggaggatgt taaacttgca gcctctgaca cacggtggaa cctgcagtgc  15780
ttggagaaac ggcacgcaca cgtgaaaaca tcatgcctac tccaaagcct tcttgttgct  15840
ggcaggaggg aagcttgaga ctttcccacg catagtcgtg acccgcgtgg ccgtttctgc  15900
tctcagcaac attctctagt gttccggctt caagcagcgc ttgtcaggtt tgaagctagc  15960
cactattctg agaacgtcag aaaagcatgg accatctctt gcttggtgtt gccgttgtgg  16020
cagtagcagc tactacgtac ctgcacgagt tccagggcag aagtggcaat gtcccatgaa  16080
ggcgtggcac cccacggggg gggggggga gtgtgccacg ggcgtccact tctgcagcag  16140
aaggcatgtg cctacagcac aagcttgtaa aaaaatactt gaacagaata tgctgtacag  16200
aactaggggt taacaccgca tatgaagatg ctaaaacatt tgtataaata ctctgtatac  16260
aagcatggag tcactcccgt agaaagggct catccgtgag gctatgaaaa actgctgtca  16320
gcatgcccaa agagaaacta cttccacagt aggaacagaa aaaaggactg tgctgtgtct  16380
aaacacgtgg tgcatcagag acatagttac agttcctact gactgcccca gccacgacct  16440
gggagtgctg aggacctggg agtgctcagc gagctgcagg aggtcagccc tgtggagaaa  16500
tacatttcta aacaatactt ttgattggga tttcagcacc gtatagacag atgttccttc  16560
tgggggcctg gcaagcagcc atctcccagt gggtctgacg ggaagagggg gtacctggag  16620
cccctcccag acagacggta atcccacccc tgttctcaca ctcttcctgg catccgcatc  16680
tgctggcaca cacccccgtc acctgccact tccgcgtccc gtcgtggtga gtggctgata  16740
ggcgctggat gcaaacaagg catgagatgg acgtacctgg agacccagct ccagtactgg  16800
ttctggtctg cggggtgaac gagggggcag aggaaggcgg agagagtgcg tcccagtcca  16860
cttaagctct gtccccggaa gtggcatcta atctggcatt tcgatattta atttgggagg  16920
```

-continued

```
tgggagcaca tacttcccag ggctctgggt aatgaccacc ctggccttct ttcgaaacat  16980
gggtgcgatt ttagggggct ccggaactgg ggtctcttcg gtttcttcat tatcttcgtg  17040
atggagatca taggaaatgt ttccatattc tcgtagaaat gggaagattt caagcagaaa  17100
ctgacagaaa tctttgcgga taccaaacca ccctgaaaaa taagaatttt ttatttcaca  17160
cacgaggctc aactgacctt cctgttaact ttctttccgt aacaagaagt ttcactccta  17220
caatgtcata acatacttta tccagactcc tgagtcacaa agcctgaaca gggcttgagt  17280
acccaaaatg gggaagaagt gcaaatgcta gctctgtggt gcttggagtg gggttcccgg  17340
accggcaggg acagcgtcca cggggcctag ttagggatgc cattctcggg ccccagccca  17400
gacctccaga aactgagtcg ggctagggtg ggctccagcg gtcccctttt cctggccctt  17460
ttgggattct gctggatgcc caaatttgag aactactgct ccagtgagtc tcaaaatatc  17520
tgtggtgcgc agactacggt gtcttccgct aatcttctcc agccaggata aactcatgga  17580
tgacagtgcc acccaagaac aagatttctg tcaccctctg gaatccgtga gggcggtagt  17640
catgcacggg ttggccagga gggggcctga actcatggag ccaccttaaa gccactttcc  17700
cagtcccact actcctctct gtaggctact ggagtgtcag ctcggtgcaa gccctccctg  17760
ctcccgggtg cggggtaggg ggcagaggca caaacagcaa gcacagcccg ggctgctggg  17820
ctgcagtgag gccctgcccc caaacccact ggctttccga agggcaatgc tctgggcttc  17880
cgtgccatgg agcccacagc cttgccagga aggcaccctc tgcagagatc gttttggaag  17940
tgtctgcctc agcaagcagg tggaggggaa tagagtgtta gcaaggcaag acaggcaaga  18000
ctcgggtgat ggcagcaagg atatggggga ggcagagcgg ccaacaggga cctaggatga  18060
atcccaggtt tgggtgggag atgtggattt tccatcaaac cctcccgggc ctgggaagaa  18120
tctgtcttga tccccatttt gcagaggagg gaacgggatc tctgagaggt tgcctgccgt  18180
gtctggttct acctcaaatg gcagcgtgca ctgcgagaaa agtcccggtg caggccagca  18240
gaacaccaga gttacggcat gcccttccct tagaaggtcc cagaatttcc tcagccctca  18300
ctttcccaca caagcttcta aattggggcc ctcggggact catcccttcc tagacttcta  18360
tccgccaccc cccacccct ggtccccccc cagacacaca ccaaggactt ctgaaatgct  18420
gagtacatac agtggtttcc tcccttctgt ccaaatgtgg ttgccatcag cgtgatcaac  18480
gagagccaaa gggggacaaa gatcgggatg caggagaagg cgttgtggcc atccagtttg  18540
tgaaccagca gaatctaaag aaagagacat agtcccggtt gatgccagca ccgaaaatgg  18600
gcagaggcgg aagccagact tcattaggca gttcctcccc accaccccac ccccgcgtga  18660
gctcccacaa gagggaacat cagcaccgcc agaaaaaggc aggaaaccac ctatccctgg  18720
ggaaagctcg aaatgagctt ttatgtccct cttcagagct cggcaatagc ctatccactt  18780
gaaaagttcc cagtgccagc agttttatgg caaactcctc cgggtgtttg ttctaaggag  18840
tcaacagctc ccattctaga attctccacg tgactccaat acacaaatct gacatcccac  18900
tctgctttcc ccagagtgga aactggagcc atacagaggc accatggcta aaaaggtgca  18960
ctcttctccc tgccagcccc acgtgctgcc cccaagagaa aggaaggatg ctctcctttc  19020
accgaagctc cctctcggag atggctgtgt tctctcccct ctcctggagt gggctcactg  19080
tgagctcgag ggacagaggc tgcctttcta ggggtgcaga atcctgtcag gggaagcgca  19140
agcttcaggg gctgaagagg cttcccgtgg aacgcttacc tcaaatgtaa gaaggggcac  19200
gacgatggtc atccagctca gggccatggt tatgtgtgtc ctgcgctgtc cgcaatcaca  19260
tccatagagc gcaagaacaa gacggaccac acaatgtagt agaggaccac caggcacaga  19320
```

```
aaggacatga gaatccacag cgggacacac acaacctggg ggtgggtgag agaacagcaa  19380
gagaagtctc tttagagctt ccaacctggc ctctgatgga aggcatcttt agcaccttgc  19440
tgtgtctgtc cagttaaggc ggtccttcct gtgagccgaa taaggaccgt tccatctccc  19500
aggactgctg ggagcatcgc tcaggacaga aaaggtatgg tatgttcact atggggcctg  19560
ctgccaccag ggacacacaa cgctcagtga gtcatcagtc cctcttcctt tgggtgacag  19620
acagccctgc acctggctcc gcagcctcta ctcttccaga ggcccactct cccacactct  19680
ctcaggctcc tctaggttct gctgccatca cagcttcccg ggaaatggga cacaactgtc  19740
accctgtgca cacacacaag atctcacccc aacagactct cttcacaggc aacattccca  19800
caacctgctg ggggtacttt ggcaacacaa atgggaatgg gctccccaga aagtctggct  19860
gcctgggctc ctaaggatcc ctaacctcac ccctaccaag ttagtgaact tggcgggttg  19920
atgctggata caggttgatg ctggatacgt agcgctgccg ggtcgtgacc cctaaggaat  19980
tatccaaact cttgttttta gatgctttat tatatcaaac tctcctttaa acaagtggcc  20040
catctgctgg gatttggaag cctgtaatac tgaaattttc atcataatgg aaattttaaa  20100
aacagaattt gacccacctg tttttaaaac actttcatta cttaacaaga ggtctaatct  20160
tgggcaagtc ttgaaatttc tctggcctta gtttcccatg tgttaaatga aacttgaagc  20220
agttggtctc ttatagtctc ctgactctaa cattctaaga attatatttg tacaataact  20280
caaaaatcac ataatttaat ttaccatatg gactccaaaa tatattttct cattaggcta  20340
aacttgatct gcattttctg gatgtgtcca tattcttgga ctacactaaa acatgatacc  20400
aatgcttcct ctcaccataa accctcactt cgctttctac atttaagaat tttatagctg  20460
gaagagtcct taacagaaaa taccatctaa taattacccc tcaaaatcga gaaagtccta  20520
tctgttctta tgctagttat aagaatgagg cagcatttca cataatggtt ataaacactg  20580
ccacaagaag attcatgatg tgttgtttat ctgtagctct catcatactc tgtcatataa  20640
ctatagcatt aagattttaa tgttctatat attcttctaa gacagtgttt accagagtaa  20700
ggcacaaaag atccactggt ttgcaagaaa gattagaact tttaaatttt ttacctcacc  20760
ttgtttaatc tatatttttg tatgtatttt gtaacatata tattattatt accataaatc  20820
atatataatt taaaatgcat atattagggg taaatgctca ggaaactttt tataaattgg  20880
gcatgcaaat acaagtttga agactcactg ttctaggtat taaaagtaaa gttataacca  20940
agtaaagctt ccacctttc atgtctcaaa gcagtttatt gttggaggta agatctctta  21000
gaagcctaaa caggtccaag tacagaatga agtaaggcta gcccataact tgtggcaagc  21060
aattcatact atttctctca tgctgagctc tcctcagtga agcagctact atagacaact  21120
gcagcctatt ggtagcctat tttacaggca ggaaaaaaat tacttttat tcaaagtgga  21180
actcaggaca tggggagaaa atgaatacaa aaaatagggt caatccaaag gcacacagca  21240
aatgagtaac acagttatgt tttttccca tttgtatgag gtcccagtaa attctaagta  21300
aactgcaaat ttaataatac actaaaaaag ccatgcaatt gttcaaatga atcccagcat  21360
ggtacaagga gtacagacac tagagtctaa aaaacaaaag aatgccatta ttgagttttt  21420
gaattatatc aagtagttac atctctactt aataaatgag aaaaacgagg ataagaggcc  21480
atttgataaa atgaaaatag ccaagaagtg gtattagaga cttgaataca ggtattcggg  21540
tccaaagttc atctgctcaa atactaactg gggaaaagag ggaaaaatat ttatatacat  21600
atatatctgc acacaaaaat acccccaaaa gacaaaatga ggccaggcag ggtggctcac  21660
acccgtaatc ccggtacttt gggaggctga ggcaggtgga tacctgagat caggagttgg  21720
```

-continued

```
agatcagcct ggtcaacatg gtgaaaccct gtctctacta aagataaaaa aattagccag  21780
gcatggtggc gtgcgcctgt aatcccagct acttgggagt ctgaggcagg agaatcactt  21840
gaactgggaa ggggaggttg cagtgagcca agatcgtact actgcactcc agcctgggca  21900
gcagagtgag actccatcac aaaaataaat aaataaataa aatacaatga aacagaaagt  21960
tcaaataatc ccataatctt accaccaaga aataactttc actcgttata cttattgatt  22020
tttccataat aaatgtactt tactgtgact atcatgaaaa gaaagttatt ttagaaacag  22080
agaactgttt cagatcaaat ctatgtagta gaacagagcc attaggtggg aaagacgaga  22140
tcaaactaaa tctcagaagg cctaaaaggc taggtccatt ccagcactaa aaactgacca  22200
gacaagtaat ggcttcaaca gcttctaaat atggacaaag catgctgaaa gggaaggaca  22260
ggtctaacag tggtatatga aatgaacagg aggggcaaag ctcatttctc ctctgaagtt  22320
ttccaaagat gctgaggagg acattagttt gacatgaccc tgatatggga caagataatt  22380
tcacagaagt tttacatgtt aaagttttct tatagatact cattcaagta agcaatgaac  22440
actaaaatct aaagaaagaa aagagcttta gagtcaggtc tgtattcaaa ttcaagctct  22500
accacttact ggttctgtga ctttgggcaa gtcttttaac cttattaagt cttaatttcc  22560
tgatttgtaa aatggggata tcgtctccct cacaggattg ttgtgaaact tttatgagat  22620
taatgccttt atatttggca tagtgtaagt aaacaataac tggcagcttc aaaaaaaaaa  22680
agcagtagca ttccatcatt tattattggt tactctcaaa aagtttttca atgtactaga  22740
agataaatat tcaaatacct taatatctcc attattttca ggtaaacagc atgctcctga  22800
acaaccaatg ggtcaacaaa taaattaaaa gggaaatcta aaaacatctt gatattaaac  22860
tacatggaag cacaatatac caaaaccaat ggttcacact aggagaattt taaggtacaa  22920
gaaaactctt tgagatttct taaaataata gtatgtctga atttattgag tgatttacca  22980
gaaactgttg taagagctct acttgcatta tagcacttaa tcctcttaac tctatggctg  23040
ctattatcaa cctcacccta atcacatatg ggacacagag aggttaagta acttgcccaa  23100
ggtcagagtt aggaagtact aagccatgct ttgaatcagt tgtcaggctc cggaactcac  23160
actttcagcc actacataat actgctttgc tatcttttag gaaactatgt gagtctacct  23220
cacatagact cacataggtt tgtttttttt tttttttaa aggctatctt ttcccccatc  23280
aatgtttttt gaaggatccc aaattagagt cccacagagg cagacagcag tacttgacaa  23340
tatggacatt taaggttaat gttggattct actgtctttt tactacatga cctagggaac  23400
gataattaac ctagactgct tccaagggtt aaataaccca tttagttata ctatgtaaat  23460
tatctcttag tgattgattg aaagcacact gttactaatt gactcggtat gaagtgcttt  23520
tttttcttcc ctttcaagat acatacottt ccagttaaag ttgagagatc atctccacca  23580
attactttta tgtcccctgt tgactggtca ttctagttaa aaaaaaaaaa aactatatat  23640
atatatatct acacacacat atgtatatgt atatccttat gtacacacac aaacttcaaa  23700
ttaaatgaga actagaagat ttgagaagtt agctagctaa tatccatagc attatgatat  23760
tctaaatgat atgaattata agaattaggt ttcctgaaat gaatgactag aaaactttca  23820
agtagagatt agtaaaaatt aaaaagtcct aatcggccat tactgatttg atgtttttaa  23880
gagtcctaaa aaatgggtta catccatttt taagtgggta gtattataac agccacccat  23940
cttcaatcac agtgatttct gaattgtgag ggaagttatt agcatgacag gtgtctggtt  24000
ctggccctgt acgattccca tgagtcaagc aaattgtaag ggctggtcta tatcacaccc  24060
aaccccaagg atatgtccct caaaagtcta gcccaggccc cgtcatcttc agcatcatct  24120
```

```
gggaaaccag gtctgattag tagtccttta aggaatacct cttaggctcc cattttactg  24180
ctatcacaga atccaataaa acccttacag gagattcaat gggaaatgct caacacccac  24240
tgtagttggt ggtgacaatg accataattt ggctgtgctg gattcaggac agaaaatttg  24300
ggtgaaagag caggtgaaca aaagagcttc gacttgccct agcagagagc aagccatacc  24360
ataccacaaa gccacagcaa ttacaacggt gcagtaccag cacagtaaat gaacaaagta  24420
gagcccagaa acagacccag aactatatga ggatttagta tacaataaag atggtatttc  24480
gagtcagtag ggaaaagatg aattattcaa taaatgatgt ttggccaact agtaacccat  24540
ttgggaaaaa ataaaagtat ggtccctacc tcacagcata cacaaaaata aattccagac  24600
ggattaaaat ctaaatgtaa aaaataaagc cataagtgga ctggaagaaa atagagaatt  24660
ttttttaaca tccgtagaaa gggtaaaaac ccaggcatga catgaaccaa aactgaagag  24720
gttctgtaac aaataccccc ttttatatat tgggctccaa caataagaac ccataggaaa  24780
atggagaatg aacacaaata gacaatttat agaagagaag gttataaggt gtaaaattat  24840
atctatctga gaaacaaaca ctaaaacaat gtgattctac tgttctccca cccatactgg  24900
caaaacttaa gcctgataat atgctgaggg gaaataagca ctcttgttgg tgagagtatt  24960
aattggcata gcttcttttg aaaatgacat agcaatacct gttaaaattg caaacatgca  25020
tgtcacttaa tccagtaatc ccacttctgg gaatcaatgc tacaaaaaca ctgacaagta  25080
tacaaagata cattcaagag tgttcactgg gccgggtgcg gtggcttcat gcctgtaatc  25140
ccagggaggc agaggcaaga cgatcgcttg accccaggag ttcaaggcca gcccgagaaa  25200
cacagcaaga ccctgtctct cttttttttta tttaaaaaat aaatgttcac tgtatcagtt  25260
gttcacaaaa acaaaccaac atgtccatta acagggaacc atttaaatta atcaagttca  25320
tctacacaat gtaataccat gcaactatta aaaagcacct gataatccaa agcacactga  25380
gacagaataa tgctattaaa aacaccaagt agtggaacac tgtgttgcct atgacaccat  25440
ttttattcaa catttaaaca aatttgtaac agcaattaca tgagtagtga caatggcgtt  25500
tatgagactt ttcactttta tgtgcttcta tttttgttat gcttctatat atacatccat  25560
ttattatgga gtgttacttt caaaaatcac aaatgggcca gtattatttg gtgttgcaag  25620
gtgagcatat gacttctgat atcaaccttt gcatattact tctcaattta gggaaattac  25680
agacatccct tattctaact aacttaaaac ccagcatttc aaacatacag aattgatggg  25740
gaaaaaaaag aaagaagaaa gaaagaaaag gcaacaagct tcagatgaca gtgactcaca  25800
tcaaattatt tataaaatct gttaaatagt gccatcttct ggagatacct ggtattacag  25860
tccaactcca gttgatgtct ttacagagac aagaggaata aaggaaaaaa tattcaagaa  25920
ctgaaaagta tggagtcatg gaaaaattgc tgtgatccaa aggctacggt gataggacaa  25980
gaaacaagag aactccaagc agtaagacac tgctgttcta ttagcatcca aacctccata  26040
ctcctgtttg ccccaaggct tttttaaaaa atagagacag gatctcacta ttttgctcag  26100
gctggtcttg aactcctgga ctcaagctat cctcctgcct cggcctccta aagtgccgag  26160
attacaggct tgagtcacca tacctggcta tttatttttt cttaactctc ttgcctggcc  26220
tatagccacc atggaagcta ataaagaata ttaatttaag agtaatggta tagttcacta  26280
cattggaata caggtataag tgcctacatt gtacatgaat ggcatacatg gatcaattac  26340
cccacctggg tggccaaagg aactgcgcga acctccctcc ttggctgtct ggaacaagct  26400
tcccactaga tccctttact gagtgcctcc ctcatcttta attatggtta agtctaggat  26460
aacaggactg gcaaaggtga ggggaaagct tcctccagag ttgctctacc ctctcctcta  26520
```

-continued

```
ccgtcctatc tcctcactcc tctcagccaa ggagtccaat ctgtcctgaa ctcagagcgt  26580
cactgtcaac tacataaaat tgccagagaa gctctttggg actacaaaca cataccctta  26640
atgtctttat ttctattttg tctacctctt cagtctaggt gaaaaaatag gaaggataat  26700
agggaagaac tttgtttatg cctacttatc cgcccctagg aattttgaaa acctctaggt  26760
agcaataaga actgcagcat ggtatagaaa aagaggagga aagctgtata gaaatgcata  26820
ataaatgggc aggaaaagaa ctgcttggaa caaacaggga ggttgaacta taaggagaga  26880
aagcagagag gctaatcaac aaggctgggt tcccaagagg gcatgatgag actattacta  26940
aggtaggaat tactaagggc tccatgtccc cttagtggct tagtactatg tagcttgctt  27000
tctgcagtga acttcagacc cttcttttag gatcctagaa tggacttttt tttttatcg   27060
gaaaacagtc attctctcaa cattcaagca ggccccaagt ctaccacact caatcacatt  27120
ttctcttcat atcataatct ctcaaccatt ctctgtcctt ttaactgttt ttctataccc  27180
tgatcaaatg ccaacaaaag tgagaatgtt agaatcatgt atttttagag gtagactgta  27240
tctcagataa aaaaaaaggg cagatattcc attttccaaa atatgtatgc agaaaaaata  27300
agtatgaaag gacatatgct caggtaacaa gttaatttgt ttacttgtat tttatgaatt  27360
ccctaaaacc tacgtcaccc gccccgttcc cacgccccgc gccacgtcac aaactccacc  27420
ccctcattat catattggct tcaatccaaa ataaggtata ttattgatga tgttaattaa  27480
catgcatgga tccatatgcg gtgtgaaata ccgcacagat gcgtaaggag aaaataccgc  27540
atcaggcgct cttccgcttc ctcgctcact gactcgctgc gctcggtcgt tcggctgcgg  27600
cgagcggtat cagctcactc aaaggcggta atacggttat ccacagaatc aggggataac  27660
gcaggaaaga acatgtgagc aaaaggccag caaaaggcca ggaaccgtaa aaaggccgcg  27720
ttgctggcgt ttttccatag gctccgcccc cctgacgagc atcacaaaaa tcgacgctca  27780
agtcagaggt ggcgaaaccc gacaggacta taaagatacc aggcgtttcc ccctggaagc  27840
tccctcgtgc gctctcctgt tccgaccctg ccgcttaccg gatacctgtc cgcctttctc  27900
ccttcgggaa gcgtggcgct ttctcatagc tcacgctgta ggtatctcag ttcggtgtag  27960
gtcgttcgct ccaagctggg ctgtgtgcac gaaccccccg ttcagcccga ccgctgcgcc  28020
ttatccggta actatcgtct tgagtccaac ccggtaagac acgacttatc gccactggca  28080
gcagccactg gtaacaggat tagcagagcg aggtatgtag gcggtgctac agagttcttg  28140
aagtggtggc ctaactacgg ctacactaga aggacagtat ttggtatctg cgctctgctg  28200
aagccagtta ccttcggaaa aagagttggt agctcttgat ccggcaaaca aaccaccgct  28260
ggtagcggtg gtttttttgt ttgcaagcag cagattacgc gcagaaaaaa aggatctcaa  28320
gaagatcctt tgatcttttc tacggggtct gacgctcagt ggaacgaaaa ctcacgttaa  28380
gggattttgg tcatgagatt atcaaaaagg atcttcacct agatcctttt aaattaaaaa  28440
tgaagtttta aatcaatcta aagtatatat gagtaaactt ggtctgacag ttaccaatgc  28500
ttaatcagtg aggcacctat ctcagcgatc tgtctatttc gttcatccat agttgcctga  28560
ctccccgtcg tgtagataac tacgatacgg gagggcttac catctggccc cagtgctgca  28620
atgataccgc gagacccacg ctcaccggct ccagatttat cagcaataaa ccagccagcc  28680
```

```
ggaagggccg agcgcagaag tggtcctgca actttatccg cctccatcca gtctattaat  28740
tgttgccggg aagctagagt aagtagttcg ccagttaata gtttgcgcaa cgttgttgcc  28800
attgctgcag ccatgagatt atcaaaaagg atcttcacct agatcctttt cacgtagaaa  28860
gccagtccgc agaaacggtg ctgaccccgg atgaatgtca gctactgggc tatctggaca  28920
agggaaaacg caagcgcaaa gagaaagcag gtagcttgca gtgggcttac atggcgatag  28980
ctagactggg cggttttatg gacagcaagc gaaccggaat tgccagctgg ggcgccctct  29040
ggtaaggttg ggaagccctg caaagtaaac tggatggctt tcttgccgcc aaggatctga  29100
tggcgcaggg gatcaagctc tgatcaagag acaggatgag gatcgtttcg catgattgaa  29160
caagatggat tgcacgcagg ttctccggcc gcttgggtgg agaggctatt cggctatgac  29220
tgggcacaac agacaatcgg ctgctctgat gccgccgtgt tccggctgtc agcgcagggg  29280
cgcccggttc tttttgtcaa gaccgacctg tccggtgccc tgaatgaact gcaagacgag  29340
gcagcgcggc tatcgtggct ggccacgacg ggcgttcctt gcgcagctgt gctcgacgtt  29400
gtcactgaag cgggaaggga ctggctgcta ttgggcgaag tgccggggca ggatctcctg  29460
tcatctcacc ttgctcctgc cgagaaagta tccatcatgg ctgatgcaat gcggcggctg  29520
catacgcttg atccggctac ctgcccattc gaccaccaag cgaaacatcg catcgagcga  29580
gcacgtactc ggatggaagc cggtcttgtc gatcaggatg atctggacga agagcatcag  29640
gggctcgcgc cagccgaact gttcgccagg ctcaaggcga gcatgcccga cggcgaggat  29700
ctcgtcgtga cccatggcga tgcctgcttg ccgaatatca tggtggaaaa tggccgcttt  29760
tctggattca tcgactgtgg ccggctgggt gtggcggacc gctatcagga catagcgttg  29820
gctacccgtg atattgctga agagcttggc ggcgaatggg ctgaccgctt cctcgtgctt  29880
tacggtatcg ccgctcccga ttcgcagcgc atcgccttct atcgccttct tgacgagttc  29940
ttctgaattt tgttaaaatt tttgttaaat cagctcattt tttaaccaat aggccgaaat  30000
cggcaaaatc ccttataaat caaaagaata gaccgagata gggttgagtg ttgttccagt  30060
ttggaacaag agtccactat taaagaacgt ggactccaac gtcaaagggc gaaaaaccgt  30120
ctatcagggc gatggcccac tacgtgaacc atcaccctaa tcaagttttt tggggtcgag  30180
gtgccgtaaa gcactaaatc ggaaccctaa agggagcccc cgatttagag cttgacgggg  30240
aaagccggcg aacgtggcga gaaaggaagg gaagaaagcg aaaggagcgg gcgctagggc  30300
gctggcaagt gtagcggtca cgctgcgcgt aaccaccaca cccgccgcgc ttaatgcgcc  30360
gctacagggc gcgtccattc gccattcagg atcgaattaa ttcttaatta acatcatcaa  30420
taatatacct tattttggat tgaagccaat atgataatga gggggtggag tttgtgacgt  30480
ggcgcggggc gtgggaacgg ggcgggtgac gtagtagtgt ggcggaagtg tgatgttgca  30540
agtgtggcgg aacacatgta agcgacggat gtggcaaaag tgacgttttt ggtgtgcgcc  30600
ggtgtacaca ggaagtgaca attttcgcgc ggttttaggc ggatgttgta gtaaatttgg  30660
gcgtaaccga gtaagatttg gccattttcg cgggaaaact gaataagagg aagtgaaatc  30720
tgaataattt tgtgttactc atagcgcgta atactg                            30756
```